(12) United States Patent
Nomura et al.

(10) Patent No.: US 8,318,322 B2
(45) Date of Patent: Nov. 27, 2012

(54) AROMATIC AMINE COMPOUND, AND LIGHT-EMITTING ELEMENT, LIGHT-EMITTING DEVICE, AND ELECTRONIC DEVICE USING AROMATIC AMINE COMPOUND

(75) Inventors: Hiroko Nomura, Fukuoka (JP); Sachiko Kawakami, Kanagawa (JP); Takahiro Ushikubo, Kanagawa (JP); Harue Osaka, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 181 days.

(21) Appl. No.: 12/466,139

(22) Filed: May 14, 2009

(65) Prior Publication Data

US 2009/0284143 A1    Nov. 19, 2009

(30) Foreign Application Priority Data

May 16, 2008   (JP) .................................. 2008-130154

(51) Int. Cl.
*H01L 51/54* (2006.01)

(52) U.S. Cl. ........ 428/690; 428/917; 313/504; 313/505; 313/506; 257/40; 257/E51.05; 257/E51.026; 257/E51.032; 564/426; 564/434

(58) Field of Classification Search .................. 428/690, 428/917; 313/504, 505, 506; 257/40, E51.05, 257/E51.026, E51.032; 564/426, 434
See application file for complete search history.

(56) References Cited

U.S. PATENT DOCUMENTS

2007/0215889 A1   9/2007 Kawakami et al.

FOREIGN PATENT DOCUMENTS

| JP | 09-249876 | * | 9/1997 |
| JP | 2003-031371 | * | 1/2003 |
| JP | 2003-317946 | * | 11/2003 |
| JP | 2007-284431 | | 11/2007 |

OTHER PUBLICATIONS

Ho, M-H et al, "P-131: Novel Deep Blue Dopants for Organic Light Emitting Devices," SID 05 Digest: SID International Symposium Digest of Technical Papers, vol. XXXVI, 2005, pp. 802-805.

* cited by examiner

*Primary Examiner* — Jennifer Chriss
*Assistant Examiner* — Gregory Clark
(74) *Attorney, Agent, or Firm* — Husch Blackwell LLP

(57) ABSTRACT

Novel aromatic amine compounds are provided. Light-emitting elements having high emission efficiency and high reliability are provided. Further, light-emitting devices and electronic devices using the light-emitting devices are provided. Specifically, an aromatic amine compound represented by the general formula (1), and light-emitting elements, light-emitting devices and electronic devices that are formed using the aromatic amine compound represented by the general formula (1) are provided. By using the aromatic amine compound represented by the general formula (1) for light-emitting elements, light-emitting devices and electronic devices, the light-emitting elements, light-emitting devices and electronic devices can have high emission efficiency.

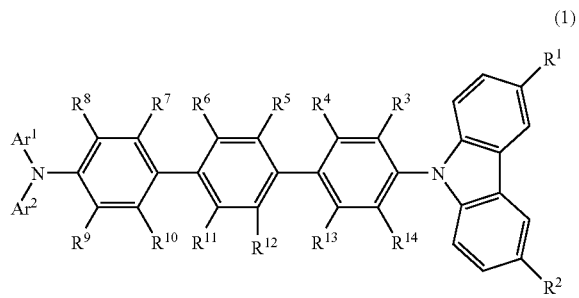

(1)

18 Claims, 23 Drawing Sheets

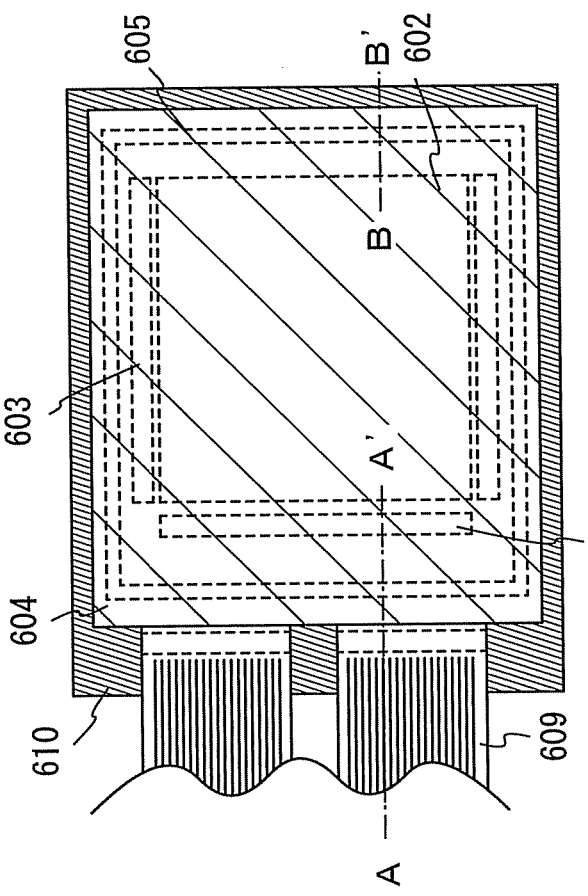
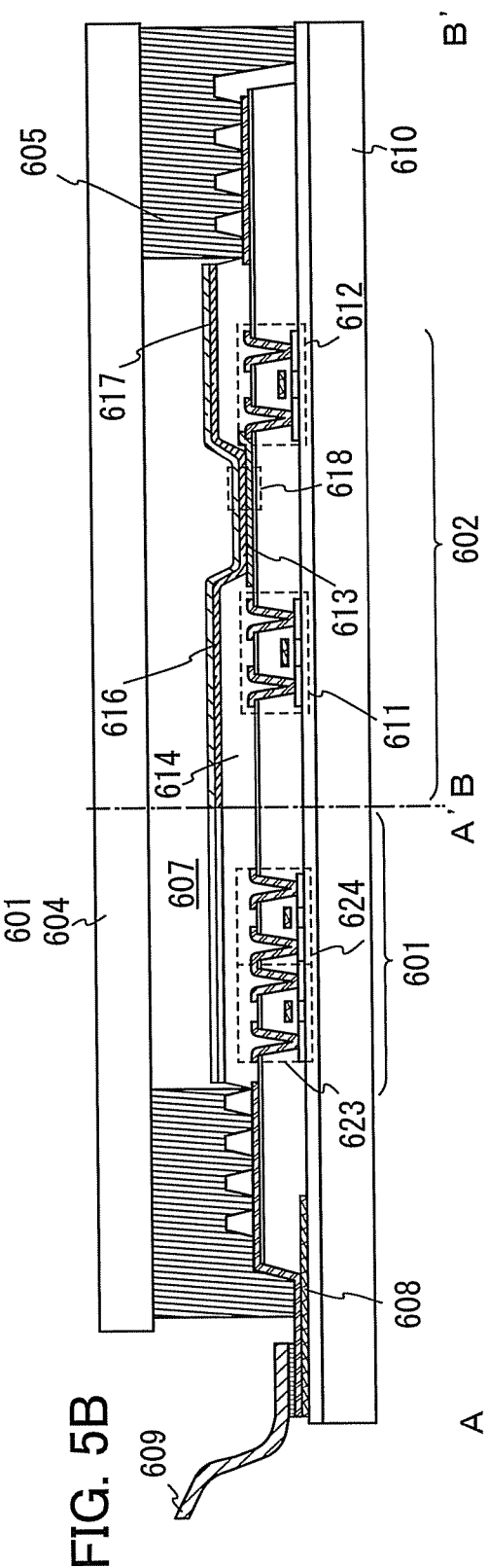
FIG. 5A
FIG. 5B

AROMATIC AMINE COMPOUND, AND LIGHT-EMITTING ELEMENT, LIGHT-EMITTING DEVICE, AND ELECTRONIC DEVICE USING AROMATIC AMINE COMPOUND

BACKGROUND OF THE INVENTION

1. Field of the Invention

The present invention relates to aromatic amine compounds, and light-emitting elements, light-emitting devices, and electronic devices using the aromatic amine compounds.

2. Description of the Related Art

In recent years, research and development have been extensively conducted on light-emitting elements using light-emitting compounds. The light-emitting elements have a basic structure in which a layer containing a light-emitting organic compound is interposed between a pair of electrodes. By applying a voltage to such an element, electrons and holes are injected into the layer containing the light-emitting organic compound from the pair of electrodes, and thus current flows therein. Then, these carriers (electrons and holes) are recombined and thus the light-emitting organic compound is excited. When returning from the excited state to the ground state, the light-emissive organic compound emits light. Because of this mechanism, such a light-emitting element is called a current-excitation light-emitting element.

Such a light-emitting element has a significant advantage in that it can be fabricated to be thin and light because it is formed as an about 0.1-μm-thick organic film, for example. Another advantage is high response speed since the period from carrier injection to light emission is about 1μ second or less. Such advantageous features are effective for flat panel display elements.

Also, because these light-emitting elements are formed as films, planar light emission can be easily obtained by forming a large-area element. On the other hand, point light sources typified by a filament lamp and an LED or linear light sources typified by a fluorescent light do not have the above features; therefore, these light-emitting elements are of value as surface light sources applicable to a lighting device and the like.

Because such a light-emitting element has a number of problems about materials, improvement and development etc., of element structures and materials have been conducted in order to enhance the characteristic thereof.

For example, Non-Patent Document 1 and Patent Document 1 describe light-emitting elements using a blue light-emitting material.
[Patent Document 1]
Japanese Published Patent Application No. 2007-284431
[Non-Patent Document 1]
Meng-Huan Ho, Yao-Shan Wu and Chin H. Chen, 2005 SID International Symposium Digest of Technical Papers, Vol. XXXVI. pp. 802-805.

SUMMARY OF THE INVENTION

In a light-emitting element described in Non-Patent Document 1, 4,4'-bis[N-(1-naphthyl)-N-phenylamino]biphenyl (abbreviation: NPB) is used for a layer in contact with a light-emitting layer. However, NPB has low singlet-excitation energy and energy is likely to transfer from an excited light-emitting material to NPB. In particular, in a case where a light-emitting material of blue that is a short-wavelength color, is used, energy is more likely to transfer to NPB because of a high energy level in an excited state. If energy transfers to NPB, a problem occurs in that emission efficiency of the light-emitting element decreases.

In a light-emitting element described in Patent Document 1, an aromatic amine compound having a 9-[4-(N-phenylamino)phenyl]carbazole (abbreviation: YGA) skeleton, represented by a structural formula (10) below, is used for a layer in contact with a light-emitting layer.

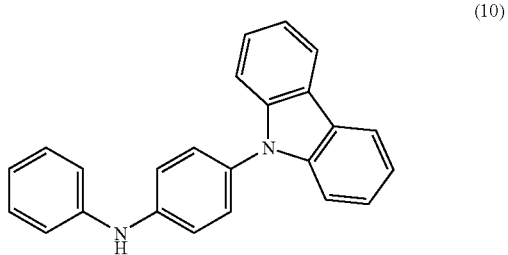

Because any compound having a YGA skeleton has a low highest occupied molecular orbital (HOMO) level (that is, the absolute value is large), by using such a compound as a layer to be in contact with the light-emitting layer, a light-emitting element with high emission efficiency can be fabricated. However, in a case where an aromatic amine compound having a YGA skeleton is used, it is difficult to obtain a light-emitting element with high reliability.

In view of the above, it is an object of one embodiment of the present invention to provide a novel aromatic amine compound.

It is another object of one embodiment of the present invention to provide a light-emitting element, a light-emitting device, and an electronic device having high emission efficiency.

It is another object of one embodiment of the present invention to provide a light-emitting element, a light-emitting device, and an electronic device having high reliability.

One embodiment of the present invention is an aromatic amine compound represented by a general formula (1).

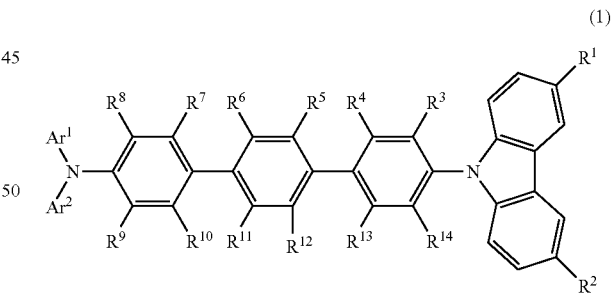

In the formula, $R^1$ and $R^2$ are independently a hydrogen atom, an alkyl group having 1 to 4 carbon atoms, or an aryl group having 6 to 13 carbon atoms. In addition, $R^3$ to $R^{14}$ are independently a hydrogen atom or an alkyl group having 1 to 4 carbon atoms. Also, $Ar^1$ and $Ar^2$ are independently an aryl group having 6 to 13 carbon atoms. The aryl group having 6 to 13 carbon atoms may further have a substituent, and such substituents of the aryl group may be bound to each other to form a ring.

The aromatic amine compound represented by the general formula (1) is preferably an aromatic amine compound represented by a general formula (2).

(2)

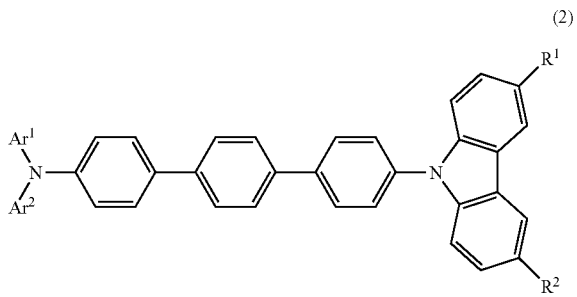

In the formula, $R^1$ and $R^2$ are independently a hydrogen atom, an alkyl group having 1 to 4 carbon atoms, or an aryl group having 6 to 13 carbon atoms. Also, $Ar^1$ and $Ar^2$ are independently an aryl group having 6 to 13 carbon atoms. The aryl group having 6 to 13 carbon atoms may further have a substituent, and the substituents of the aryl group may be bound to each other to form a ring.

An aromatic amine compound represented by a general formula (3) is more preferable.

(3)

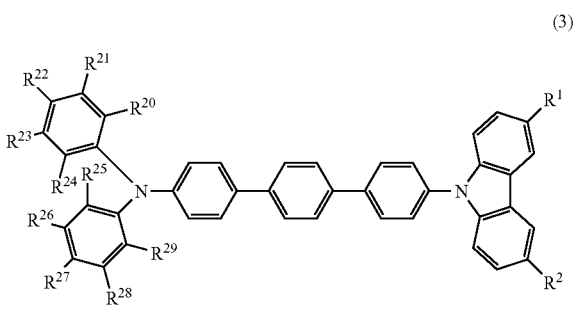

In the formula, $R^1$ and $R^2$ are independently a hydrogen atom, an alkyl group having 1 to 4 carbon atoms, or an aryl group having 6 to 13 carbon atoms. The aryl group having 6 to 13 carbon atoms may further have a substituent, and the substituents of the aryl group may be bound to each other to form a ring. Also, $R^{20}$ to $R^{29}$ are independently a hydrogen atom, an alkyl group having 1 to 4 carbon atoms, a phenyl group, or a naphthyl group.

An aromatic amine compound represented by a general formula (4) is even more preferable.

(4)

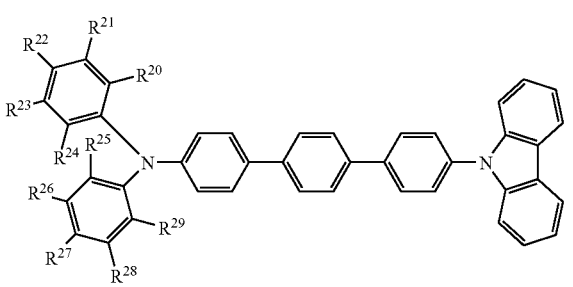

In the formula, $R^{20}$ to $R^{29}$ are independently a hydrogen atom, an alkyl group having 1 to 4 carbon atoms, a phenyl group, or a naphthyl group.

One embodiment of the present invention is a light-emitting element having any of the above aromatic amine compounds between a pair of electrodes.

Another embodiment of the present invention is a light-emitting element including, between a pair of electrodes, a light-emitting layer and a layer in contact with the light-emitting layer containing any of the above aromatic amine compounds.

Another embodiment of the present invention is a light-emitting element having a light-emitting layer containing any of the above aromatic amine compounds between a pair of electrodes.

In the above structure, the light-emitting layer may include a phosphorescent material that emits phosphorescent light.

Alternatively, in the above structure, the light-emitting layer may include a fluorescent material that emits fluorescent light. In particular, more advantageous effects can be obtained when the light-emitting layer includes a fluorescent material that emits blue light.

One embodiment of the present invention is a light-emitting device having a light-emitting element including any of the above aromatic amine compounds. Note that the term "light-emitting devices" in this specification include image display devices, devices which is able to emit light, and light sources (including lighting devices). In addition, the "light-emitting devices" of the present invention include all types of modules such as a module in which a panel is attached with a connector such as an FPC (flexible printed circuit), a TAB (tape automated bonding) tape or a TCP (tape carrier package); a module in which a printed wiring board is provided on the tip of a TAB tape or a TCP; and a module in which an IC (integrated circuit) is directly mounted on a light-emitting element by the COG (chip on glass) technique.

Further, an electronic device using the above-described light-emitting element for a display portion is another embodiment of the present invention. Therefore, an electronic device that is one embodiment of the present invention includes a display portion, and the aforementioned light-emitting element is included in the display portion.

By fabricating a light-emitting element using an aromatic amine compound of an embodiment of the present invention, transfer of excitation energy from the light-emitting material can be prevented, and the emission efficiency can be improved. In addition, even if an aromatic amine compound of an embodiment of the present invention is excited, energy can transfer from the aromatic amine compound to the light-emitting material; therefore, the emission efficiency can be improved.

Further, by fabricating the light-emitting element using an aromatic amine compound of an embodiment of the present invention, a highly reliable light-emitting element that can emit light stably and has a long lifetime can be provided.

By using the light-emitting element using an aromatic amine compound of an embodiment of the present invention for a light-emitting device and an electronic device, the light-emitting device and the electronic device can provide high emission efficiency.

BRIEF DESCRIPTION OF THE DRAWINGS

In the accompanying drawings.

FIGS. 5A and 5B illustrate a light-emitting device according to one embodiment of the present invention;

DETAILED DESCRIPTION OF THE INVENTION

Figure 1A:
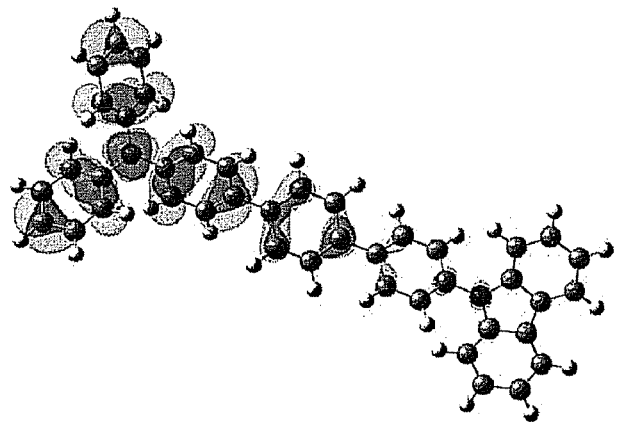
FIGS. 1A to 1C illustrate the highest occupied molecular orbitals of Compounds 1 to 3.

Hereinafter, embodiments of the present invention will be described in detail with reference to the accompanying drawings. However, the present invention is not limited to the following description, and various changes and modifications for the modes and details thereof will be apparent to those skilled in the art unless such changes and modifications depart from the spirit and scope of the present invention. Therefore, the present invention should not be interpreted as being limited to the description of the embodiments described below.

Embodiment 1

Embodiment 1 will describe an aromatic amine compound according to one embodiment of the present invention.

An aromatic amine compound of this embodiment is an aromatic amine compound expressed by a general formula (1).

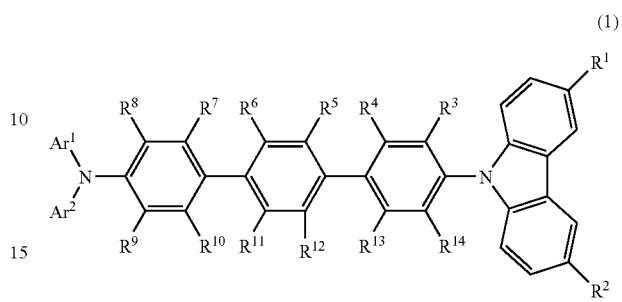

(1)

In the formula, $R^1$ and $R^2$ are independently a hydrogen atom, an alkyl group having 1 to 4 carbon atoms or an aryl group having 6 to 13 carbon atoms. In addition, $R^3$ to $R^{14}$ are independently a hydrogen atom or an alkyl group having 1 to 4 carbon atoms. $Ar^1$ and $Ar^2$ are independently an aryl group having 6 to 13 carbon atoms. The aryl group having 6 to 13 carbon atoms may further have a substituent, and substituents of the aryl group may be bound to each other to form a ring.

In the general formula (1), $R^1$ and $R^2$ are independently a hydrogen atom, an alkyl group having 1 to 4 carbon atoms, or an aryl group having 6 to 13 carbon atoms. In addition, the aryl group having 6 to 13 carbon atoms may further have a substituent such as an alkyl group having 1 to 4 carbon atoms and/or an aryl group having 6 to 13 carbon atoms, and such substituents may be bound to each other to form a ring. Specific examples of $R^1$ and $R^2$ include substituents represented by structural formulae (11-1) to (11-25).

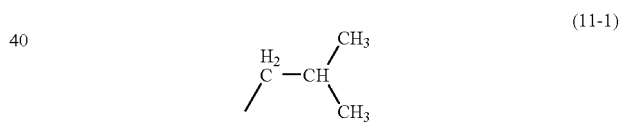

(11-1)

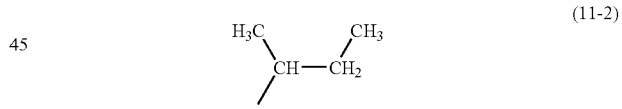

(11-2)

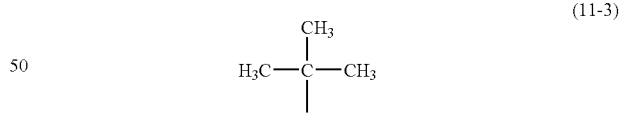

(11-3)

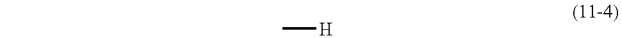

(11-4)

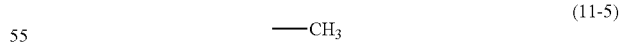

(11-5)

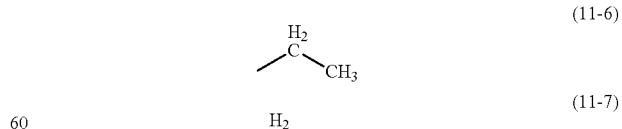

(11-6)

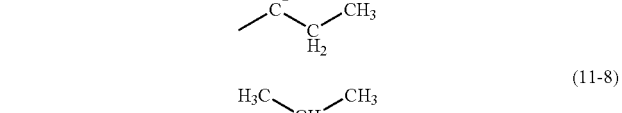

(11-7)

(11-8)

(11-9) 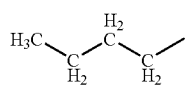
(11-10) 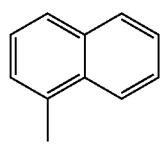
(11-11) 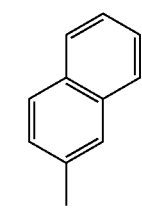
(11-12) 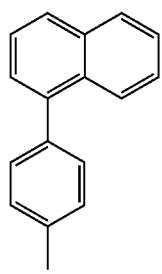
(11-13) 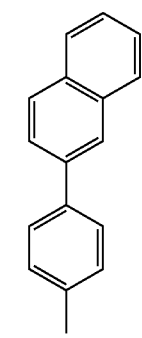
(11-14) 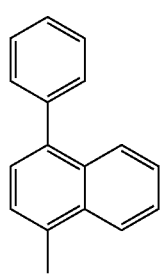
(11-15) 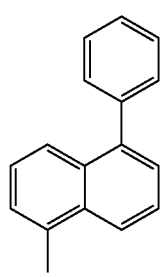
(11-16) 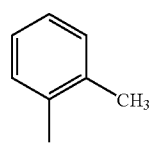
(11-17) 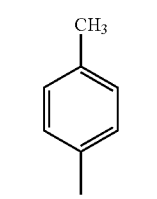
(11-18) 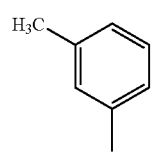
(11-19) 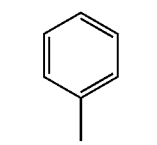
(11-20) 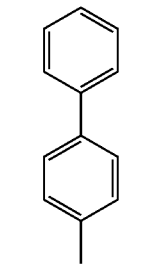
(11-21) 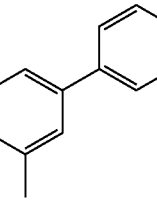
(11-22) 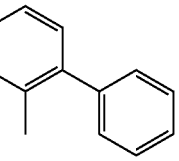
(11-23) 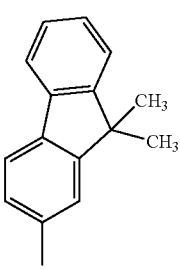

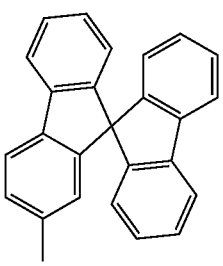
(11-24)

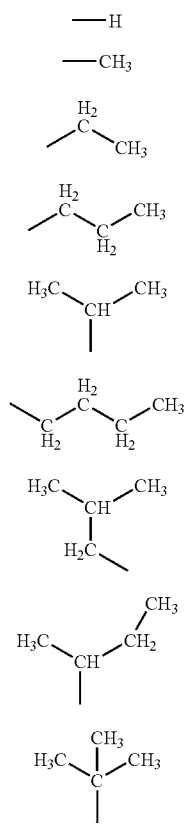
(11-25)

In the general formula (1), $R^3$ to $R^{14}$ are independently a hydrogen atom or an alkyl group having 1 to 4 carbon atoms. Specific examples thereof include substituents represented by structural formulae (12-1) to (12-9).

—H  (12-1)

—CH₃  (12-2)

$\text{—CH}_2\text{—CH}_3$  (12-3)

$\text{—CH}_2\text{—CH}_2\text{—CH}_3$  (12-4)

$\text{—CH(CH}_3\text{)}_2$  (12-5)

$\text{—CH}_2\text{—CH}_2\text{—CH}_2\text{—CH}_3$  (12-6)

$\text{—CH}_2\text{—CH(CH}_3\text{)}_2$  (12-7)

$\text{—CH(CH}_3\text{)—CH}_2\text{—CH}_3$  (12-8)

$\text{—C(CH}_3\text{)}_3$  (12-9)

In the general formula (1), $Ar^1$ and $Ar^2$ are independently an aryl group having 6 to 13 carbon atoms. The aryl group having 6 to 13 carbon atoms may further have a substituent such as an alkyl group having 1 to 4 carbon atoms and/or an aryl group having 6 to 13 carbon atoms, and such substituents may be bound to each other to form a ring. Specific examples of $Ar^1$ and $Ar^2$ include substituents represented by structural formulae (13-1) to (13-26).

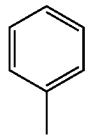
(13-1)

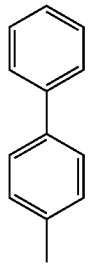
(13-2)

(13-3)

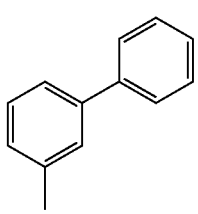
(13-4)

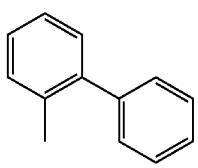
(13-5)

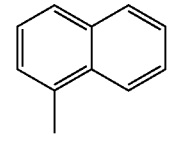
(13-6)

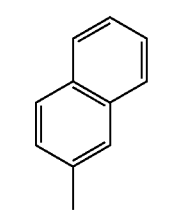
(13-7)

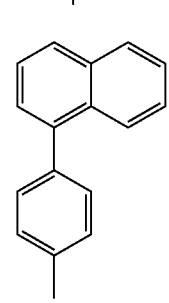

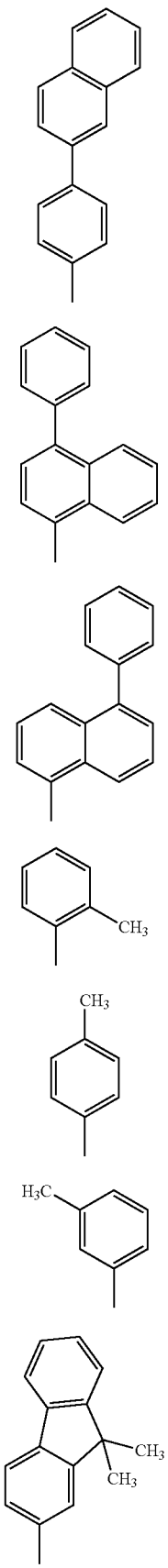

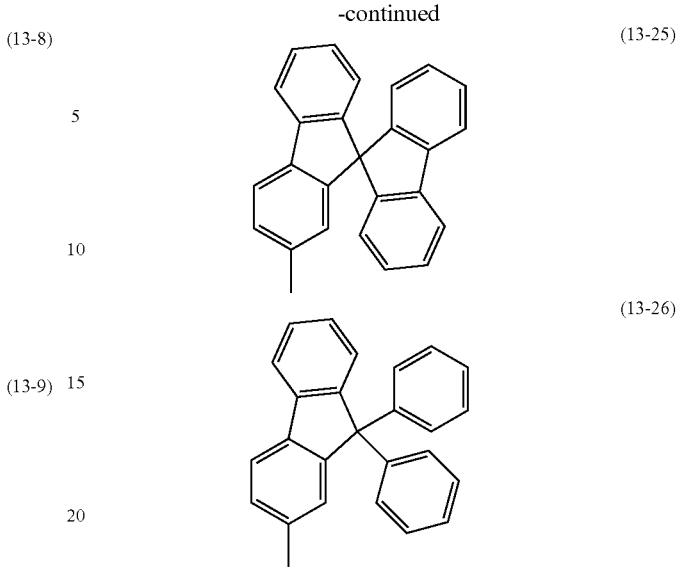

The aromatic amine compound represented by the general formula (1) is preferably an aromatic amine compound represented by a general formula (2).

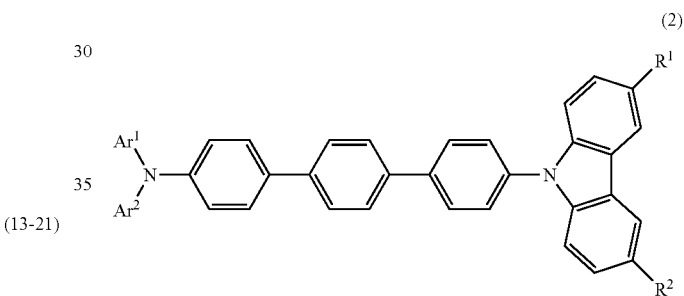

In the formula, $R^1$ and $R^2$ are independently a hydrogen atom, an alkyl group having 1 to 4 carbon atoms, or an aryl group having 6 to 13 carbon atoms. $Ar^1$ and $Ar^2$ are independently an aryl group having 6 to 13 carbon atoms. The aryl group having 6 to 13 carbon atoms may further have a substituent and substituents of the aryl group may be bound to each other to form a ring.

An aromatic amine compound represented by a general formula (3) is more preferable.

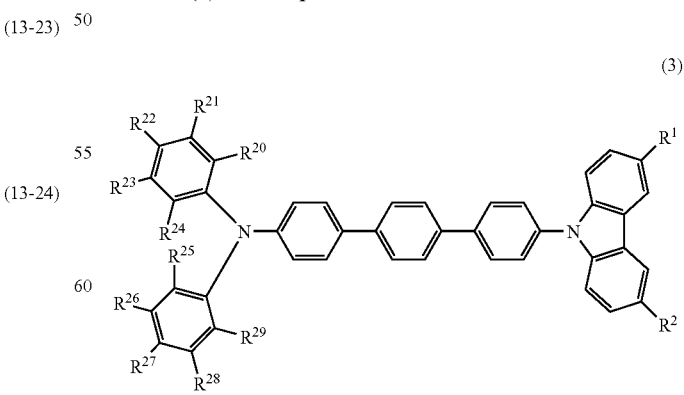

In the formula, $R^1$ and $R^2$ are independently a hydrogen atom, an alkyl group having 1 to 4 carbon atoms, or an aryl group having 6 to 13 carbon atoms. In addition, $R^{20}$ to $R^{29}$ are independently a hydrogen atom, an alkyl group having 1 to 4 carbon atoms, a phenyl group or a naphthyl group. The aryl group having 6 to 13 carbon atoms may further have a substituent and substituents of the aryl group may be bound to each other to form a ring.

In the general formula (3), $R^{20}$ to $R^{29}$ are independently a hydrogen atom, an alkyl group having 1 to 4 carbon atoms, a phenyl group, or a naphthyl group. Specifically, substituents represented by structure formulae (14-1) to (14-15) are given.

(14-1)
—H (14-2)
—CH₃

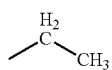
(14-3)

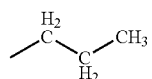
(14-4)

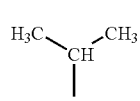
(14-5)

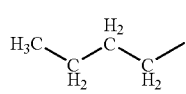
(14-6)

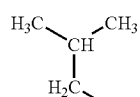
(14-7)

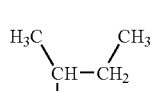
(14-8)

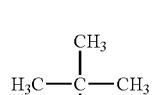
(14-9)

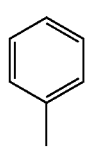
(14-10)

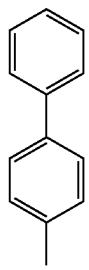
(14-11)

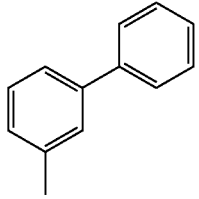
(14-12)

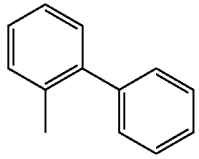
(14-13)

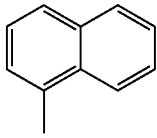
(14-14)

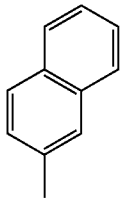
(14-15)

An aromatic amine compound represented by a general formula (4) is more preferable.

(4)

In the formula, $R^{20}$ to $R^{29}$ are independently a hydrogen atom, an alkyl group having 1 to 4 carbon atoms, a phenyl group, or a naphthyl group.

Specific examples of the aromatic amine compounds in this embodiment include, but not limited to, aromatic amine compounds represented by structural formulae (21) to (118).

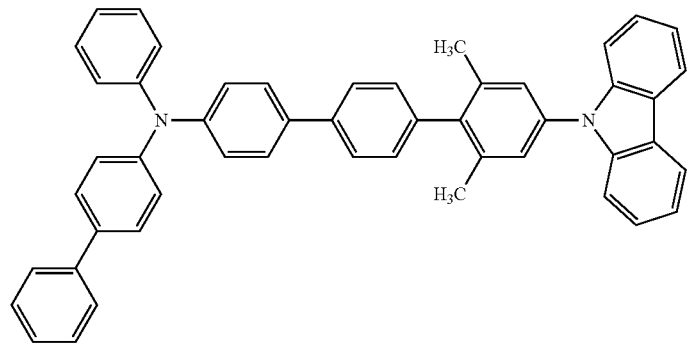
(21)
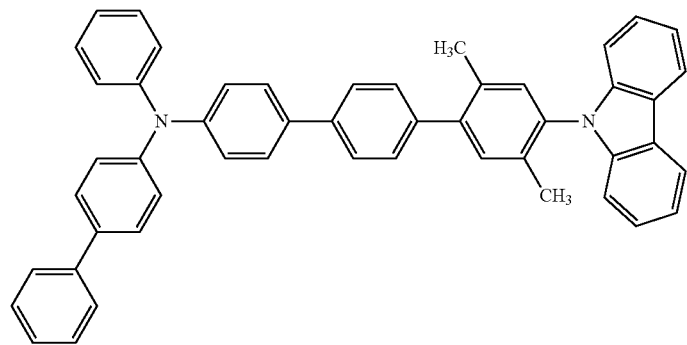
(22)
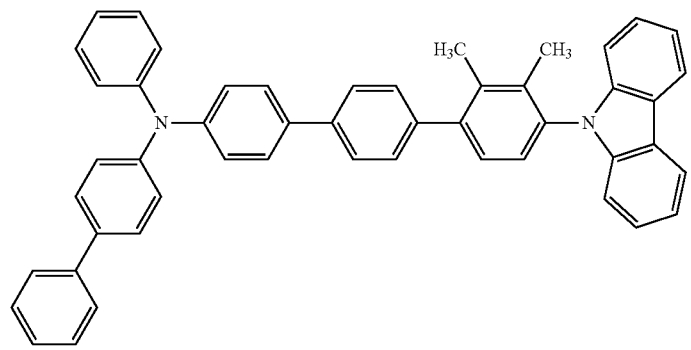
(23)
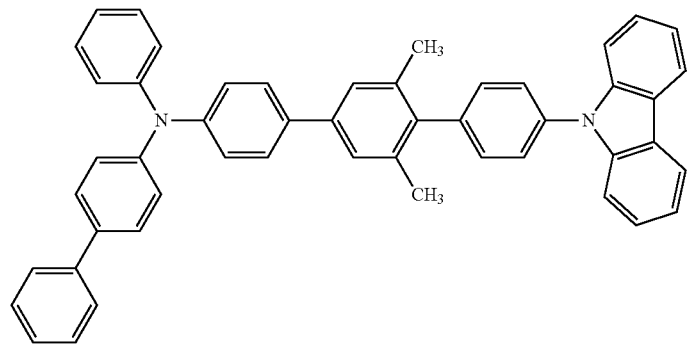
(24)

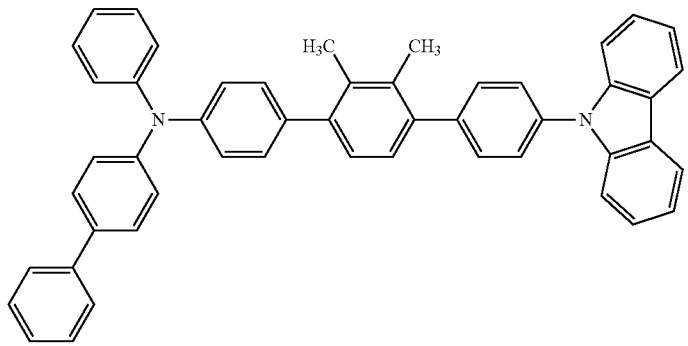
(25)
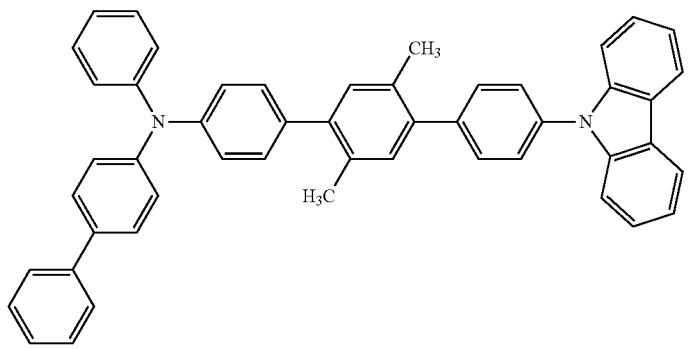
(26)
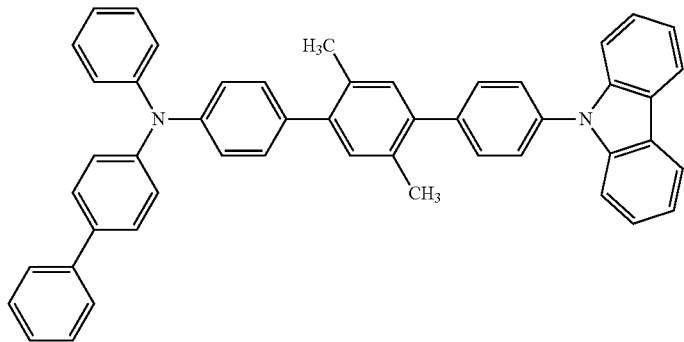
(27)
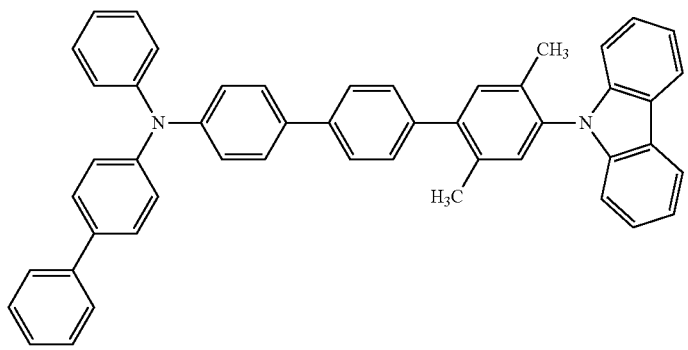
(28)

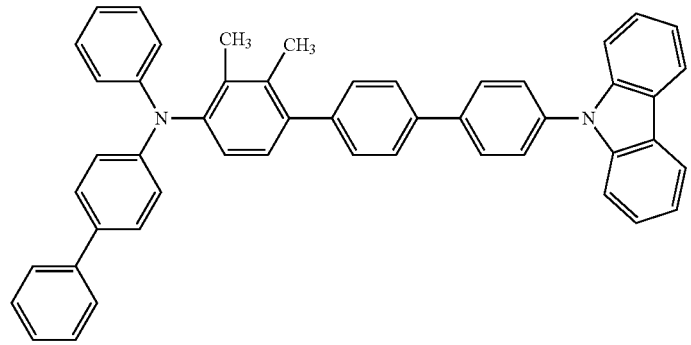
(29)
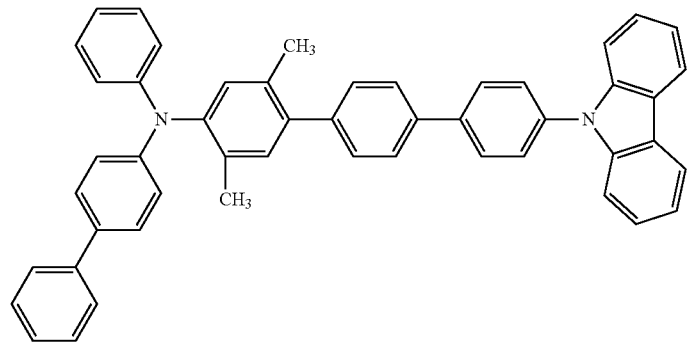
(30)
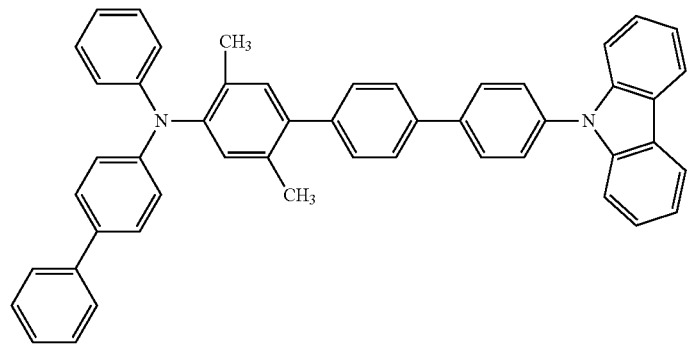
(31)
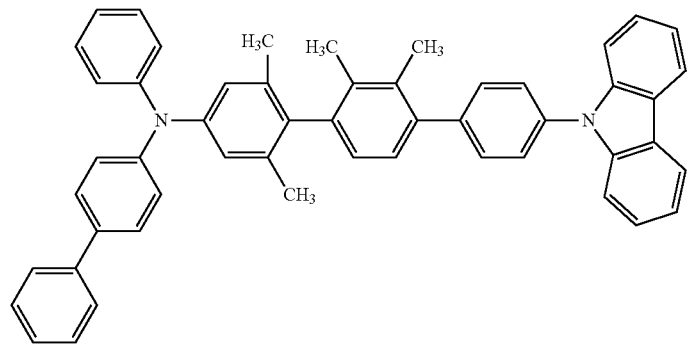
(32)

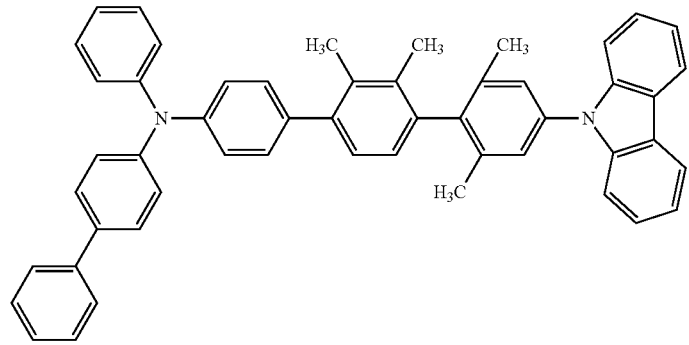
(33)
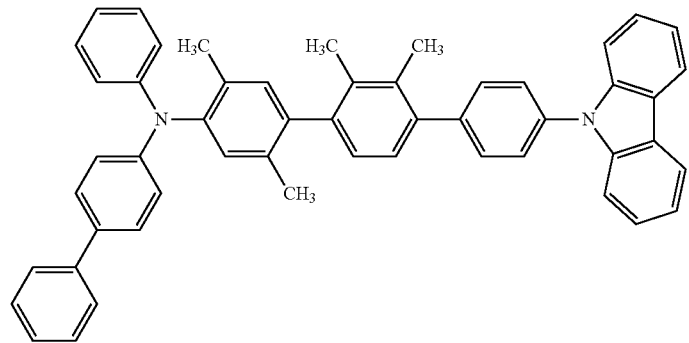
(34)
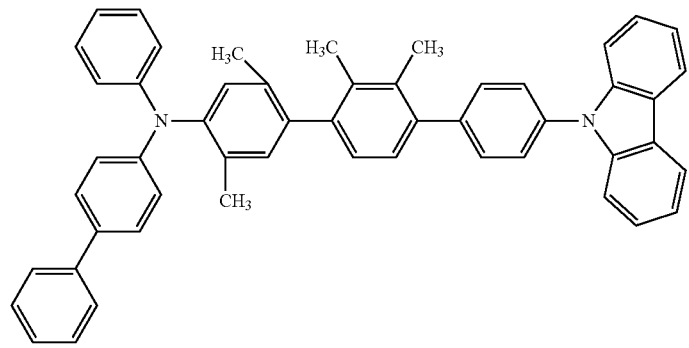
(35)
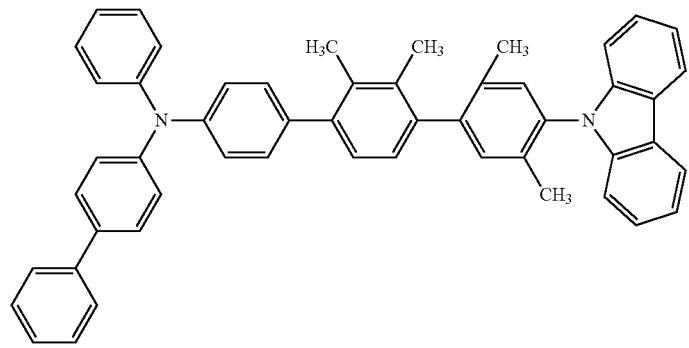
(36)

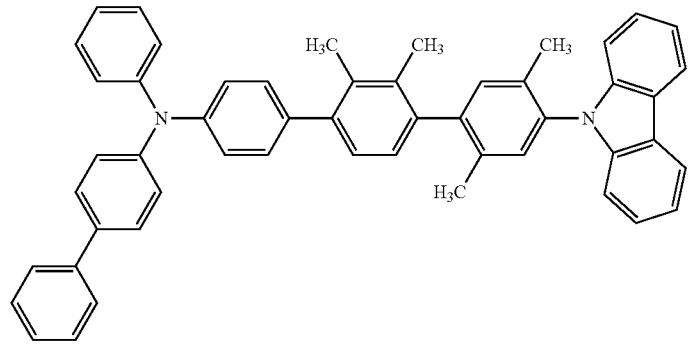
(37)
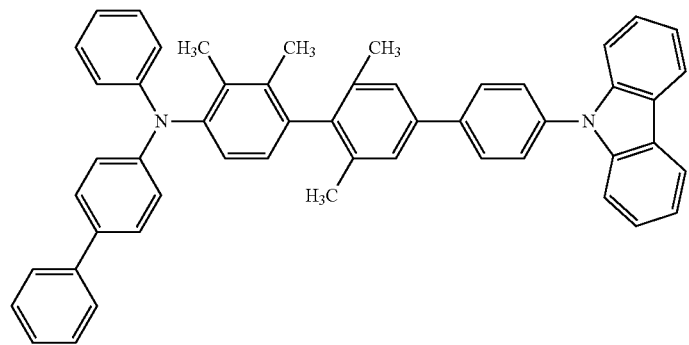
(38)
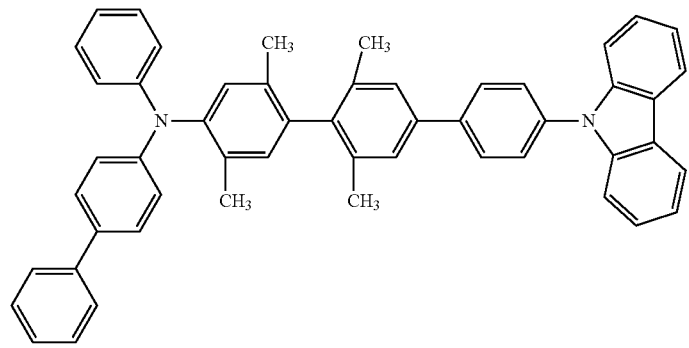
(39)
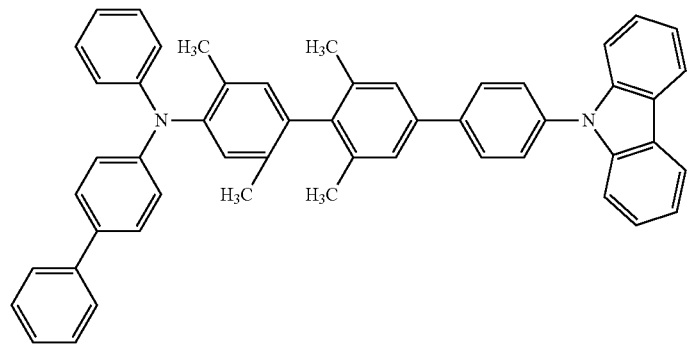
(40)

-continued
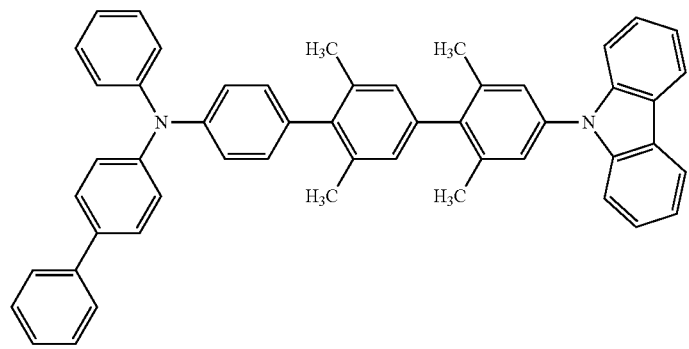
(41)
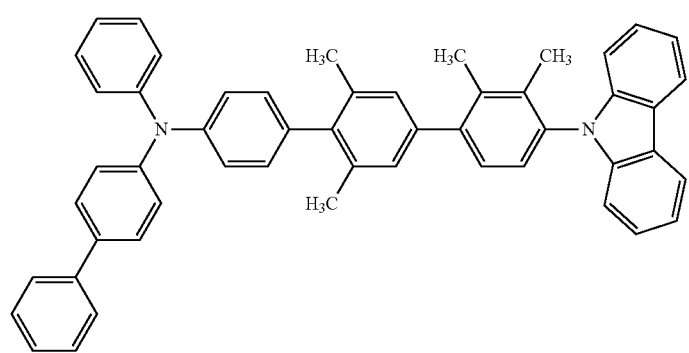
(42)
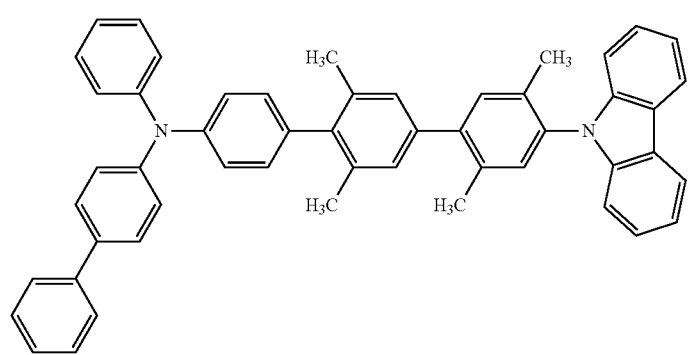
(43)
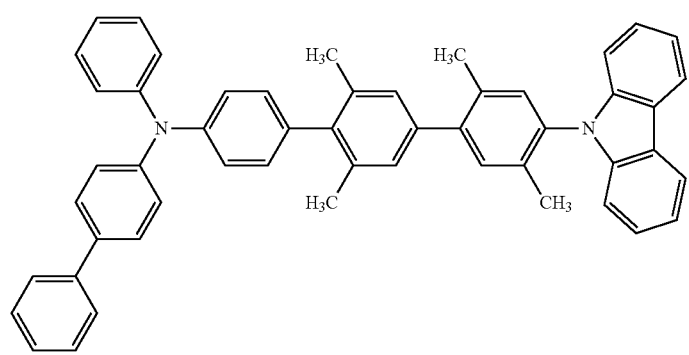
(44)

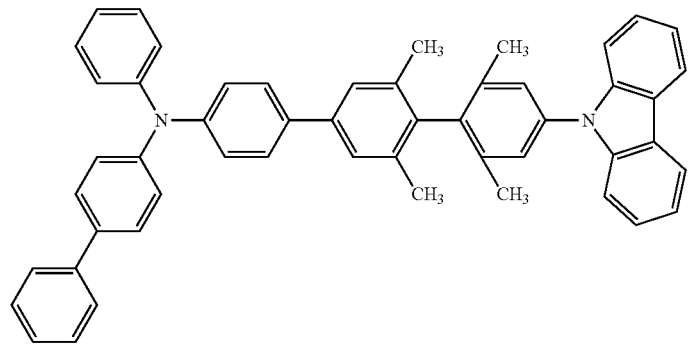
(45)
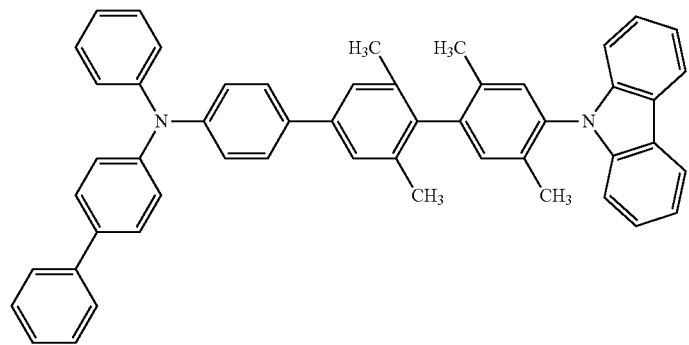
(46)
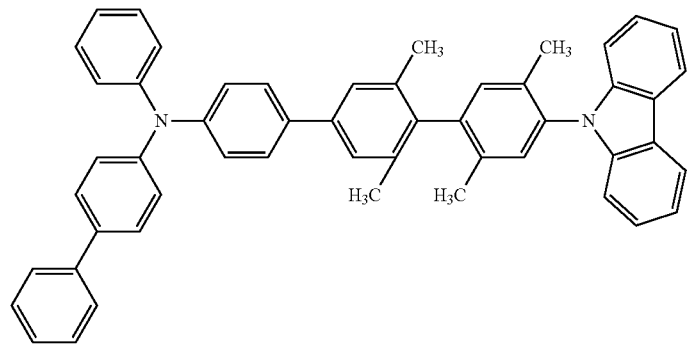
(47)
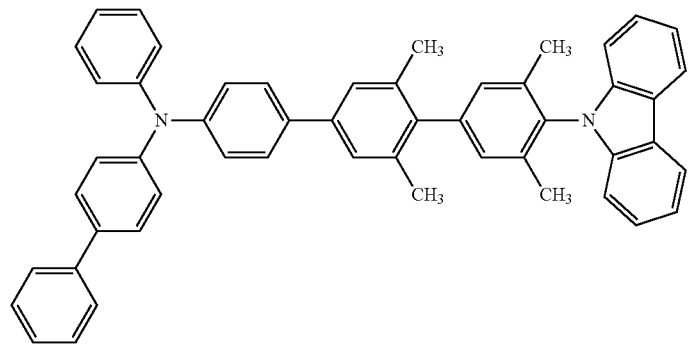
(48)

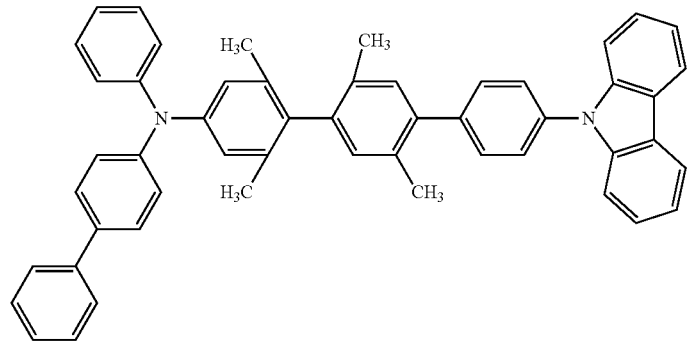
(49)
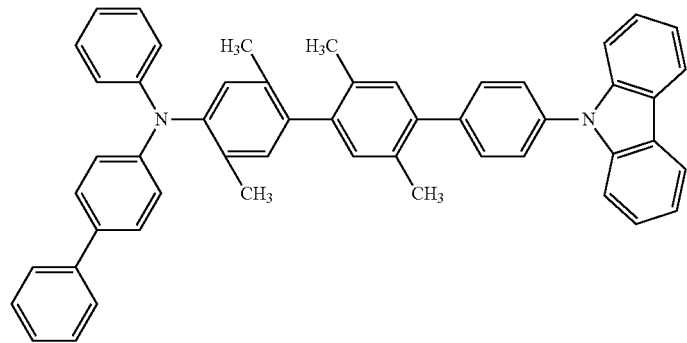
(50)
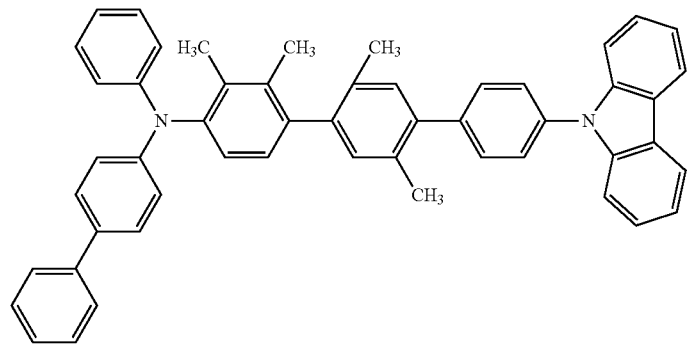
(51)
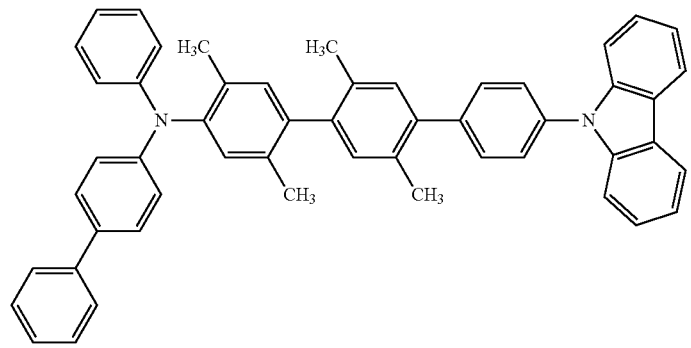
(52)

-continued
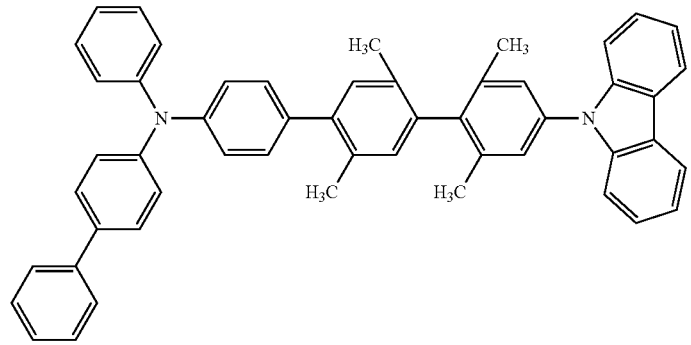
(53)
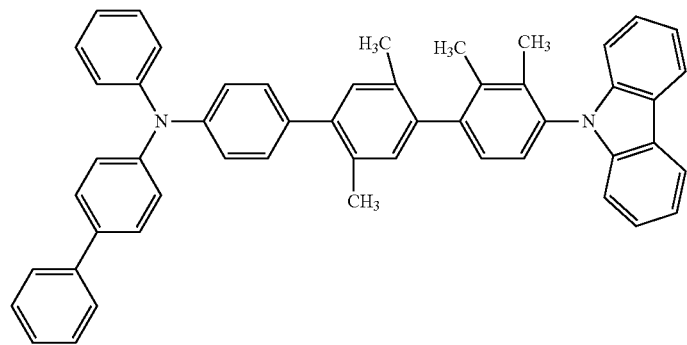
(54)
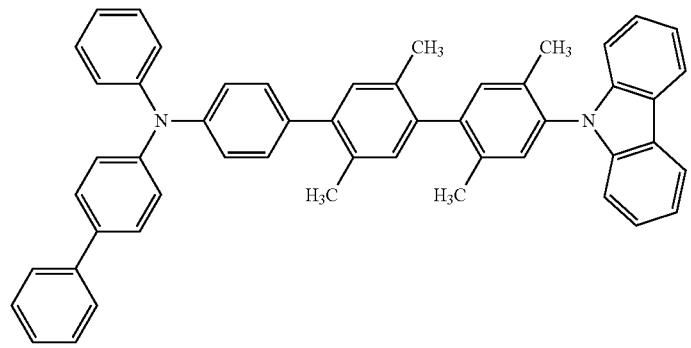
(55)
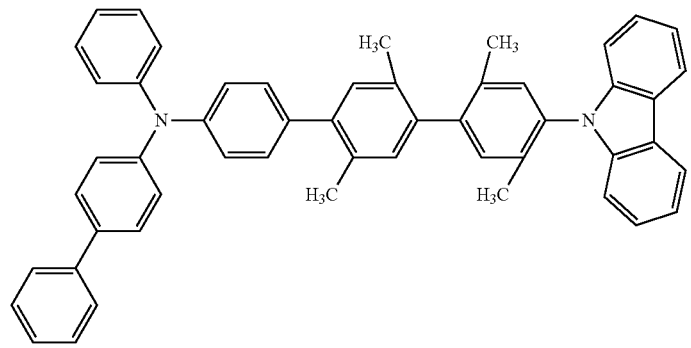
(56)

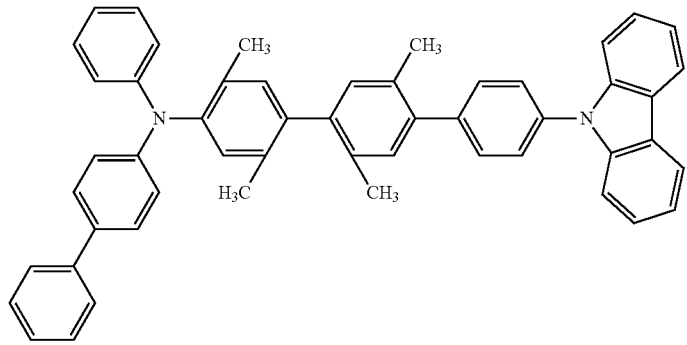
(57)
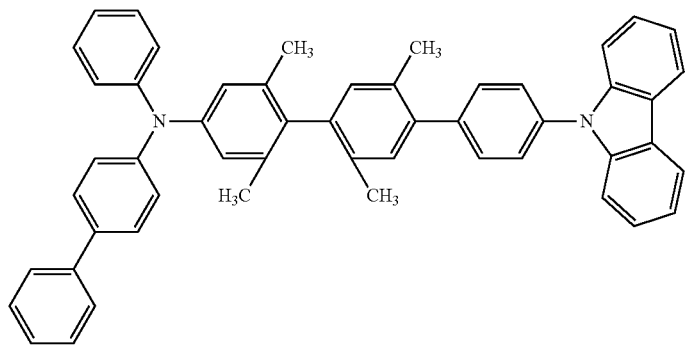
(58)
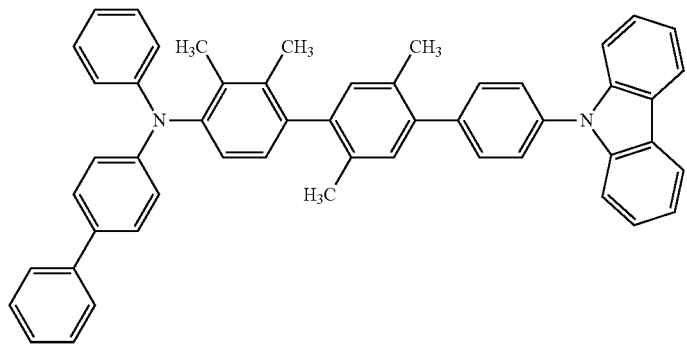
(59)
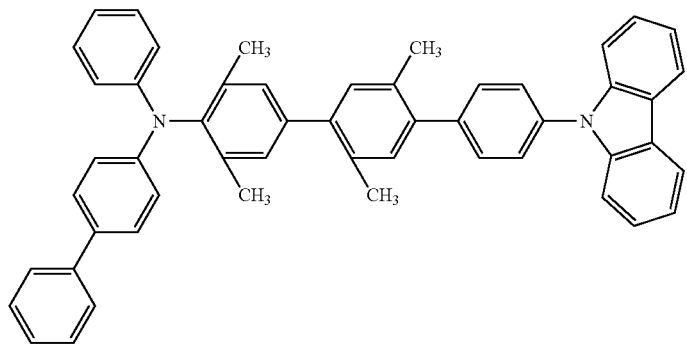
(60)

-continued
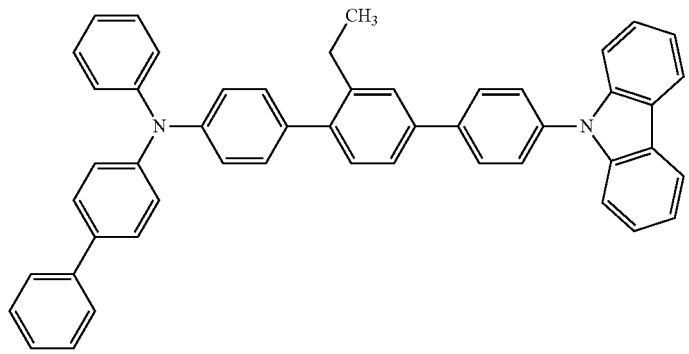
(61)
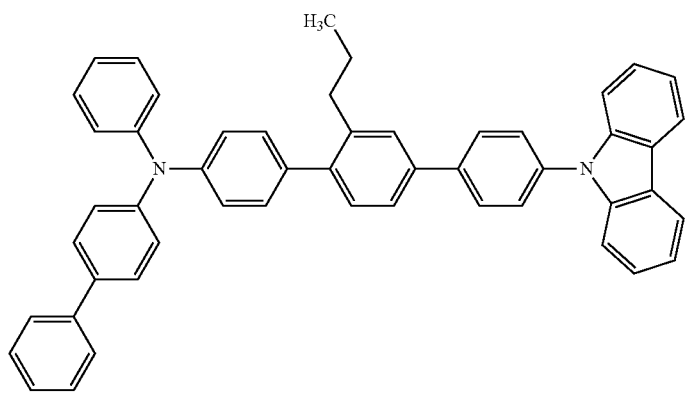
(62)
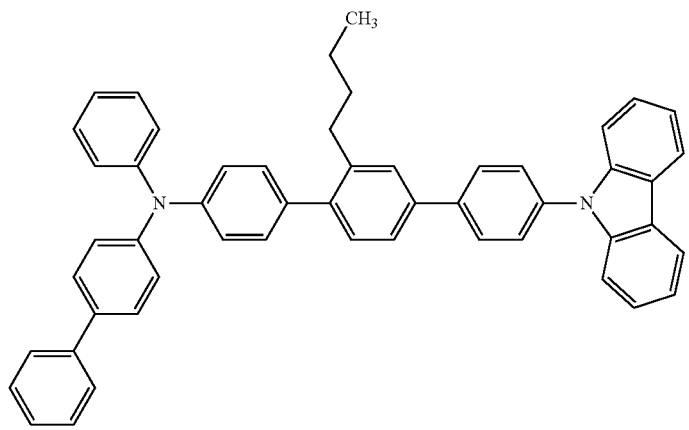
(63)
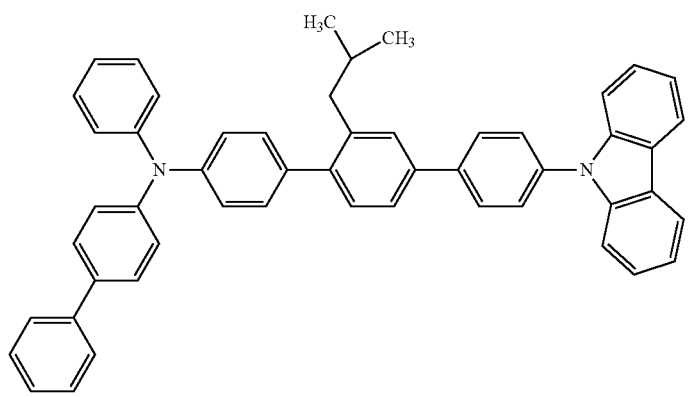
(64)

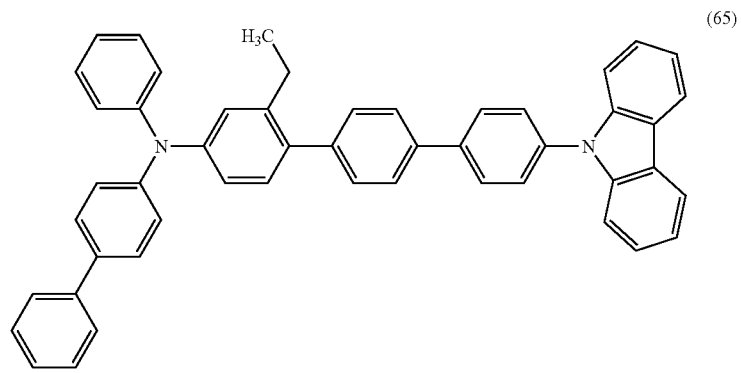
(65)
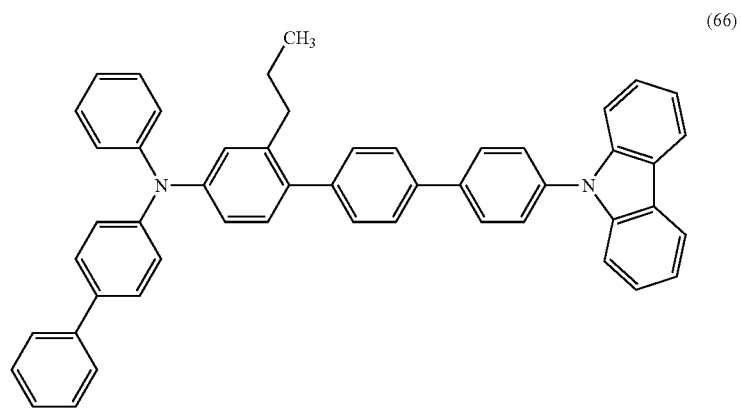
(66)
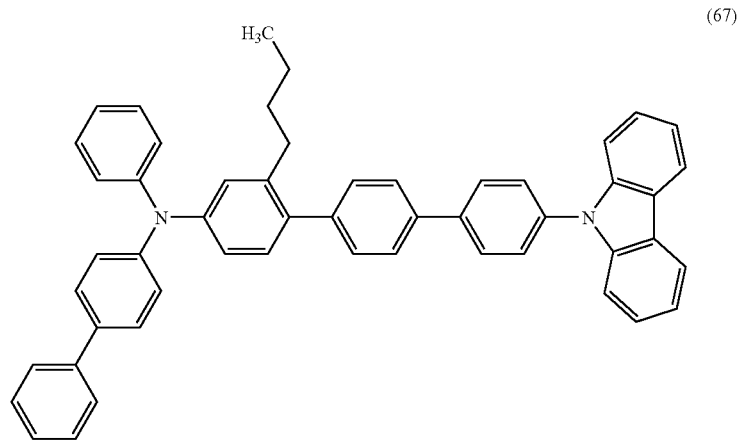
(67)
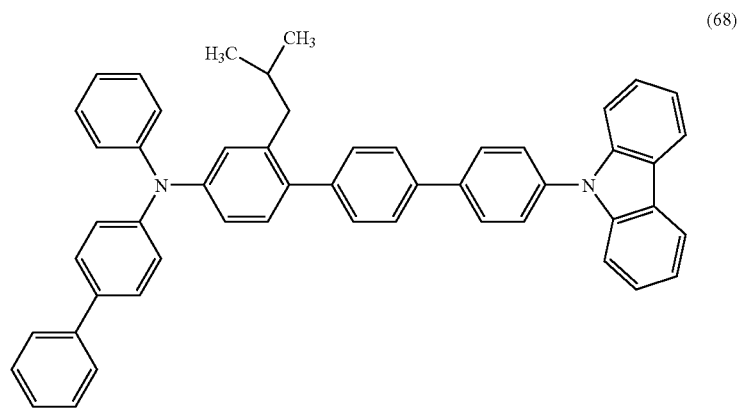
(68)

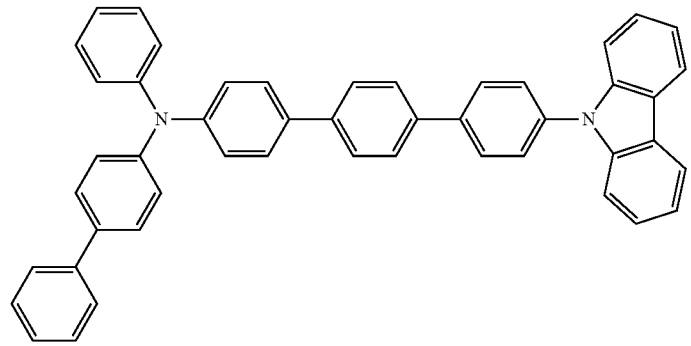
(69)
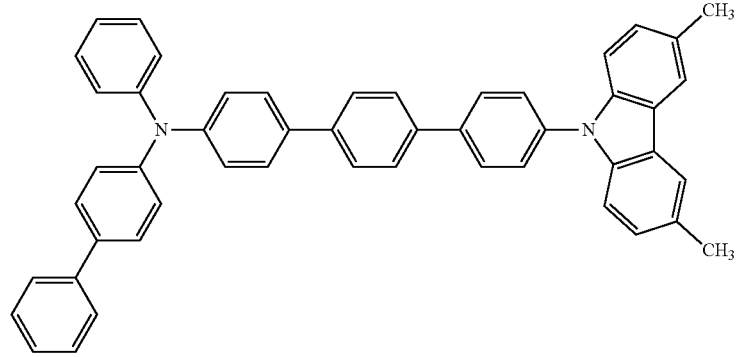
(70)
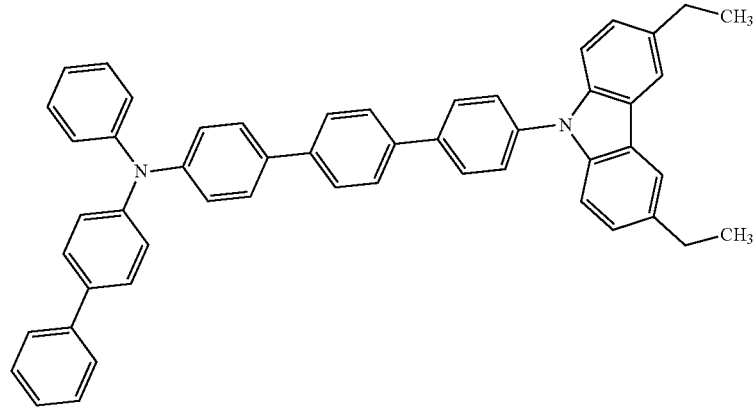
(71)
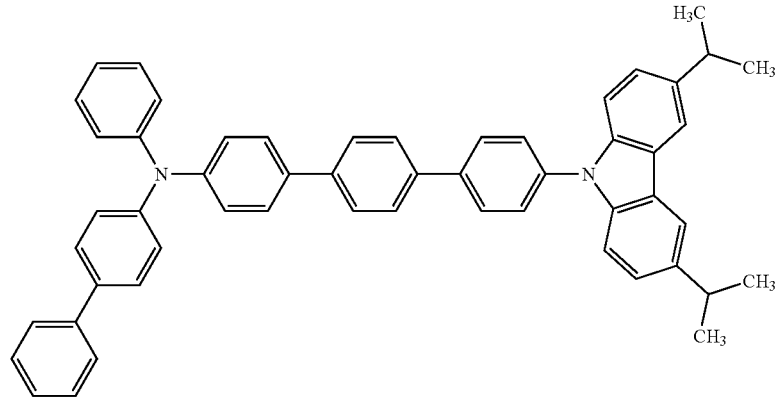
(72)

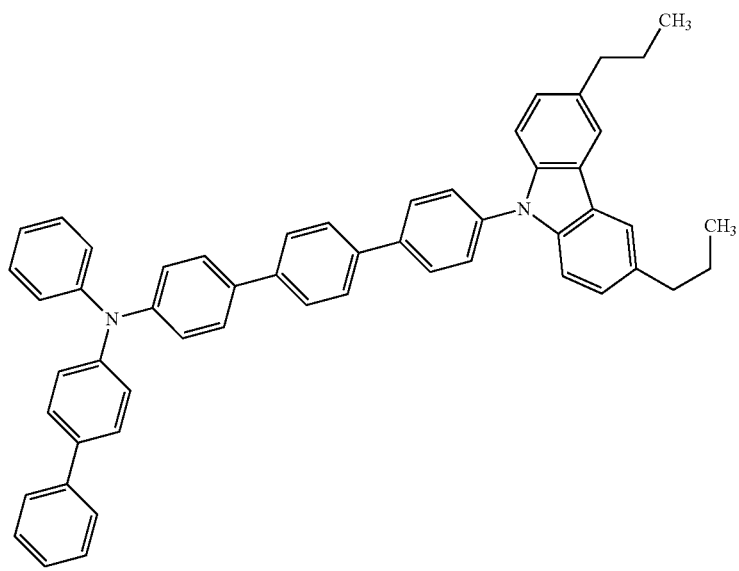
(73)
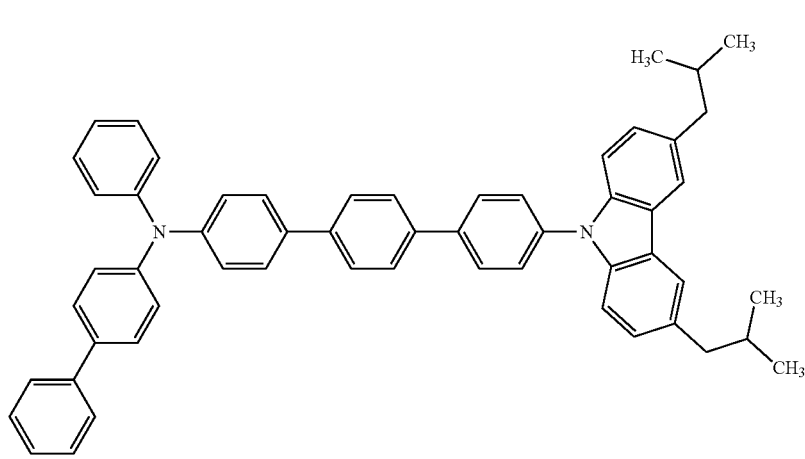
(74)
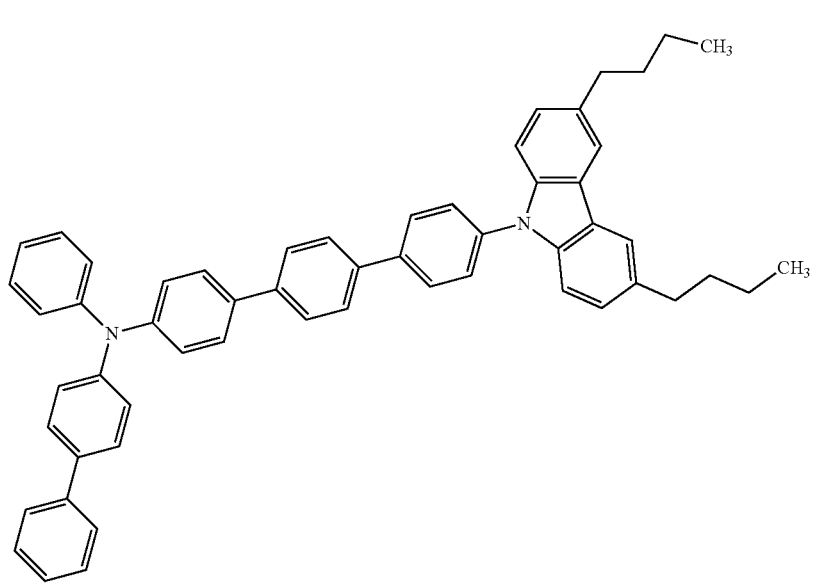
(75)

-continued
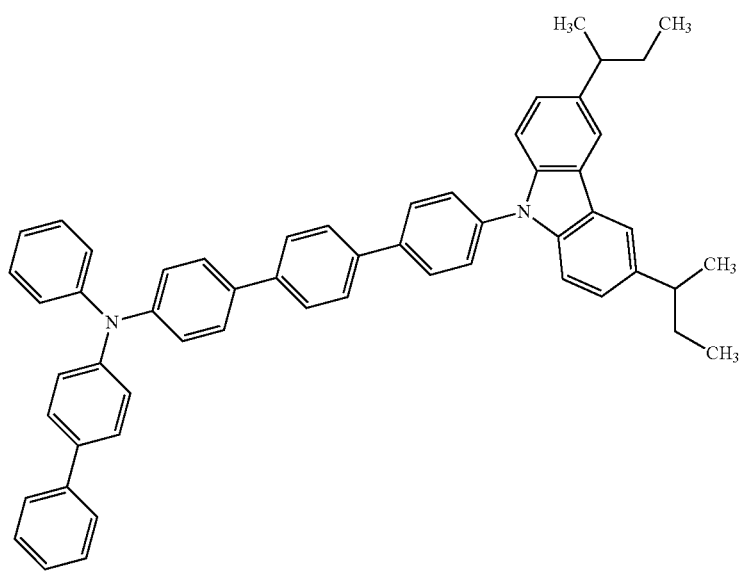
(76)
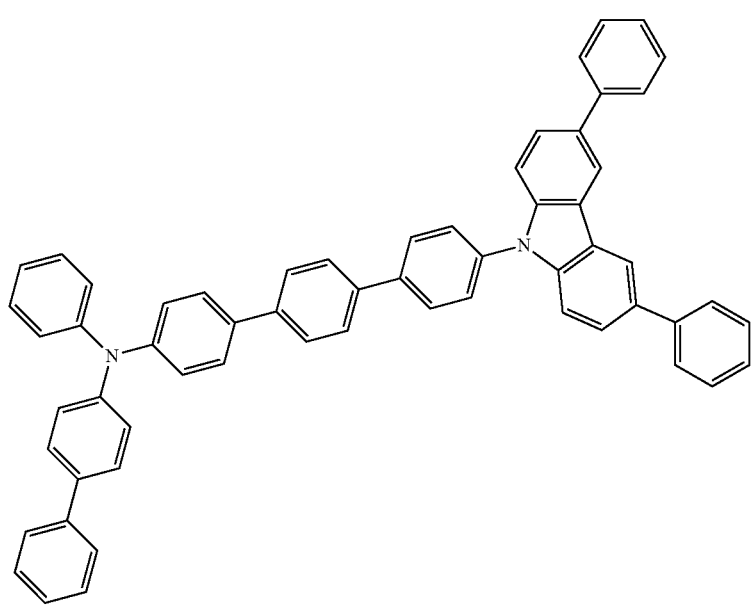
(77)
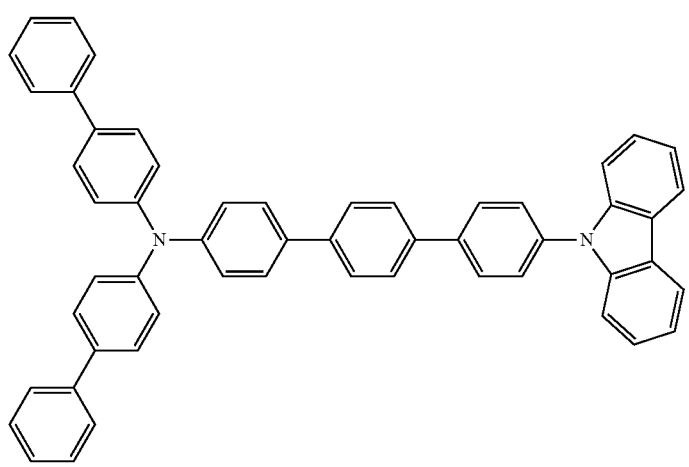
(78)

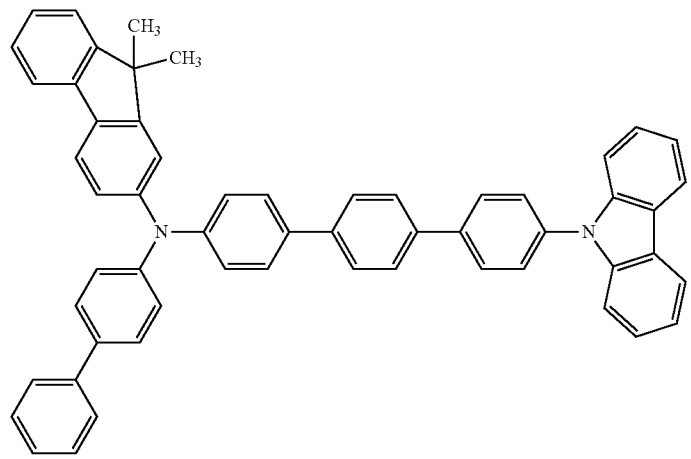
(79)
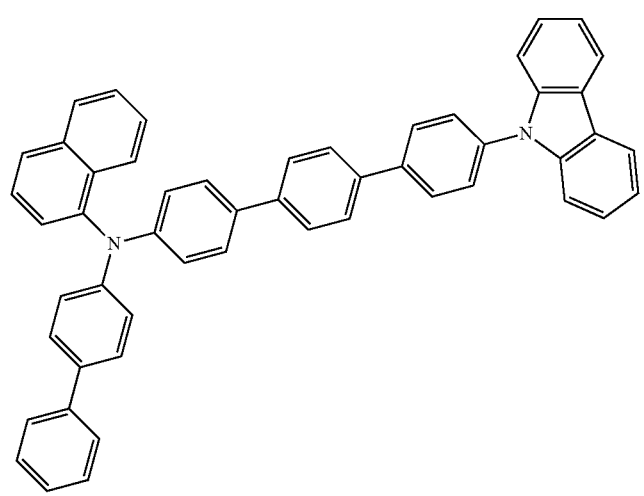
(80)
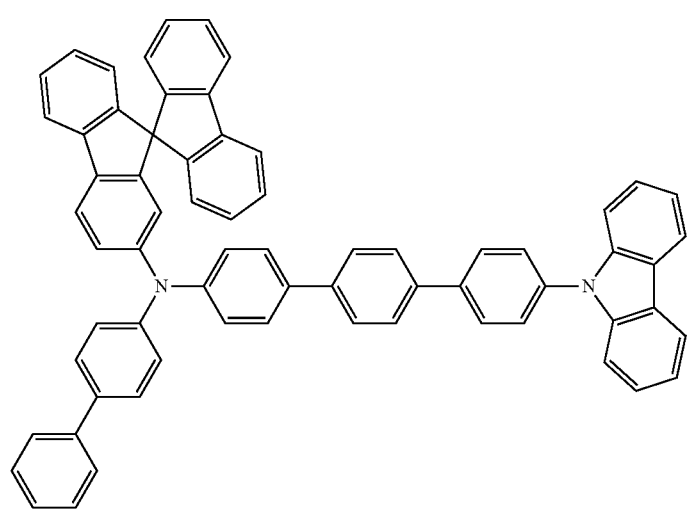
(81)

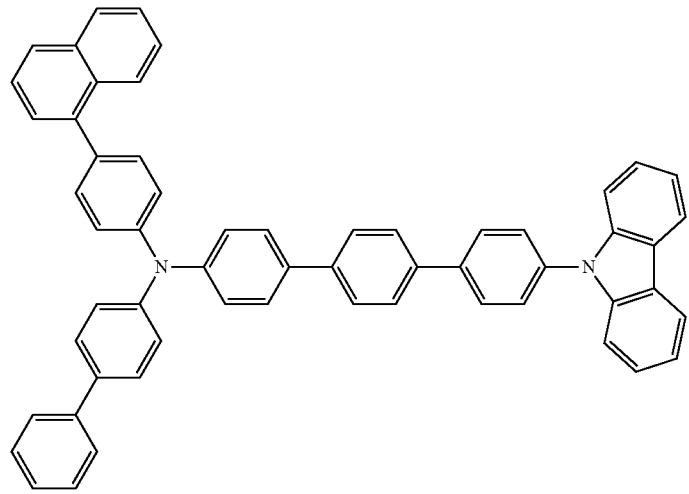
(82)
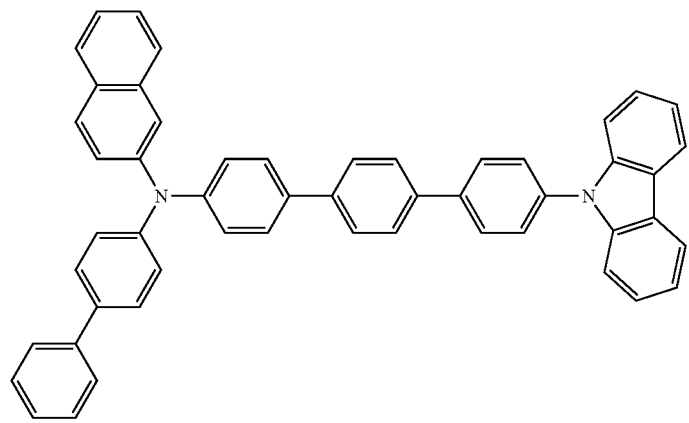
(83)
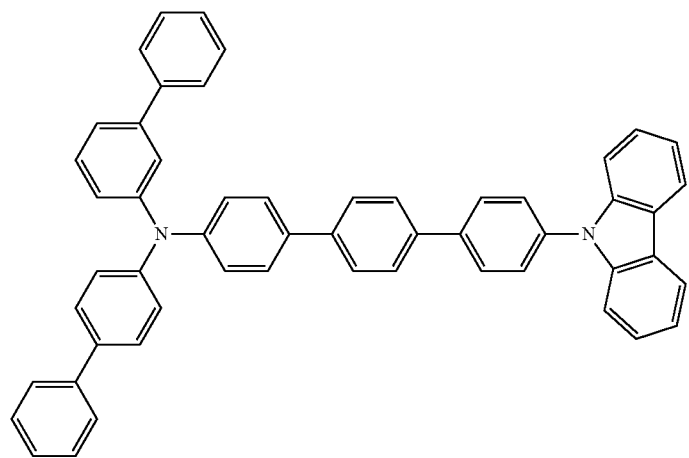
(84)

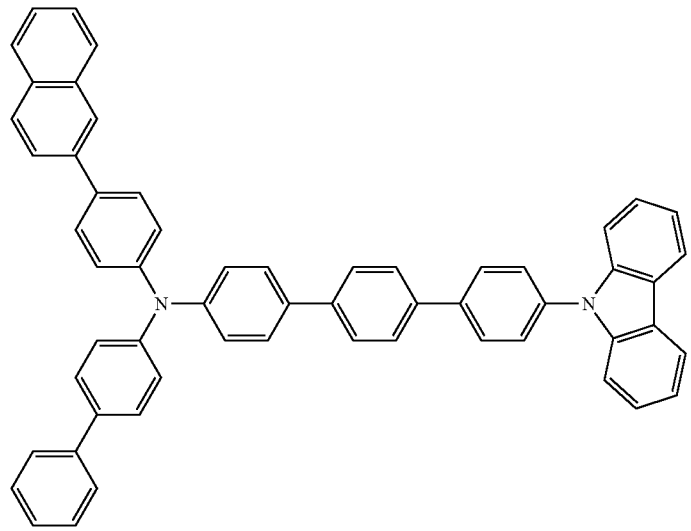
(85)
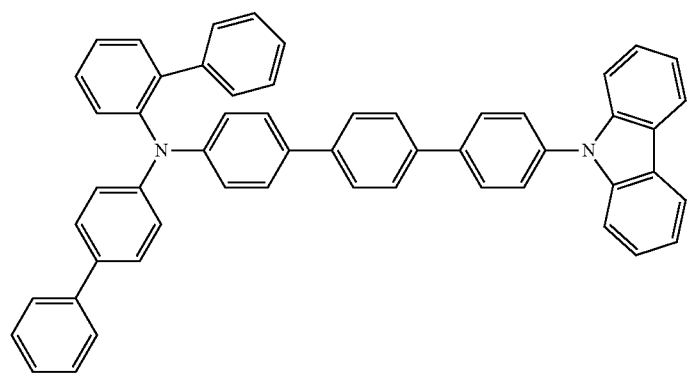
(86)
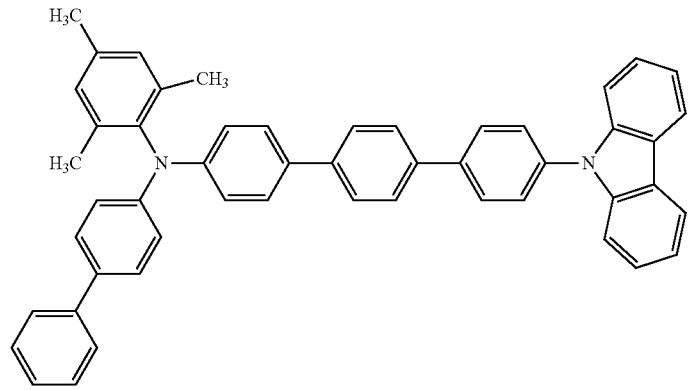
(87)

(88)
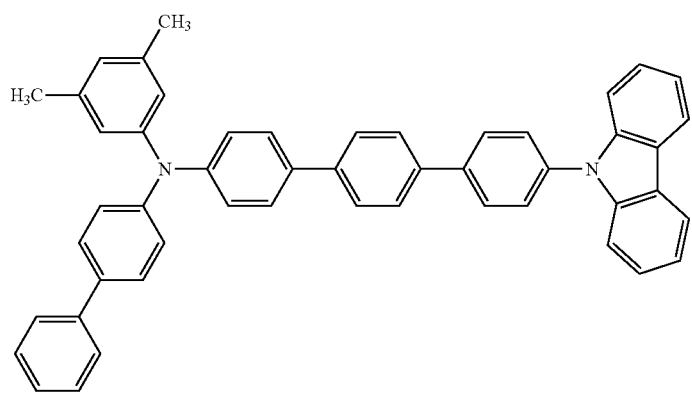
(89)
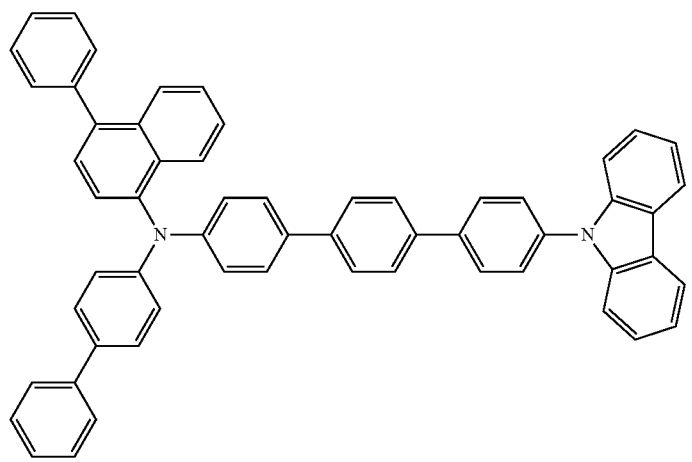
(90)
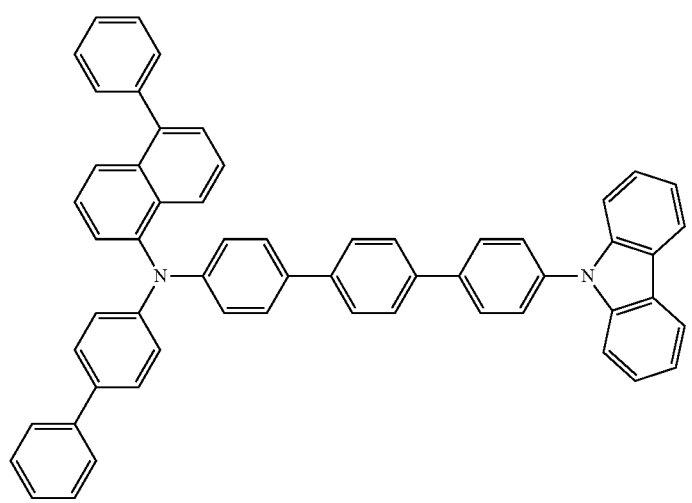
(91)
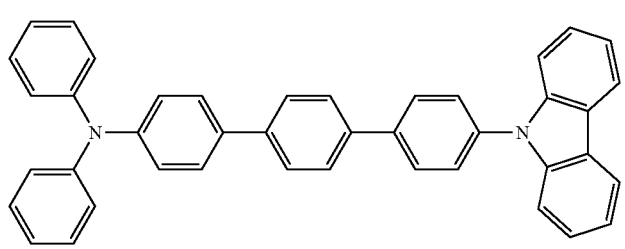

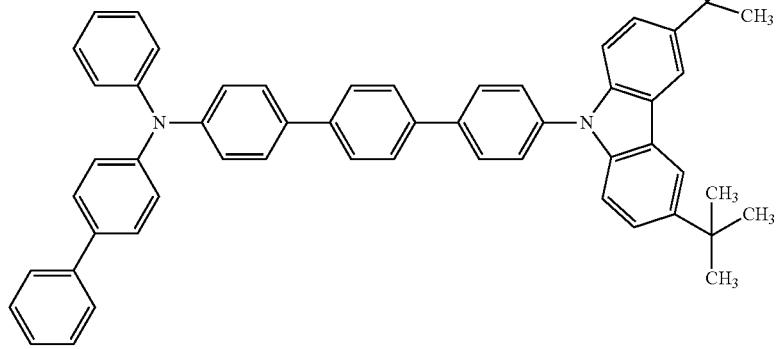
(92)
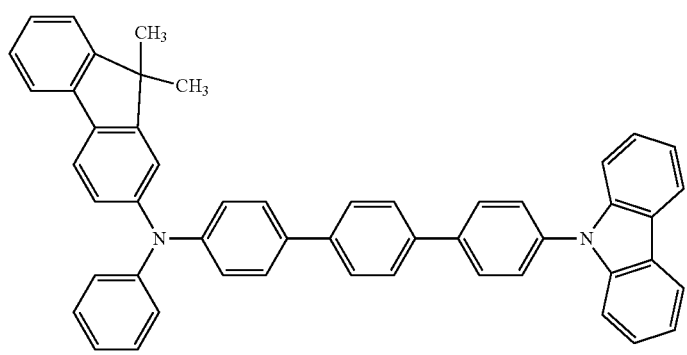
(93)
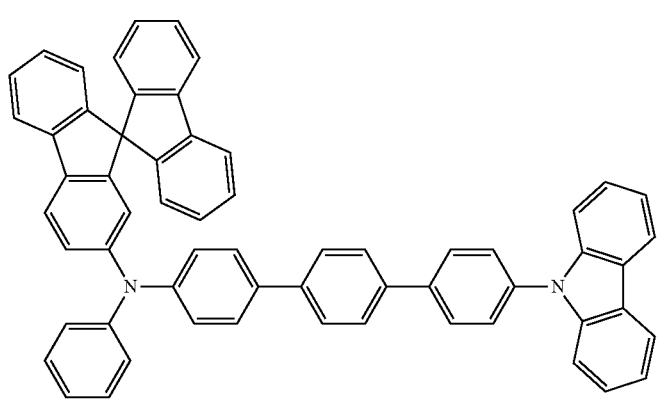
(94)
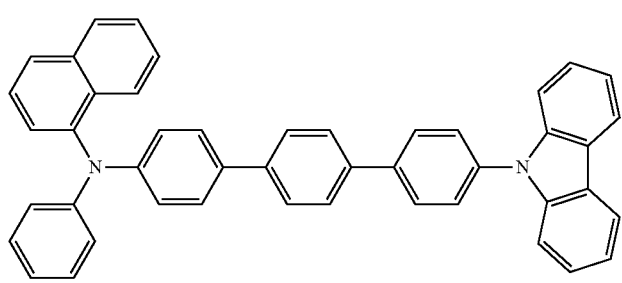
(95)

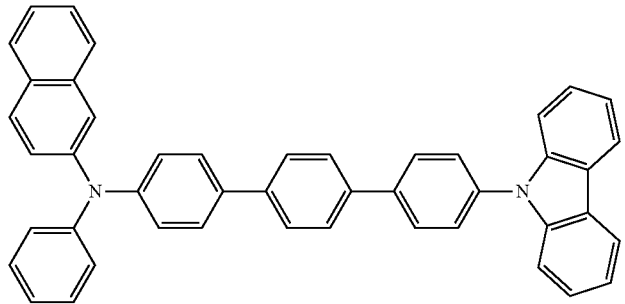
(96)
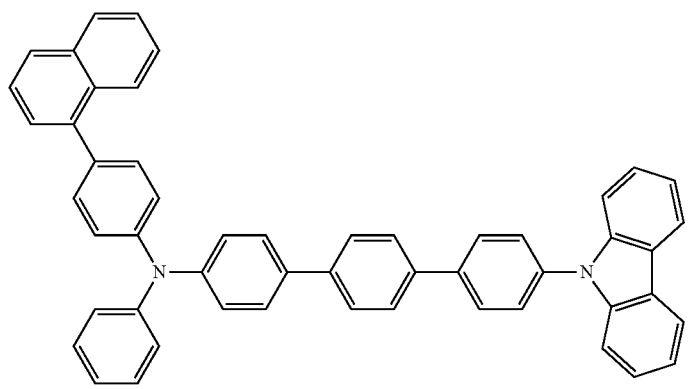
(97)
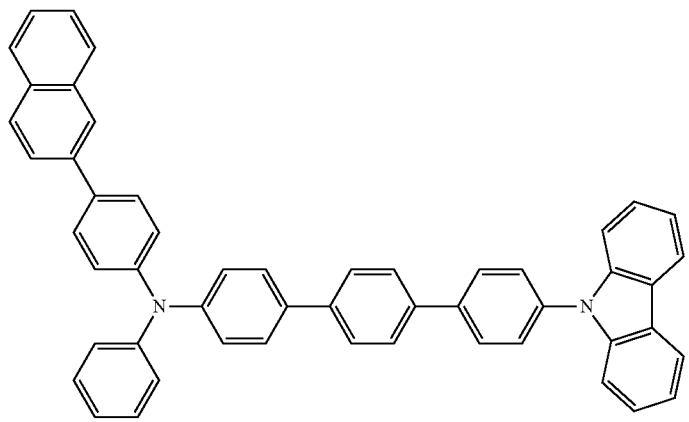
(98)
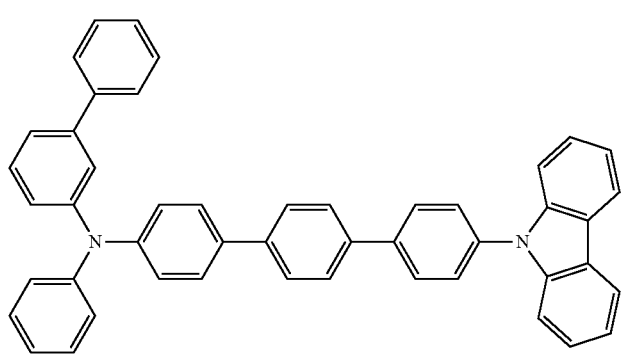
(99)

-continued
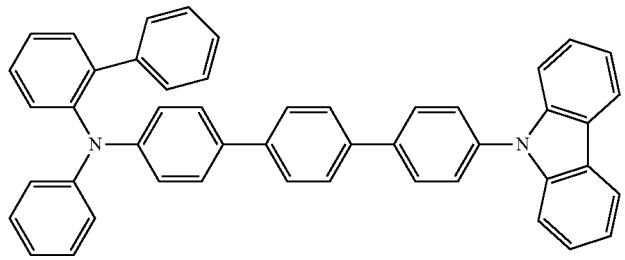
(100)
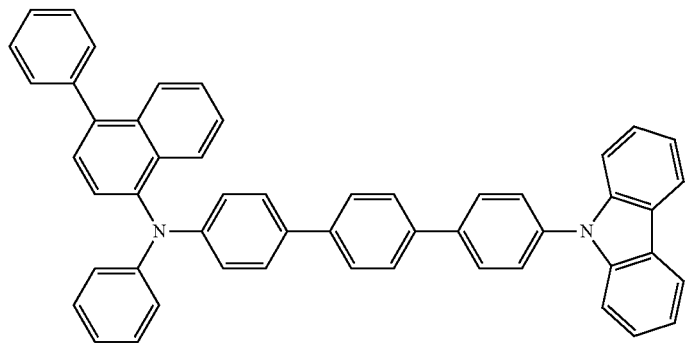
(101)
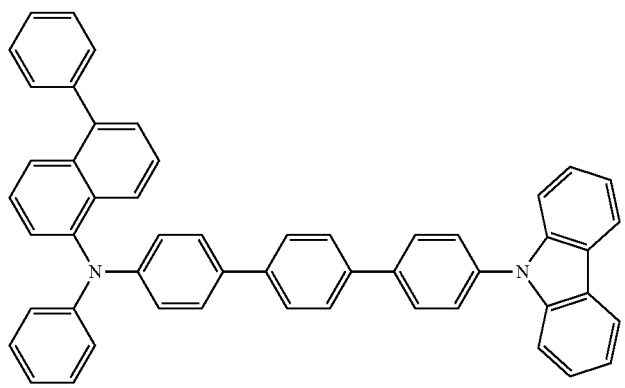
(102)
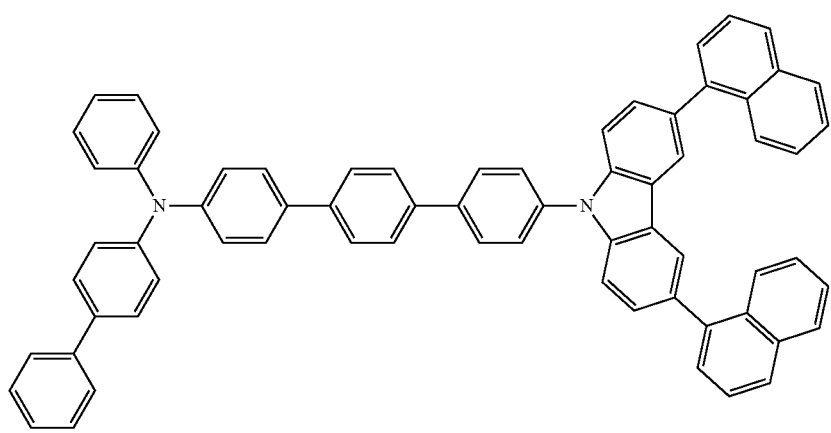
(103)

(104)
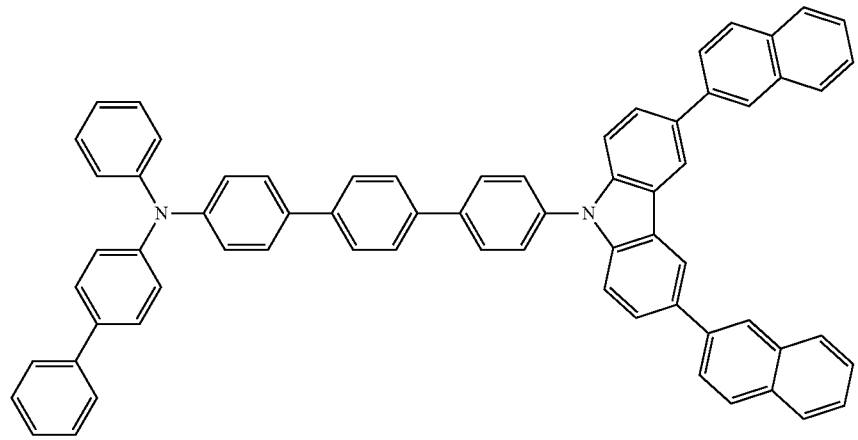
(105)
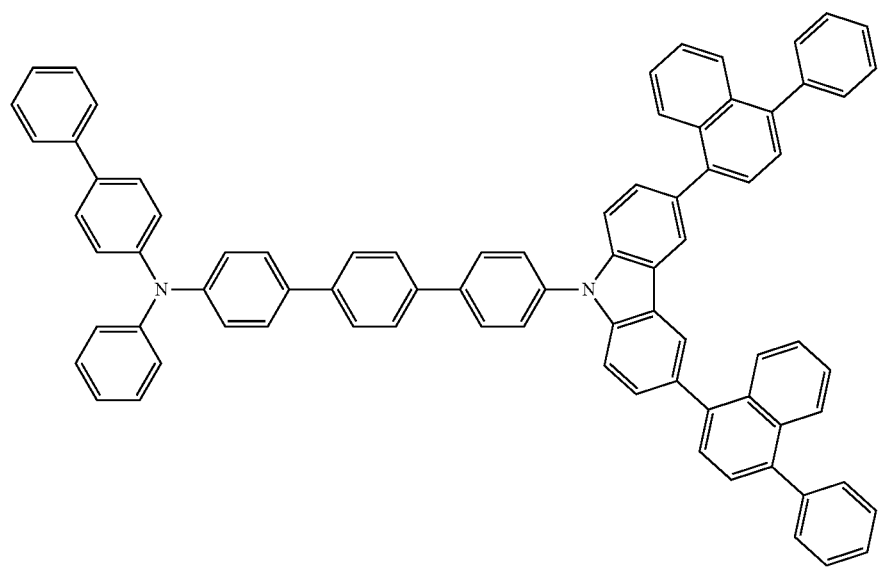
(106)
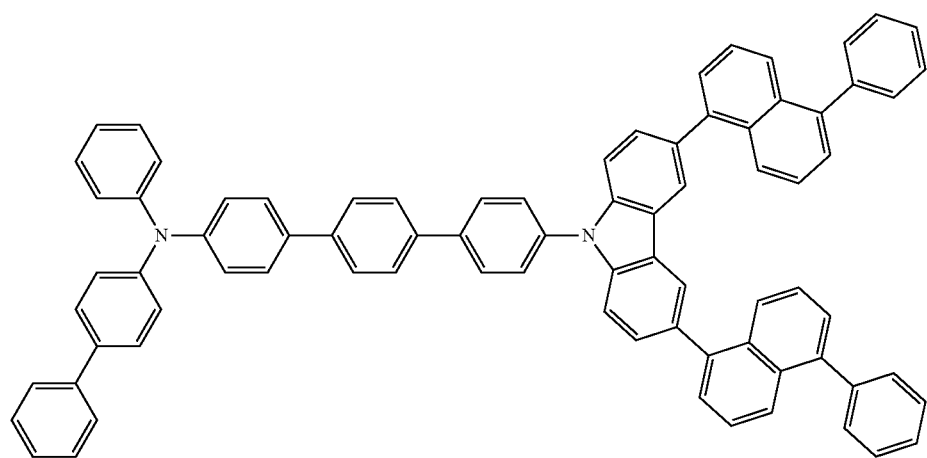

(107)
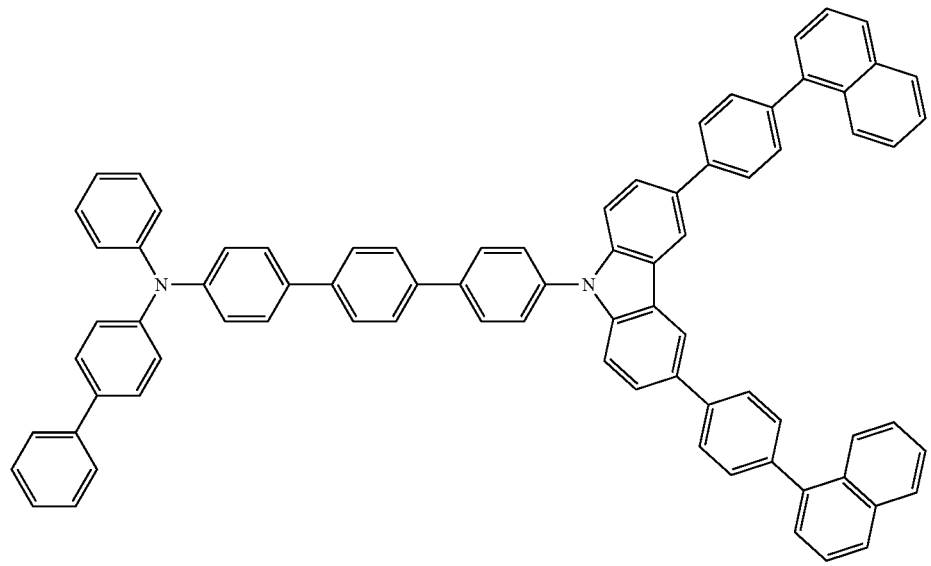
(108)
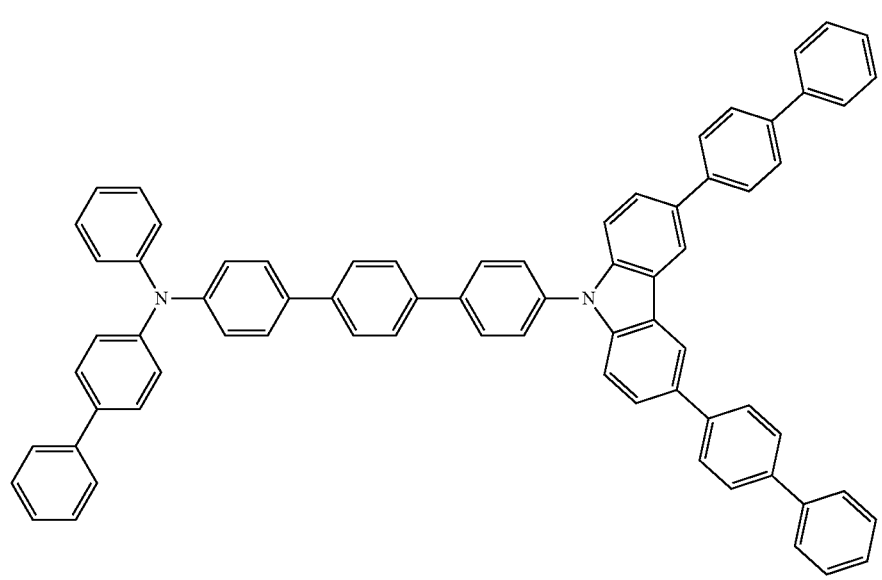

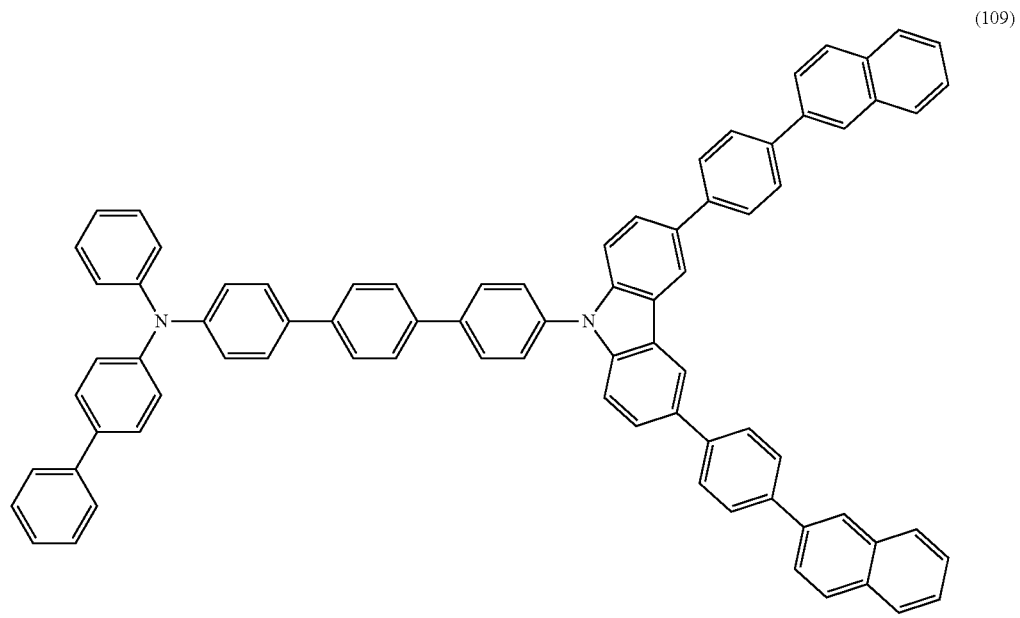
(109)
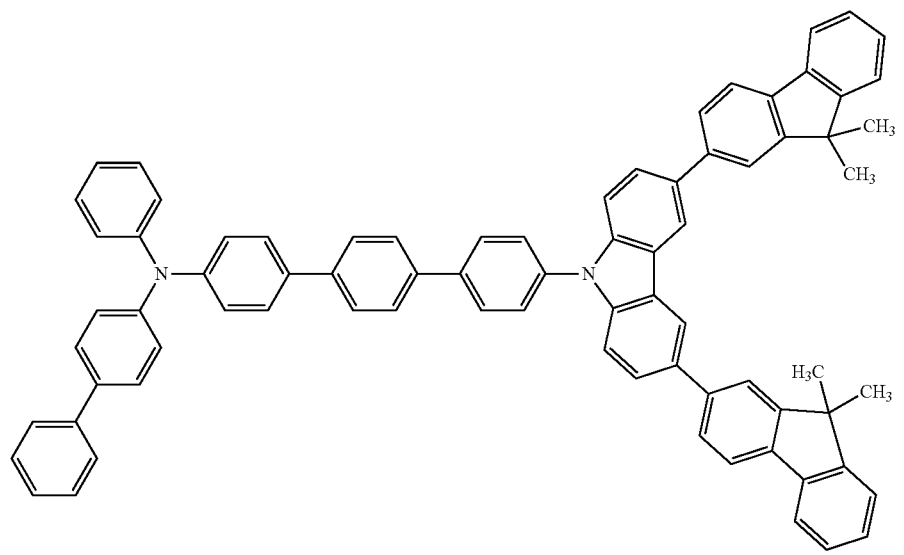
(110)

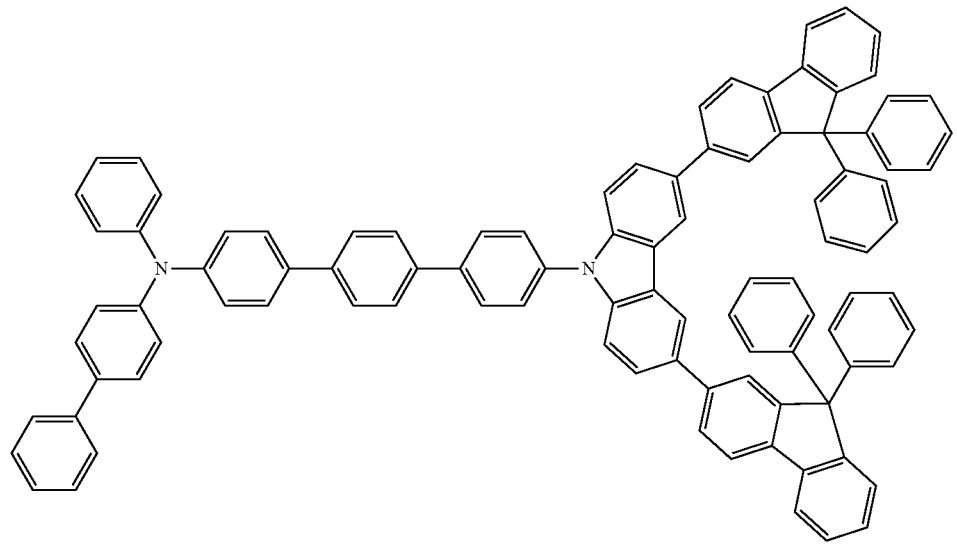
(111)
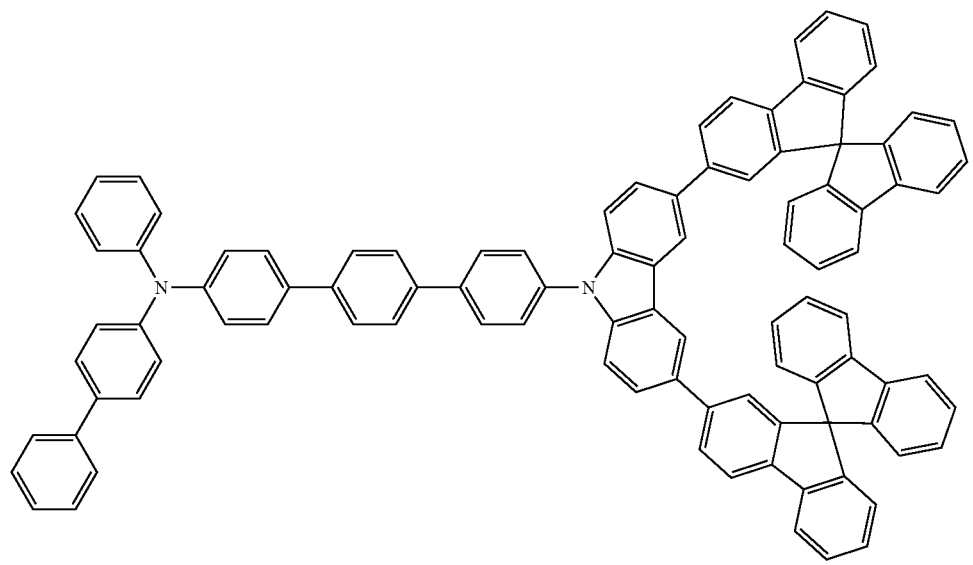
(112)
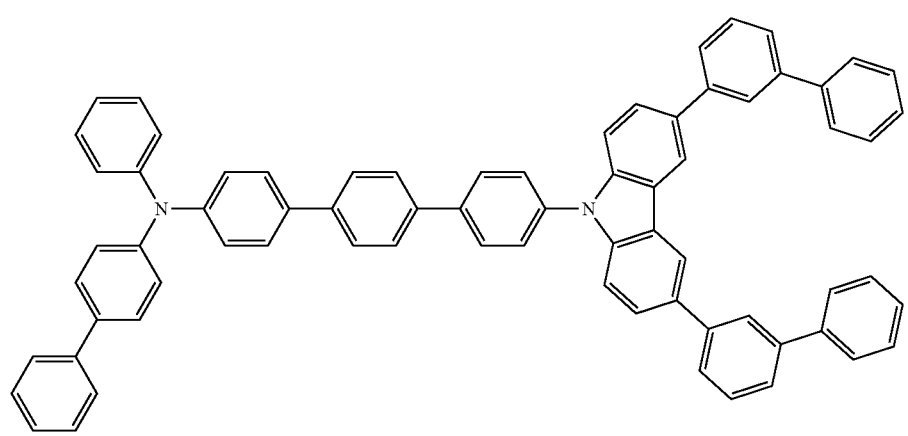
(113)

-continued
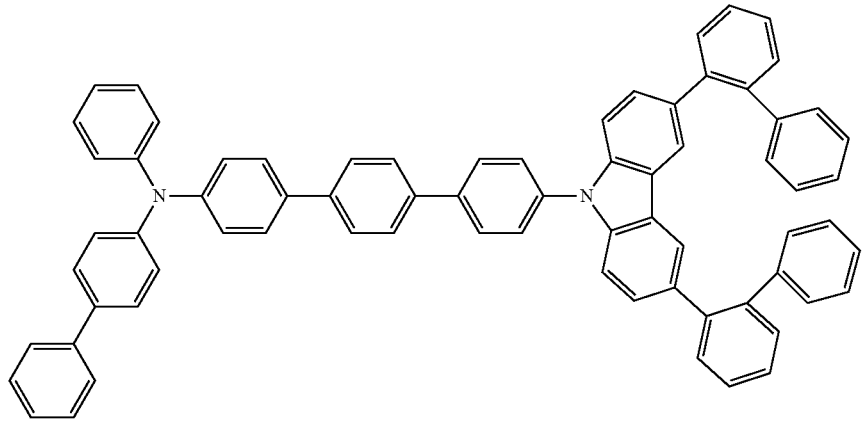
(114)
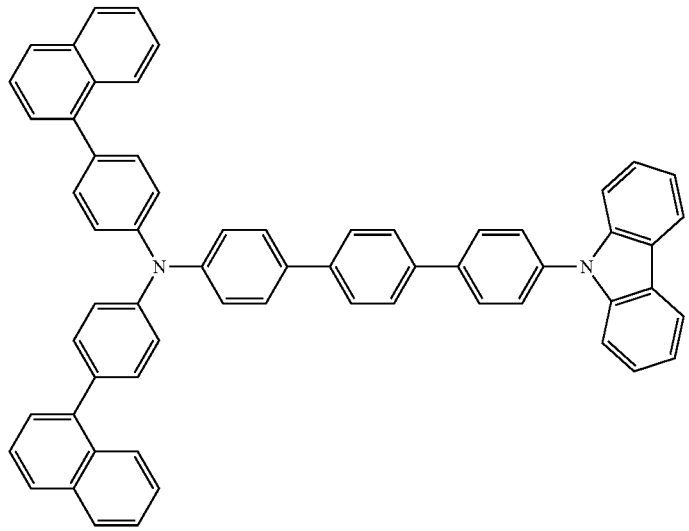
(115)
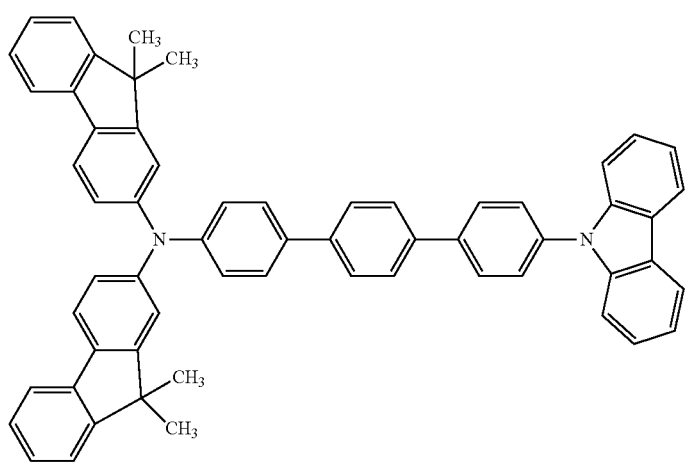
(116)

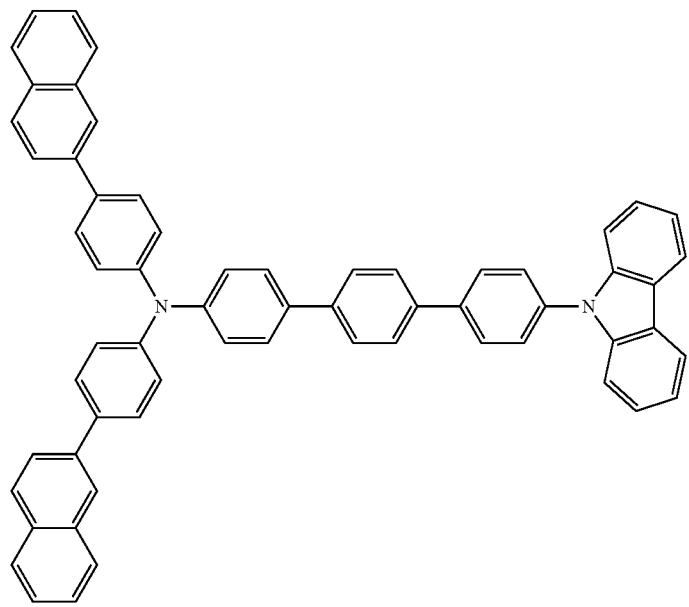
(117)
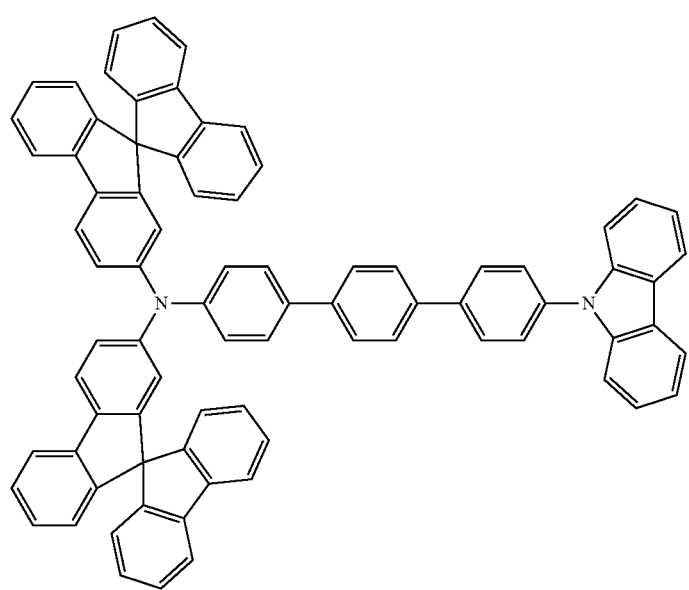
(118)

The aromatic amine compound in this embodiment represented by the general formula (1) can be synthesized by a synthesis method shown in a synthesis scheme (A-1) and synthesis schemes (B-1) to (B-3).

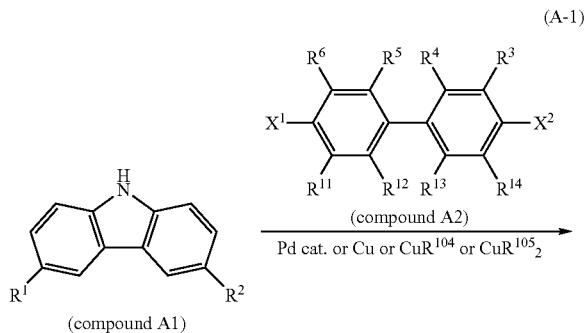

(A-1)

(compound A1)

(compound A2)

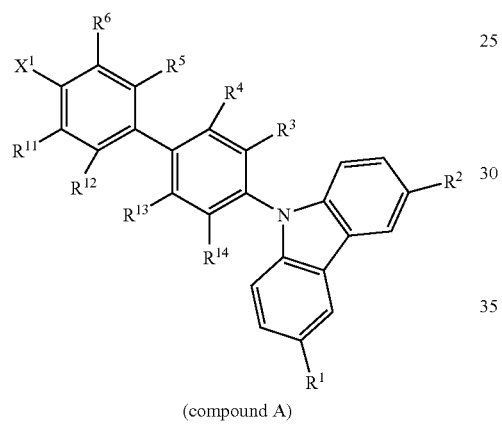

(compound A)

First, a 9-aryl-9H-carbazole compound that is halogenated (Compound A) is synthesized. As shown in the synthesis scheme (A-1), the compound A can be obtained in such a manner that a 9H-carbazole compound (Compound A1) and a dihalogenated aryl compound (Compound A2) are coupled in the presence of a base through a Hartwig-Buchwald reaction using a palladium catalyst or through an Ullmann reaction using copper or a copper compound.

In the synthesis scheme (A-1), $R^1$ and $R^2$ are independently a hydrogen atom, an alkyl group having 1 to 4 carbon atoms, or an aryl group having 6 to 13 carbon atoms. The aryl group having 6 to 13 carbon atoms may further have a substituent and substituents of the aryl group may be bound to each other to form a ring. In addition, $R^3$ to $R^6$ and $R^{11}$ and $R^{14}$ are independently a hydrogen atom or an alkyl group having 1 to 4 carbon atoms. Furthermore, $X^1$ and $X^2$ are independently a halogen or a triflate group, and when $X^1$ and $X^2$ are independently a halogen, chlorine, bromine, and iodine are preferable.

In the case where the Hartwig-Buchwald reaction is performed in the synthesis scheme (A-1), a palladium catalyst that can be used may be, but not limited to, bis(dibenzylideneacetone)palladium(0), palladium(II) acetate, or the like. As a ligand in the palladium catalyst that can be used in the synthesis scheme (A-1), tri(tert-butyl)phosphine, tri(n-hexyl)phosphine, tricyclohexylphosphine, and the like can be given. In the synthesis scheme (A-1), as a base that can be used, an organic base such as sodium tert-butoxide, an inorganic base such as potassium carbonate, or the like can be given. A solvent that can be used in the synthesis scheme (A-1) may be, but not limited to, toluene, xylene, benzene, tetrahydrofuran, or the like.

The case in which the Ullmann reaction is performed in the synthesis scheme (A-1) is described. In the synthesis scheme (A-1), $R^{104}$ and $R^{105}$ are independently a halogen, an acetoxy group, or the like, and as the halogen, chlorine, bromine, or iodine can be used. Further, copper(I) iodide where $R^{104}$ is iodine or copper(II) acetate where $R^{105}$ is an acetoxy group is preferable. The copper compound used for the reaction is not limited thereto. Further, copper can be used other than the copper compound. A base that can be used in the synthesis scheme (A-1) may be, but not limited to, an inorganic base such as potassium carbonate. As a solvent that can be used in the synthesis scheme (A-1), 1,3-dimethyl-3,4,5,6-tetrahydro-2(1H)pyrimidinone (DMPU), toluene, xylene, benzene, and the like can be given. In the Ullmann reaction, the target substance can be obtained in a shorter time and in a higher yield when the reaction temperature is 100° C. or higher; therefore, it is preferable to use DMPU or xylene that has a high boiling point. Because the reaction temperature of 150° C. or higher is preferable, DMPU is more preferably used.

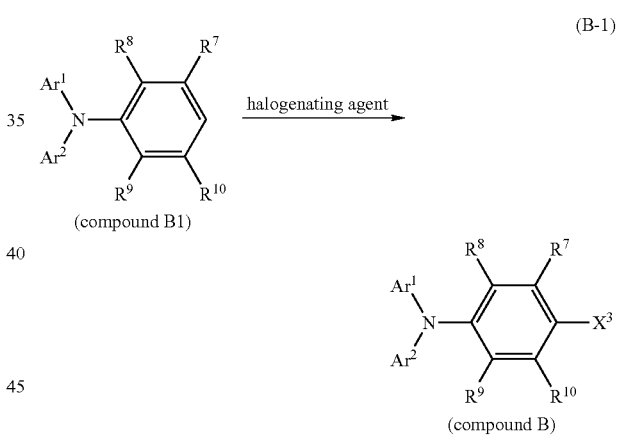

(B-1)

(compound B1)

(compound B)

Next, a halogenated tertiary arylamine compound (Compound B) is synthesized. The halogenated tertiary arylamine compound (Compound B) can be synthesized as shown by the synthesis scheme (B-1). In other words, a tertiary arylamine compound (compound B1) is halogenated by using a halogenating agent, whereby the halogenated tertiary arylamine compound (Compound B) can be obtained. Note that as the halogenating agent, N-bromosuccinimide (NBS), N-iodosuccinimide (NIS), bromine, iodine, potassium iodide, or the like can be used.

In the synthesis scheme (B-1), $R^7$ to $R^{10}$ are independently a hydrogen atom or an alkyl group having 1 to 4 carbon atoms. $Ar^1$ and $Ar^2$ are independently an aryl group having 6 to 13 carbon atoms. The aryl group having 6 to 13 carbon atoms may further have a substituent and substituents of the aryl group may be bound to each other to form a ring. Furthermore, $X^3$ is a halogen or a triflate group, and when $X^3$ is a halogen, chlorine, bromine, and iodine are preferable.

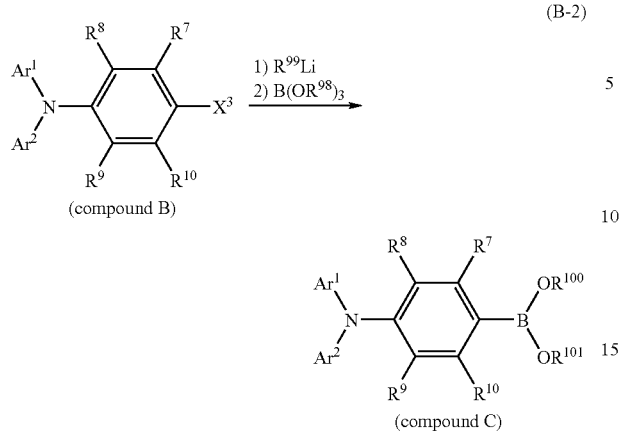

(compound B)

(B-2)

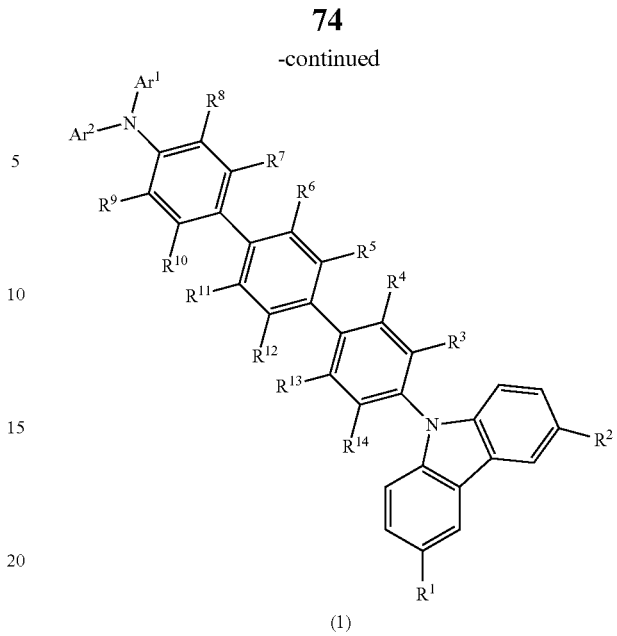

(1)

(compound C)

Next, as shown in the synthesis scheme (B-2), the halogenated tertiary arylamine compound (Compound B) synthesized in the synthesis scheme (B-1) is subjected to a transformation to a boronic acid or an organoboron using an alkyllithium reagent and a boron reagent, whereby a tertiary amine boronic acid or a compound in which the para position of the tertiary amine compound is substituted by organoboron (Compound C) can be obtained. In addition, n-butyllithium, methyllithium, or the like can be used as the alkyllithium reagent. Trimethyl borate, isopropyl borate, or the like can be used as the boron reagent.

In the above synthesis scheme (B-2), $Ar^1$ and $Ar^2$ are independently an aryl group having 6 to 13 carbon atoms. The aryl group having 6 to 13 carbon atoms may further have a substituent and substituents of the aryl group may be bound to each other to form a ring. In addition, $R^7$ to $R^{10}$ are independently a hydrogen atom or an alkyl group having 1 to 4 carbon atoms. Furthermore, $X^3$ is a halogen or a triflate group, and when $X^3$ is a halogen, chlorine, bromine, and iodine are preferable. $R^{98}$ and $R^{99}$ are independently an alkyl group having 1 to 6 carbon atoms. In addition, $R^{100}$ and $R^{101}$ are independently hydrogen or an alkyl group having 1 to 6 carbon atoms. $R^{100}$ and $R^{101}$ may be bound to each other to form a ring.

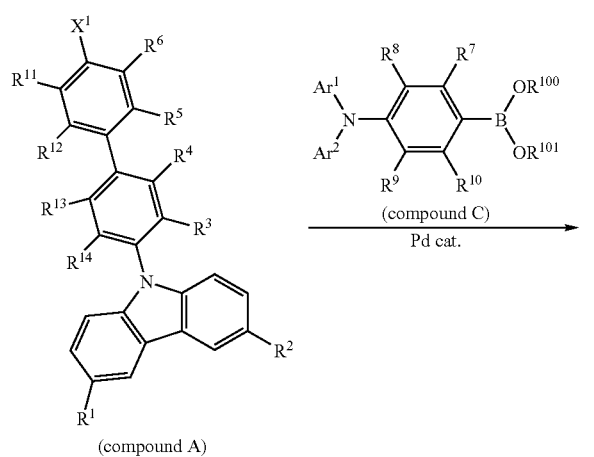

(compound A)

(B-3)

Next, as shown in the synthesis scheme (B-3), the 9-aryl-9H-carbazole compound that is halogenated (Compound A) and the tertiary arylamine boronic acid or the compound in which the tertiary arylamine compound is substituted by organoboron (Compound C) are coupled in the presence of a base by Suzuki-Miyaura Coupling using a palladium catalyst, so that the aromatic amine compound in this embodiment represented by the general formula (1) can be obtained.

In the synthesis scheme (B-3), $R^1$ and $R^2$ are independently a hydrogen atom, an alkyl group having 1 to 4 carbon atoms, or an aryl group having 6 to 13 carbon atoms. In addition, $R^3$ to $R^{14}$ are independently a hydrogen atom or an alkyl group having 1 to 4 carbon atoms. $Ar^1$ and $Ar^2$ are independently an aryl group having 6 to 13 carbon atoms. The aryl group having 6 to 13 carbon atoms may further have a substituent and substituents of the aryl group may be bound to each other to form a ring. $X^1$ is a halogen or a triflate group, and when $X^1$ is a halogen, chlorine, bromine, and iodine are preferable. $R^{100}$ and $R^{101}$ are independently hydrogen or an alkyl group having 1 to 6 carbon atoms. $R^{100}$ and $R^{101}$ may be bound to each other to form a ring.

In the synthesis scheme (B-3), as examples of a palladium catalyst that can be used, palladium(II) acetate, tetrakis(triphenylphosphine)palladium(0), and the like can be given. In the synthesis scheme (B-3), as examples of a ligand of the palladium catalyst that can be used, tri(ortho-tolyl)phosphine, triphenylphosphine, tricyclohexylphosphine, and the like can be given.

In the synthesis scheme (B-3), as examples of a base that can be used, an organic base such as sodium tert-butoxide, an inorganic base such as potassium carbonate, and the like can be given. In the synthesis scheme (B-3), examples of a solvent that can be used include a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethylene glycol dimethyl ether and water; and the like. Note that use of a mixed solvent of toluene and water or a mixed solvent of toluene, ethanol, and water is more preferable.

FIG. 1A illustrates a highest occupied molecular orbital of the compound 1 represented by the following structural formula (120) that is an example of the aromatic amine compounds in this embodiment. The highest occupied molecular orbital was obtained by a computational method. The compound 1 that is an example of the aromatic amine compounds in this embodiment includes three benzene rings between a carbazole group and an amine skeleton.

(120)

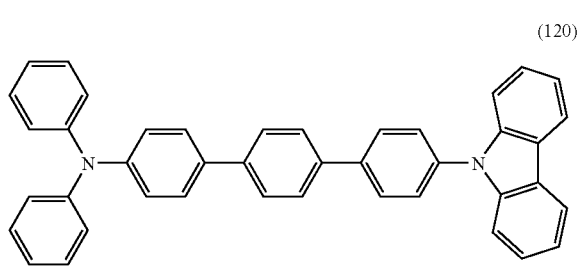

Figure 1B:
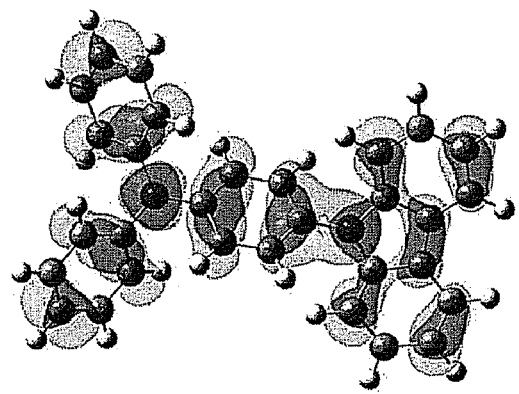

FIG. 1B illustrates a highest occupied molecular orbital of the compound 2 represented by the following structural formula (121) that is an example of compounds having a YGA skeleton. The highest occupied molecular orbital was obtained by the computational method. The compound 2 includes one benzene ring between a carbazole group and an amine skeleton.

(121)

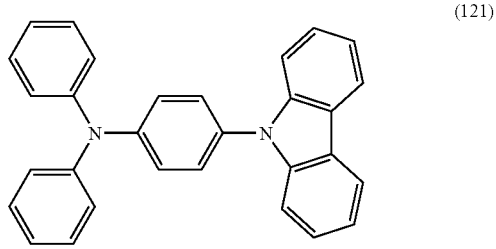

Figure 1C:
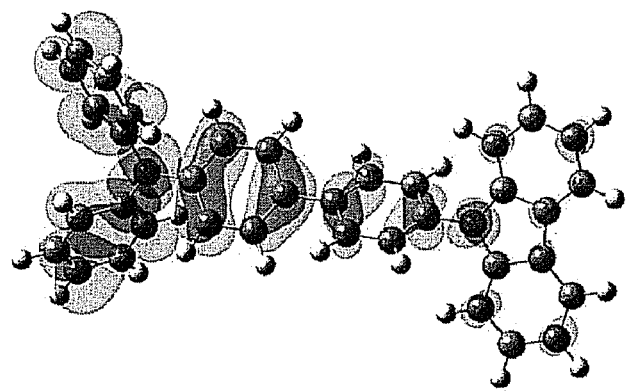

FIG. 1C illustrates a highest occupied molecular orbital of the compound 3 represented by the following structural formula (122) that is an example of compounds having a YGA skeleton. The highest occupied molecular orbital was obtained by the computational method. The compound 3 includes two benzene rings between a carbazole group and an amine skeleton.

(122)

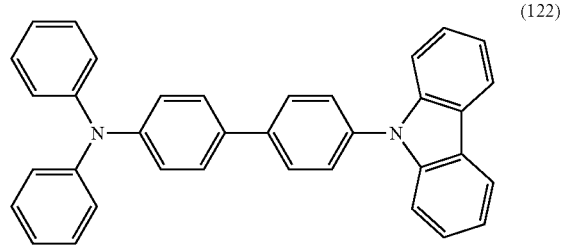

Optimal molecular structures in a ground state of the compounds 1 to 3 were calculated using a density functional theory (DFT) at the B3LYP/6-311 (d, p) level. The accuracy of calculation of the DFT is higher than that of a Hartree-Fock (HF) method which neglects electron correlation. In addition, a calculation cost of the DFT is lower than that of a method of perturbation (MP) which has the same level of accuracy of calculation as the DFT. Therefore, the DFT was employed in this calculation. The calculation was performed using a high performance computer (HPC) (Altix3700 DX, manufactured by SGI). FIGS. 1A to 1C are visualization views of calculation results of the optimal molecular structures obtained by Gaussview 3.0, which is software visualizing computational results.

As illustrated in FIGS. 1B and 1C, the highest occupied molecular orbital exists at a bonding position of a nitrogen atom of the carbazole group and a carbon atom of the phenyl group in each of the compound 2 and the compound 3.

It is thought that the carbazole group of the aromatic amine compound is vulnerable to carrier transfer, and when a hole is provided to the carbazole group, the bonding between the nitrogen atom of the carbazole group and the carbon of the phenyl group bound to the carbazole group becomes weak. For this reason, when a light-emitting element is formed using any of the compound 2 and the compound 3 in which the highest occupied molecular orbital exists at the bonding position, the light-emitting element deteriorates with time due to voltage application, and thus it is thought to be difficult to form a light-emitting element with high reliability.

On the other hand, as illustrated in FIG. 1A, the highest occupied molecular orbital does not exist at a bonding position of a nitrogen atom of the carbazole group and a carbon atom of the phenyl group bound to the carbazole group in the compound 1. For this reason, it is thought that a light-emitting element formed using any of the aromatic amine compounds of this embodiment hardly deteriorates with time by voltage application, and thus can have high reliability.

Further, based on the computational results, the highest occupied molecular orbital (HOMO) level of the compound 1 represented by the structural formula (120) is 5.22 eV, the HOMO (Highest Occupied Molecular Orbital) level of the compound 2 represented by the structural formula (121) is 5.25 eV, and the HOMO (Highest Occupied Molecular Orbital) level of the compound 3 represented by the structural formula (122) is 5.22 eV. The values in the HOMO level are not significantly different and the compounds exhibited low values in the HOMO level.

Optimal molecular structures in triplet excitation states of compounds represented by the structural formula (69) and (120) that are examples of aromatic amine compounds in this embodiment, and 4,4'-bis[N-(1-naphthyl)-N-phenylamino] biphenyl (abbreviation: NPB) as an example of a host material for a phosphorescent material were calculated using a density functional theory (DFT).

(69)

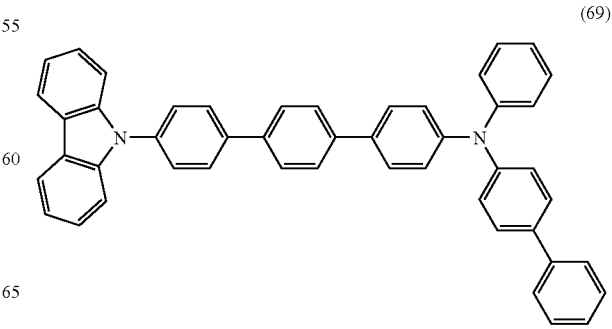

-continued

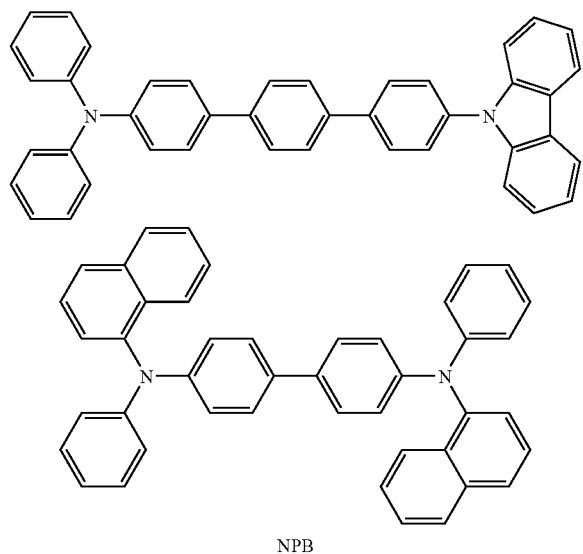

(120)

NPB

Gaussian 03 is used as a quantum chemistry computational program for the calculation. 6-311G (d,p) is adopted as a basis function of H, C and N atoms. B3LYP was adopted as a functional. The excitation energy is calculated from the optimal molecular structures in the triplet excitation states obtained above by a time-dependent density functional theory. The basis function and the functional are calculated in the same manner as above.

The calculated first excitation energy of the triplet excitation state of the aromatic amine compound represented by the structural formula (69) in this embodiment, the aromatic amine compound represented by the structural formula (120), and NPB were 1.76 eV, 1.75 eV and 1.74 eV respectively. The compounds exhibited almost equal first excitation energy.

NPB can be used as a host material for a fluorescent material and a phosphorescent material. In addition, the above computational results showed that the aromatic amine compounds represented by the structural formulae (69) and (120) in this embodiment excited a phosphorescent guest similarly to NPB. Thus, the aromatic amine compounds represented by the structural formulae (69) and (120) can be used as a host material for a phosphorescent material.

As described above, the aromatic amine compounds of this embodiment each have a low highest occupied molecular orbital level, and simultaneously has a structure in which the high highest occupied molecular orbital does not exist at the bonding position of the nitrogen atom of the carbazole group and the carbon atom of the phenyl group bound to the carbazole group. Therefore, the aromatic amine compounds of this embodiment can realize a light-emitting element having both improved emission efficiency and high reliability.

Further, the aromatic amine compounds of this embodiment can be used as a host material of a light-emitting material exhibiting emission at a short wavelength. In addition, the aromatic amine compounds of this embodiment can be used for a layer in contact with the light-emitting material exhibiting emission at a short wavelength.

More specifically, the aromatic amine compounds of this embodiment can be used as a host material for a fluorescent material exhibiting fluorescence at a short wavelength (e.g., blue emission). In addition, the aromatic amine compounds of this embodiment can be used for a layer in contact with the fluorescent material exhibiting fluorescence at a short wavelength. In the case of using any of the aromatic amine compounds of this embodiment for a layer which is in contact with a layer containing a fluorescent material, it is effective to provide a light-emitting region close to a layer containing any of the aromatic amine compounds of this embodiment. In a case of a fluorescent material which emits light at a longer wavelength, the use of any of the aromatic amine compounds of this embodiment can offer a similar advantageous effect.

Specifically, the aromatic amine compounds of this embodiment are each effectively used as a host material for a phosphorescent material which emits phosphorescent light at a relatively short wavelength (e.g., green emission). Further, the aromatic amine compounds of this embodiment can be used for a layer in contact with a phosphorescent material which emits phosphorescent light at a relatively short wavelength. In the case of using any of the aromatic amine compounds of this embodiment for a layer which is in contact with a layer containing a phosphorescent material, it is more effective to provide a light-emitting region close to a layer containing any of the aromatic amine compounds of this embodiment. In a case of a phosphorescent material which emits light at a longer wavelength, the use of any of the aromatic amine compounds of this embodiment can offer a similar advantageous effect.

Further, the aromatic amine compounds of this embodiment are superior in a hole-transporting property. Therefore, the aromatic amine compounds of this embodiment can each be used for a hole-transporting layer of a light-emitting element, which can provide the light-emitting element with favorable characteristics.

Embodiment 2

Figure 2A:
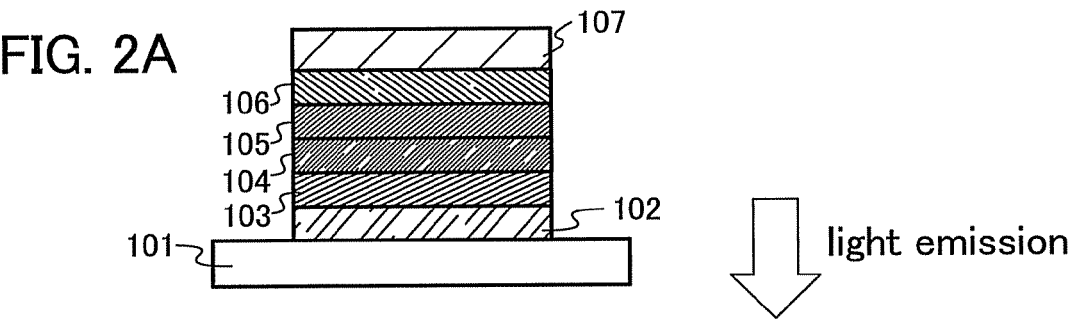
FIGS. 2A to 2C illustrate light-emitting elements according to embodiments of the present invention.

In Embodiment 2, one embodiment of a light-emitting element using any of the aromatic amine compounds described in Embodiment 1 is described below with reference to FIG. 2A.

The light-emitting element according to this embodiment includes a plurality of layers interposed between a pair of electrodes. The plurality of layers are stacked by combining layers such as a layer formed with a substance having a high carrier-injecting property and a layer formed with a substance having a high carrier-transporting property so that a light-emitting region is formed apart from the electrodes, or, so that carriers are recombined in a portion apart from the electrodes.

In this embodiment, the light-emitting element includes a first electrode 102, and a first layer 103, a second layer 104, a third layer 105, a fourth layer 106, and a second electrode 107, which are stacked in this order over the first electrode 102. In description of this embodiment, the first electrode 102 functions as an anode and the second electrode 107 functions as a cathode; however, the present invention is not limited thereto.

A substrate 101 is used as a support of the light-emitting element. The substrate 101 can be formed with, for example, glass, plastic, or the like. Alternatively, the substrate 101 may be formed with any other material that can serve as a support in a fabrication process of the light-emitting element.

As the first electrode 102, a metal, an alloy, a conductive compound, a mixture thereof, or the like having a high work function (specifically, of 4.0 eV or more) is preferably used. Specifically, indium oxide-tin oxide (ITO: Indium Tin Oxide), indium oxide-tin oxide containing silicon or silicon oxide, indium oxide-zinc oxide (IZO: Indium Zinc Oxide), indium oxide containing tungsten oxide and zinc oxide (IWZO), or the like can be used. These conductive metal oxide films are generally formed by sputtering; however, the films may be formed by applying a sol-gel method or the like. For example, indium oxide-zinc oxide (IZO) can be formed by sputtering using a target into which zinc oxide of 1 to 20 wt % is added with respect to indium oxide. Indium oxide containing tungsten oxide and zinc oxide (IWZO) can be formed by sputtering using a target in which tungsten oxide of 0.5 to 5 wt % and zinc oxide of 0.1 to 1 wt % are mixed with indium oxide. Besides, gold, platinum, nickel, tungsten, chrome, molybdenum, iron, cobalt, copper, palladium, or nitride of metal material (for example, titanium nitride) or the like can be used.

The first layer 103 includes a material having a high hole-injecting property. Molybdenum oxide, vanadium oxide, ruthenium oxide, tungsten oxide, manganese oxide, or the like can be used. Besides, the first layer 103 can be formed using a phthalocyanine compound such as phthalocyanine (abbreviation: $H_2Pc$) or copper phthalocyanine (CuPC), or a high molecular compound such as poly (ethylenedioxythiophene)/poly(styrenesulfonate) (PEDOT/PSS) or the like.

In addition, the first layer 103 can be formed using a composite material containing an organic compound and an inorganic compound. In particular, the composite material containing an organic compound and an inorganic compound showing an electron-accepting property to the organic compound has a high hole-injecting and a high hole-transporting property, because electron transfer is conducted between the organic compound and the inorganic compound, so that carrier density is increased.

In a case where the first layer 103 is formed using a composite material containing an organic compound and an inorganic compound, ohmic contact with the first electrode 102 becomes possible, and the material for the first electrode can be selected regardless of its work function.

The inorganic compound used for the composite material is preferably an oxide of a transition metal. In addition, an oxide of metals that belong to Group 4 to 8 of the periodic table can be used. Specifically, vanadium oxide, niobium oxide, tantalum oxide, chromium oxide, molybdenum oxide, tungsten oxide, manganese oxide, and rhenium oxide are preferable because of a high electron-accepting property. Among these, molybdenum oxide is especially preferable because it is stable in the air and is easily treated because of its low hygroscopic property.

As the organic compound used for the composite material, a wide variety of compounds such as an aromatic amine compound, a carbazole derivative, aromatic hydrocarbon, and a high molecular compound (oligomer, dendrimer, polymer, or the like) can be used. The organic compound used for the composite material is preferably an organic compound having a high hole-transporting property. Specifically, a substance having a hole mobility of $10^{-6}$ cm$^2$/Vs or higher is preferably used; however, any substance that has a higher hole-transporting property than an electron-transporting property can be used in addition to the above examples. The organic compounds that can be used for the composite material is specifically shown below.

For example, the aromatic amine compounds may be N,N'-di(p-tolyl)-N,N'-diphenyl-p-phenylenediamine (abbreviation: DTDPPA); 4,4'-bis[N-(4-diphenylaminophenyl)-N-phenylamino]biphenyl (abbreviation: DPAB); 4,4'-bis(N-{4-[N-(3-methylphenyl)-N-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); or the like. In addition, the aromatic amine compounds described in Embodiment 1 may be also used.

The carbazole derivatives that can be used for the composite material may be the following: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphtyl)-N-(9-phenylcarbazol-3-yl)amino]-9-phenylcarbazole (abbreviation: PCzPCN1); and the like.

Moreover, 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl]-2,3,5,6-tetraphenylbenzene; or the like may also be used.

The aromatic hydrocarbon that can be used for the composite material, for example, may be the following: 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. In addition, pentacene, coronene, or the like may also be used. As described above, the aromatic hydrocarbon having a hole mobility of $1 \times 10^{-6}$ cm$^2$/Vs or higher and having 14 to 42 carbon atoms is more preferable.

Aromatic hydrocarbon that can be used for the composite material may have a vinyl skeleton. As aromatic hydrocarbon having a vinyl group, for example, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like are given.

In addition, a high molecular compound such as poly(N-vinylcarbazole) (abbreviation: PVK) or poly(4-vinyl triphenylamine) (abbreviation: PVTPA) can also be used.

The second layer 104 is a layer containing a substance having a high hole-transporting property. The aromatic amine compound described in Embodiment 1 can be suitably used for the second layer 104 because of its high hole-transporting property. By using the aromatic amine compound described in Embodiment 1 for the second layer 104, a light-emitting element with excellent characteristics can be obtained.

The third layer 105 is a layer containing a light-emitting substance. The light-emitting substance is not particularly limited and a wide variety of materials can be used. For example, as a fluorescent material which emits fluorescent light, the following can be given: coumarin derivatives such as coumarin 6 and coumarin 545T; quinacridone derivatives such as N,N'-dimethylquinacridone and N,N'-diphenylquinacridone; acridone derivatives such as N-phenylacridone and N-methylacridone; condensed aromatic compounds such as 2-tert-butyl-9,10-di(2-naphthyl)anthracene (abbreviation: t-BuDNA), 9,10-diphenylanthracene (abbreviation: DPHA), rubrene, periflanthene, and 2,5,8,11-tetra(tert-butyl)perylene (abbreviation: TBP); pyran derivatives such as 4-dicyanomethylene-2-[p-(dimethylamino)styryl]-6-methyl-4H-pyran; amine derivatives such as 4-(2,2-diphenylvinyl)triphenylamine, 9-(4-{N-[4-(carbazol-9-yl)phenyl]-N-phenylamino}phenyl)-10-phenylanthracene (abbreviation: YGAPA) or 4-(10-phenyl-9-anthryl)-4'-9-phenyl-9H-carbazol-3-yl)triphenylamine (abbreviation: PCBAPA); and the like. As a phosphorescent material which emits phosphorescent light, the following can be given: iridium complexes such as tris(2-phenylpyridinato)iridium(III) (abbreviation: Ir(ppy)$_3$), bis(2-phenylpyridinato)iridium(III)acetylacetonate (abbreviation: Ir(ppy)$_2$(acac)), bis{2-(p-tolyl)pyridinato}iridium(III)acetylacetonate (abbreviation: Ir(tpy)$_2$(acac)), bis{2-(2'-benzothienyl)pyridinato}iridium(III)acetylacetonate (abbreviation: Ir(btp)$_2$(acac)), and bis{2-(4,6-difluorophenyl)pyridinato}iridium(III)picolinate (abbreviation: FIrpic); platinum complexes such as a 2,3,7,8,12,13,17,18-octaethyl-21H,23H-porphyrin-platinum complex (pt(OEP)); rare-earth complexes such as 4,7-diphenyl-1,10-phenanthrolinetris(2-tenoyltrifluoroacetonato)europium (III); and the like.

The light-emitting element described in this embodiment is effective when the light-emitting substance included in the third layer 105 is a material that emits blue fluorescent light. Specifically, the aforementioned t-BuDNA, DPHA, TBP, YGAPA, PCBAPA or the like is preferably used as a fluorescent material that emits blue light.

Moreover, the present invention is effective when the light-emitting substance included in the third layer 105 is a material that emits green phosphorescent light. Specifically, a phosphorescent material that emits green light, such as the aforementioned Ir(ppy)$_3$, Ir(ppy)$_2$(acac), Ir(tpy)$_2$(acac) or a phosphorescent material that emits blue-green light the like, such as the aforementioned FIrpic or the like is preferably used.

In the third layer 105, the aforementioned light-emitting substance may be dispersed. As a material for dispersing the light-emitting substance, a wide variety of materials can be used; preferably, a substance which has a higher LUMO level and lower HOMO level than those of the light-emitting substance is used. Specifically, the following can be used: 4,4'-bis[N-(1-naphthyl)-N-phenylamino]biphenyl (abbreviation.: NPB), tris(8-quinolinolato)aluminum (abbreviation: Alq), bis(2-methyl-8-quinolinolato)(4-phenylphenolato)aluminum (abbreviation: BAlq), bis[2-(2-hydroxyphenyl)benzoxazolato]zinc (abbreviation: Zn(BOX)$_2$), 2-tert-butyl-9,10-di(2-naphthyl)anthracene (abbreviation: t-BuDNA), 9-[4-(N-carbazolyl)]phenyl-10-phenylanthracene (abbreviation: CzPA), 2-(4-{N-[4-(carbazol-9-yl)phenyl]-N-phenylamino}phenyl)-5-phenyl-1,3,4-oxadiazole (abbreviation: YGAO11), and the like. As the material for dispersing the light-emitting substance, plural kinds of materials can be used. For example, in order to suppress crystallization, a substance such as rubrene which suppresses crystallization, may be further added. In addition, NPB, Alq, or the like may be further added in order to transfer energy to the light-emitting substance more efficiently.

The fourth layer 106 can be formed using a substance with a high electron-transporting property. For example, a layer containing a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq) can be used. Besides, the following metal complex having an oxazole-based ligand or a thiazole-based ligand, or the like can be used: bis[2-(2-hydroxyphenyl)benzoxazolato]zinc (abbreviation: Zn(BOX)$_2$); bis[2-(2-hydroxyphenyl)benzothiazolato]zinc (abbreviation: Zn(BTZ)$_2$); and the like. Besides the metal complexes, the following can also be used: 2-(4-biphenylyl)-5-(4-tert-butylphenyl)-1,3,4-oxadiazole (abbreviation: PBD); 1,3-bis[5-(p-tert-butylphenyl)-1,3,4-oxadiazole-2-yl]benzene (abbreviation: OXD-7); 3-(4-biphenylyl)-4-phenyl-5-(4-tert-butylphenyl)-1,2,4-triazole (abbreviation: TAZ); bathophenanthroline (abbreviation: BPhen), bathocuproine (abbreviation: BCP); and the like. The materials described here mainly have an electron mobility of $10^{-6}$ cm$^2$/Vs or higher. Note that any substance that has a higher electron-transporting property than a hole-transporting property can be used, in addition to the above substances. Further, the electron-transporting layer may be not only a single layer but also a layered film, that is, stacked layers of two or more made from the aforementioned substances.

As a substance for forming the second electrode 107, a metal, an alloy, a conductive compound, a mixture thereof, or the like having a low work function (specifically, of 3.8 eV or less) can be used. As a specific example of such a cathode material, an element that belongs to Group 1 or 2 of the periodic table, in other words, an alkali metal such as lithium or cesium, an alkaline earth metal such as magnesium, calcium, or strontium or an alloy containing these (MgAg, AlLi), a rare-earth metal such as europium or ytterbium, or an alloy containing these, and the like can be given. However, by stacking a layer having a function to promote electron injection over the second electrode 107 so as to be located between the second electrode 107 and the fourth layer 106, various conductive materials such as Al, Ag, ITO, or ITO containing silicon can be used for the second electrode 107 regardless of its work function.

For the layer having a function to promote electron injection, an alkali metal, an alkaline earth metal, or a compound thereof, such as lithium fluoride (LiF), cesium fluoride (CsF), or calcium fluoride (CaF$_2$) can be used. For example, an alkali metal, an alkaline earth metal, or a compound thereof can be contained in a layer of a substance having an electron-transporting property, and specifically, an Alq layer containing magnesium (Mg), may be used. It is preferable to use such a layer of a material having an electron-transporting property containing an alkali metal or an alkaline earth metal as the electron-injecting layer because electron injection from the second electrode 107 proceeds efficiently.

The first layer 103, the second layer 104, the third layer 105, and the fourth layer 106 can be formed by not only an evaporation method but also various methods such as an inkjet method or a spin coating method. In addition, each of the electrodes or layers may be formed by a different method.

The light-emitting element of this embodiment having the above structure emits light because of current flow by a potential difference generated between the first electrode 102 and the second electrode 107 and recombination of a hole and an electron in the third layer 105 which contains a substance having a high light-emitting property. That is, a light-emitting region is formed in the third layer 105.

Figure 2B:
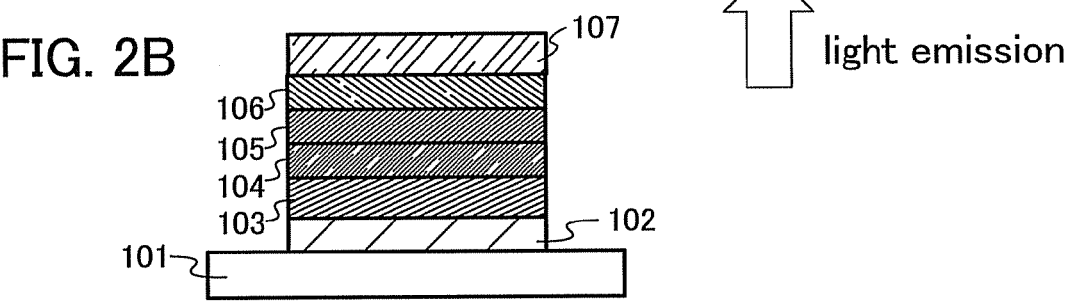
Figure 2C:
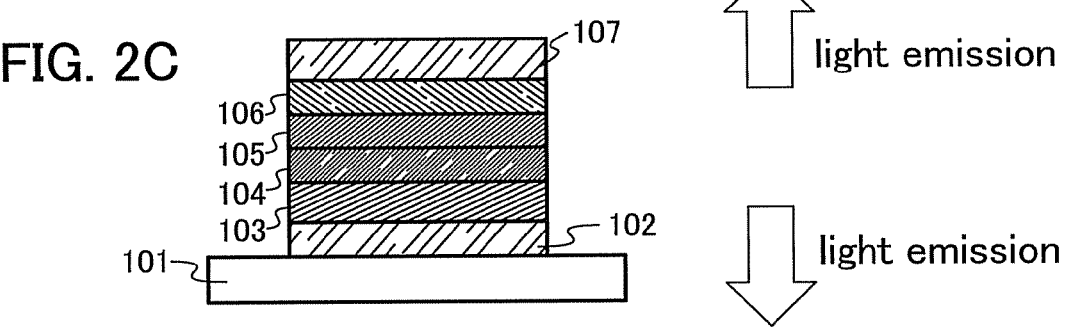

Light emission is extracted to the outside through one or both of the first electrode 102 and the second electrode 107. Accordingly, one or both of the first electrode 102 and the second electrode 107 include(s) a substance having a light-transmitting property. In a case where only the first electrode 102 is formed using a substance having a light-transmitting property, as illustrated in FIG. 2A, light emission is extracted from a substrate side through the first electrode 102. In a case where only the second electrode 107 is formed using a substance having a light-transmitting property, as illustrated in FIG. 2B, light emission is extracted from the side opposite to the substrate through the second electrode 107. In a case where the first electrode 102 and the second electrode 107 are each formed using a substance having a light-transmitting property, as illustrated in FIG. 2C, light emission is extracted from both the substrate side and the opposite side through the first electrode 102 and the second electrode 107.

Note that the structure of the layers provided between the first electrode 102 and the second electrode 107 is not limited to the above. Any other structure than the above may be employed as long as a light-emitting region for recombining a hole and an electron is provided in a portion away from the first electrode 102 and the second electrode 107 so that quenching due to adjacency of the light-emitting region and a metal can be suppressed.

In other words, a stack structure of the layers is not particularly limited, and the layers may be structured by freely combining layers formed with a substance having a high electron-transporting property, a substance having a high hole-transporting property, a substance having a high electron-injecting property, a substance having a high hole-injecting property, a substance having a bipolar property (a substance having a high electron- and hole-transporting property), a hole blocking material, and/or the like with any of the aromatic amine compounds described in Embodiment 1.

Figure 3:
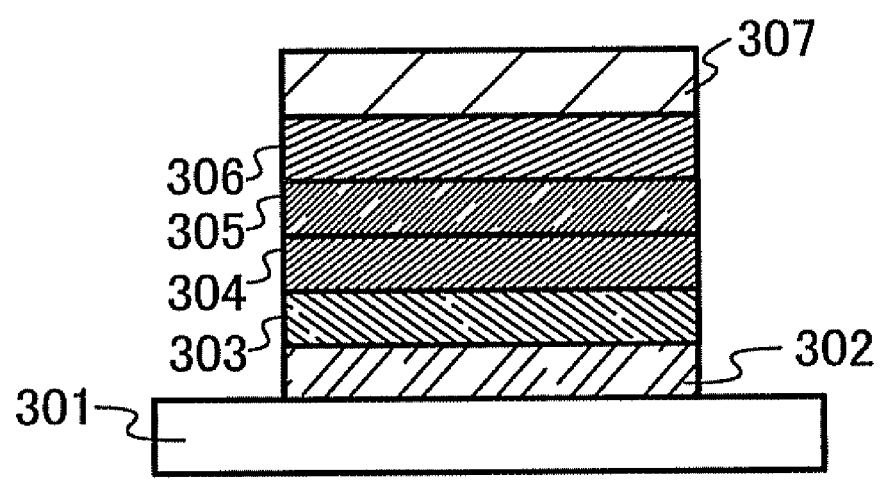
FIG. 3 illustrates a light-emitting element according to one embodiment of the present invention.

A light-emitting element illustrated in FIG. 3 has a structure in which a first layer 303 including a substance having a high electron-transporting property, a second layer 304 including a light-emitting substance, a third layer 305 including a substance having a high hole-transporting property, a fourth layer 306 including a substance having a high hole-injecting property, and a second electrode 307 functioning as an anode are stacked in this order over a first electrode 302 functioning as a cathode. A reference numeral 301 denotes a substrate.

In this embodiment, the light-emitting element is fabricated over a substrate formed of glass, plastic, or the like. By forming a plurality of such light-emitting elements over a substrate, a passive matrix light-emitting device can be manufactured. In addition, for example, a thin film transistor (TFT) may be formed over a substrate formed of glass, plastic, or the like, and a light-emitting element may be manufactured over an electrode electrically connected to the TFT. Thus, an active matrix light-emitting device which controls the driving of the light-emitting element by a TFT can be manufactured. A structure of the TFT is not particularly limited. Either a staggered TFT or an inverted staggered TFT may be employed. In addition, crystallinity of a semiconductor used for the TFT is not particularly limited either; an amorphous semiconductor or a crystalline semiconductor may be used. Further, a driving circuit on the TFT substrate may be formed with both n-type and p-type TFTs or either n-type or p-type TFTs.

The aromatic amine compounds described in Embodiment 1 each have a low HOMO level. In addition, it is thought that each of the aromatic amine compounds described in Embodiment 1 has such a structure the high highest occupied molecular orbital does not exist at the bonding position of the nitrogen of the carbazole group and the carbon of the phenyl group. Therefore, the use of such an aromatic amine compound can realize a light-emitting element having both improvement of emission efficiency and high reliability.

In addition, because the light-emitting element of this embodiment has high emission efficiency, the power consumption can be reduced.

Embodiment 3

In Embodiment 3, a light-emitting element having a structure different from that described in Embodiment 2 is described.

The aromatic amine compounds described in Embodiment 1 can each be used for a host material for dispersing light-emitting substance. That is, any of the aromatic amine compounds described in Embodiment 1 can be used for the host material of the third layer 105 described in Embodiment 2. As the light-emitting substance to be dispersed in any of the aromatic amine compounds described in Embodiment 1, various types of fluorescent materials and phosphorescent materials can be used.

In a case where the aromatic amine compound of one embodiment of the present invention is used for the third layer 105, the second layer 104 can be formed of various materials; for example, a variety of aromatic amine compounds can be used. Examples of materials which are widely used include 4,4'-bis[N-(3-methylphenyl)-N-phenylamino]biphenyl; a derivative thereof such as 4,4'-bis[N-(1-napthyl)-N-phenylamino]biphenyl (abbreviation: NPB); and a starburst aromatic amine compound such as 4,4',4''-tris(N,N-diphenylamino)triphenylamine and 4,4',4''-tris[N-(3-methylphenyl)-N-phenylamino]triphenylamine. The substances described here mainly have a hole mobility of $10^{-6}$ cm$^2$/Vs or higher; however, any other substance that has a higher hole-transporting property than an electron-transporting property can be used in addition to the above-described substances. Note that the second layer 104 is not limited to a single layer, but may be a mixed layer or a stacked layer of two or more layers formed with the aforementioned materials.

The aromatic amine compounds described in Embodiment 1 each have a low HOMO level. In addition, it is thought that each of the aromatic amine compounds described in Embodiment 1 has such a structure the high highest occupied molecular orbital does not exist at the bonding position of the nitrogen of the carbazole group and the carbon of the phenyl group. Therefore, the use of such an aromatic amine compound can realize a light-emitting element having both improvement of emission efficiency and high reliability.

In addition, because the light-emitting element of this embodiment has high emission efficiency, the power consumption can be reduced.

Embodiment 4

In Embodiment 4, a light-emitting element having a structure different from those described in Embodiments 2 and 3 is described.

By using any of the aromatic amine compounds described in Embodiment 1 for the third layer 105 described in Embodiment 2, light can be emitted from the aromatic amine compound described in Embodiment 1. Because the aromatic amine compounds described in Embodiment 1 each emit violet to blue light, a light-emitting element emitting violet to blue light can be obtained.

The third layer 105 may include only any of the aromatic amine compounds described in Embodiment 1 or may include any of the aromatic amine compounds described in Embodiment 1 that is dispersed in another substance. As the substance in which any of the aromatic amine compounds described in Embodiment 1 is dispersed, in addition to the substances with a high hole-transporting property and the substances with a high electron-transporting property described in Embodiment 2, various materials such as the following can be used: 3-(4-biphenylyl)-4-phenyl-5-(4-tert-butylphenyl)-1,2,4-triazole (abbreviation: TAZ), 4,4'-di(N-carbazolyl)biphenyl (abbreviation: CBP), 2,2',2''-(1,3,5-benzenetri-yl)-tris[1-phenyl-1H-benzimidazole] (abbreviation: TPBI), and the like.

The aromatic amine compounds described in Embodiment 1 each have a low HOMO level. In addition, it is thought that each of the aromatic amine compounds described in Embodiment 1 has such a structure the high highest occupied molecular orbital does not exist at the bonding position of the nitrogen of the carbazole group and the carbon of the phenyl group. Therefore, the use of such an aromatic amine compound can realize a light-emitting element having both improvement of emission efficiency and high reliability.

In addition, because the light-emitting element of this embodiment has high emission efficiency, the power consumption can be reduced.

The structures described in Embodiment 2 and 3 can be used as appropriate, except for the third layer 105.

Embodiment 5

In Embodiment 5, a light-emitting element having a structure different from those described in Embodiments 2 to 4 is described.

Because the aromatic amine compounds described in Embodiment 1 each have a hole-injecting property, any of the aromatic amine compounds described in Embodiment 1 can be used for the first layer 103 described in Embodiment 2. In addition, a composite material including any of the aromatic amine compounds described in Embodiment 1 and an inorganic compound can be used for the first layer 103. The inorganic compound used for the composite material is preferably an oxide of a transition metal. In addition, an oxide of metals that belong to Group 4 to 8 of the periodic table can be used. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air and is easily treated because of its low hygroscopic property.

In the composite material including any of the aromatic amine compounds described in Embodiment 1 and the inorganic compound, electrons are transported between the organic compound and the inorganic compound to increase carrier density; therefore, the hole-injecting property and the hole-transporting property are excellent. In a case where the first layer 103 is formed using the composite material including any of the aromatic amine compounds described in Embodiment 1 and the inorganic compound, an ohmic contact with the first electrode 102 is possible; thus, the material for forming the first electrode can be selected regardless of the work function.

In a case where any of the aromatic amine compounds described in Embodiment 1 is used for the first layer 103, a wide variety of materials can be used as a substance for forming the second layer 104; for example, an aromatic amine compound (that is, a compound having a benzene ring-nitrogen bond) can be used. Examples of the material which are widely used include 4,4'-bis[N-(3-methylphenyl)-N-phenylamino]biphenyl; a derivative thereof such as 4,4'-bis[N-(1-napthyl)-N-phenylamino]biphenyl (abbreviation: NPB); and a starburst aromatic amine compound such as 4,4',4''-tris(N,N-diphenyl-amino)triphenylamine and 4,4',4''-tris[N-(3-methylphenyl)-N-phenylamino]triphenylamine. The substances described here mainly have a hole mobility of $10^{-6}$ cm$^2$/Vs or higher; however, any other substance that has a higher hole-transporting property than an electron-transporting property may be used, in addition to the above-described substances. Note that the second layer 104 is not limited to a single layer, but may be a mixed layer or a stacked layer of two or more layers formed of the aforementioned materials.

In addition, any of the aromatic amine compounds described in Embodiment 1 may be used for the first layer 103 and the second layer 104.

Because the aromatic amine compounds described in Embodiment 1 each have a hole-injecting property, the aromatic amine compounds of the present invention can each be suitably used as the hole-injecting layer of the light-emitting element.

The aromatic amine compounds described in Embodiment 1 each have a low HOMO level. In addition, it is thought that each of the aromatic amine compounds described in Embodiment 1 has such a structure the high highest occupied molecular orbital does not exist at the bonding position of the nitrogen of the carbazole group and the carbon of the phenyl group. Therefore, the use of such an aromatic amine compound can realize a light-emitting element having both improvement of emission efficiency and high reliability.

In addition, because the light-emitting element of this embodiment has high emission efficiency, the power consumption can be reduced.

The structures described in Embodiments 2 to 4 can be used as appropriate, except for the first layer 103.

Embodiment 6

In Embodiment 6, an embodiment of a light-emitting element having a structure in which a plurality of light-emitting units are stacked (hereinafter, referred to as a stacked element) is described with reference to FIG. 4. This light-emitting element is a light-emitting element having a plurality of light-emitting units between a first electrode and a second electrode. Each of the light-emitting units may have a similar structure to that of the layer containing a light-emitting substance described in Embodiment 2. That is, the light-emitting element described in Embodiment 2 has one light-emitting unit, whereas the light-emitting element described in this embodiment has a plurality of light-emitting units.

Figure 4:
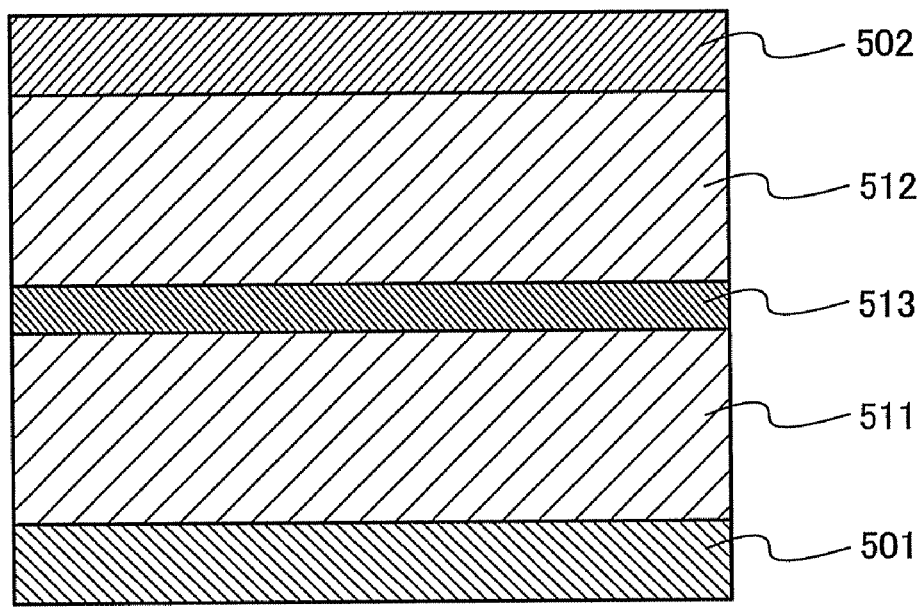
FIG. 4 illustrates a light-emitting element according to one embodiment of the present invention.

In FIG. 4, a first light-emitting unit 511 and a second light-emitting unit 512 are stacked between a first electrode 501 and a second electrode 502. Materials similar to those in Embodiment 2 can be applied to the first electrode 501 and the second electrode 502. The first light-emitting unit 511 and the second light-emitting unit 512 may have either the same structure or different structures. The structure(s) may be similar to those described in Embodiments 2 to 5.

A charge-generating layer 513 includes a composite material of an organic compound and a metal oxide. The composite material of an organic compound and a metal oxide includes any of the organic compounds described in Embodiment 2 and a metal oxide such as vanadium oxide, molybdenum oxide, or tungsten oxide. As the organic compound, various types of compounds such as an aromatic amine compound, a carbazole derivative, aromatic hydrocarbon, and a high molecular compound (oligomer, dendrimer, polymer, or the like) can be used. Note that an organic compound having a hole mobility of $10^{-6}$ cm$^2$/Vs or higher is preferably used as a hole-transporting organic compound; however, any other substance that has a higher hole-transporting property can be used in addition to the above-described substance. The composite of the organic compound and a metal oxide is superior in a carrier-injecting property and a carrier-transporting property, and accordingly, low-voltage driving and low-current driving can be realized.

Note that the charge-generation layer 513 may be formed with a combination of the composite of the organic compound and a metal oxide with another material. For example, the charge-generation layer 513 may be formed with a combination of a layer containing the composite of an organic compound and a metal oxide with a layer containing a compound selected from electron-donating substances and a compound having a high electron-transporting property. Alternatively, the charge-generation layer 513 may be formed with a combination of a layer containing the composite of an organic compound and a metal oxide with a transparent conductive film.

In any case, the charge-generation layer 513 formed between the first light-emitting unit 511 and the second light-emitting unit 512 preferably has a property such that electrons are injected to one light-emitting unit and holes are injected to the other light-emitting unit when a voltage is applied to the first electrode 501 and the second electrode 502.

The light-emitting element having two light-emitting units is described in this embodiment; similarly, the mode of this embodiment can be applied to a light-emitting element in which three or more light-emitting units are stacked. When the charge-generating layer is provided between the pair of electrodes so as to partition the plural light-emitting units like the light-emitting element of this embodiment, the element can have long lifetime in a high luminous region while keeping low current density. Moreover, a light-emitting device with low power consumption, which can be driven at low voltage, can be realized.

Note that this embodiment can be combined with any of the other embodiments as appropriate.

Embodiment 7

In this embodiment, a light-emitting device that is fabricated using any of the aromatic amine compounds described in Embodiment 1 is described with reference to FIGS. 5A and 5B.

FIG. 5A is a top view of a light-emitting device and FIG. 5B is a cross-sectional view of FIG. 5A taken along lines A-A' and B-B'. In order to control light emission of the light-emitting element, this light-emitting device includes a driving circuit portion (source side driving circuit) 601, a pixel portion 602, and a driving circuit portion (gate side driving circuit) 603, which are illustrated by dashed lines. In addition, reference numeral 604 denotes a sealing substrate; 605 denotes a sealing material; and the inside portion surrounded by the sealing material 605 denotes a space 607.

Note that a leading wiring 608 transmits a signal that is to be input to the source side driving circuit 601 and the gate side driving circuit 603 and receives a video signal, clock signal, start signal, reset signal or the like, from an FPC (flexible printed circuit) 609 that is an external input terminal. Although only the FPC is illustrated here, this FPC may be provided with a printed wiring board (PWB). The light-emitting device in this specification includes not only a light-emitting device but also a state of a light-emitting device to which the FPC or PWB is attached.

Next, a cross-sectional structure will be described with reference to FIG. 5B. Although the driving circuit portion and the pixel portion are formed on an element substrate 610, the source side driving circuit 601 that is the driving circuit portion, and one of the pixels in the pixel portion 602 are illustrated here.

Note that the source side driving portion 601 is formed with a CMOS circuit by combination of an n-channel type TFT 623 and a p-channel type TFT 624. The driving circuit may be formed with various types of circuits such as a CMOS circuit, a PMOS circuit, and/or an NMOS circuit. In this embodiment, it is not always necessary to form the driving circuit on the same substrate as the pixel portion, and it is also possible to form the driving circuit not on the substrate but outside the substrate.

In addition, the pixel portion 602 is formed from a plurality of pixels each including a switching TFT 611, a current-controlling TFT 612 and the first electrode 613 that is electrically connected to the drain of the current controlling TFT 612. Note that an insulator 614 is formed to cover the end portion of the first electrode 613. Here, the insulator 614 is formed using a positive photosensitive acrylic resin film.

In order to improve the coverage, the insulator 614 is formed to have a curved surface with curvature at its upper or lower end portion. For example, in a case where a positive photosensitive acryl is used as the insulator 614, it is preferable that only an upper end portion of the insulator 614 has a curved surface with a curvature radius (0.2 μm to 3 μm). As the insulator 614, either of a negative photosensitive material that becomes insoluble in an etchant by light and a positive photosensitive material that becomes soluble in an etchant by light can be used.

The layer 616 containing a light-emitting substance and the second electrode 617 are formed on the first electrode 613. As a material used for the first electrode 613 which functions as an anode, a material having a high work function is preferably used. For example, a single layer of an indium tin oxide (ITO) film, an indium tin oxide film containing silicon, an indium oxide film containing zinc oxide (ZnO) of 2 to 20 wt %, a titanium nitride film, a chromium film, a tungsten film, a Zn film, a Pt film, a stacked layer of a titanium nitride film and a film mainly containing aluminum, a three-layer stacked structure of a titanium nitride film, a film mainly containing aluminum and a titanium nitride film, or the like can be used. Note that it is preferable to employ a stacked-layer structure because resistance as a wiring is low and favorable ohmic contact can be obtained.

In addition, the layer 616 containing a light-emitting substance may be formed by a variety of methods such as evaporation using an evaporation mask, inkjet, or spin coating. The layer 616 containing a light-emitting substance includes any of the aromatic amine compounds described in Embodiment 1.

As another material for forming the layer 616 containing a light-emitting substance, a low molecular compound or a high molecular compound (including oligomer, dendrimer and polymer) may be used.

As a material used for the second electrode 617 which is formed over the layer 616 containing a light-emitting substance and functions as a cathode, a material having a low work function (Al, Mg, Li, Ca, or an alloy or a compound thereof such as MgAg, MgIn, AlLi, LiF, or $CaF_2$) is preferably used. In a case where light generated in the layer 616 containing the light-emitting substance is transmitted through the second electrode 617, the second electrode 617 is preferably formed by stacking a thin metal film and a transparent conductive film (such as ITO, indium oxide containing 2 to 20 wt % zinc oxide, indium tin oxide containing silicon, and zinc oxide (ZnO)).

By attaching the sealing substrate 604 and the element substrate 610 with the sealing material 605, the light-emitting element 618 is provided in the space 607 that is surrounded by the element substrate 610, the sealing substrate 604, and the sealing material 605. Further, the space 607 is filled with a filler. There are cases where the space 607 is filled with an inert gas (such as nitrogen and argon) or the space 607 is filled with the sealing material 605.

An epoxy based resin is preferably used for the sealing material 605. In addition, it is desirable to use a material that allows permeation of moisture or oxygen as little as possible. As the sealing substrate 604, a plastic substrate formed of FRP (Fiberglass-Reinforced Plastics), PVF (polyvinyl fluoride), polyester, acrylic, or the like can be used besides a glass substrate or a quartz substrate.

As described above, the light-emitting device which is manufactured using any of the aromatic amine compounds described in Embodiment 1 can be obtained.

The light-emitting device of this embodiment uses any of the aromatic amine compounds described in Embodiment 1; therefore, the light-emitting device can have favorable characteristics. Specifically, a light-emitting device having high reliability and high emission efficiency can be obtained.

Figure 6:
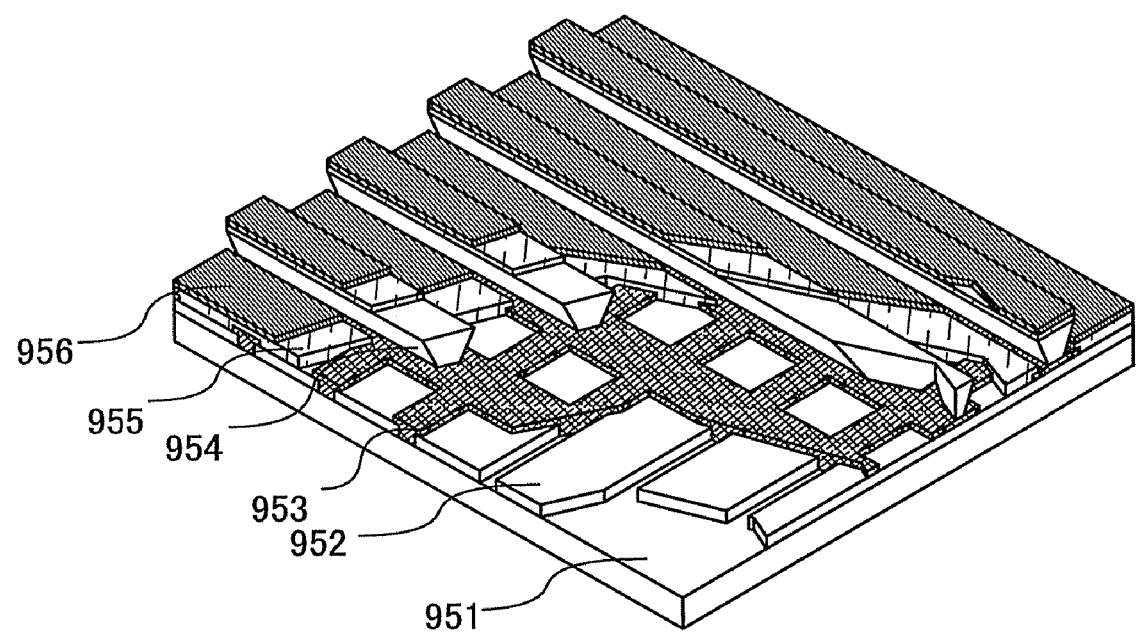
FIG. 6 illustrates a light-emitting device according to one embodiment of the present invention.

As described above, in this embodiment, an active matrix type light-emitting device in which operation of a light-emitting element is controlled by a transistor is described. Alternatively, a passive matrix type light-emitting device may also be used. FIG. 6 is a perspective view of a passive matrix type light-emitting device manufactured by application of the aforementioned embodiment. In FIG. 6, a layer 955 containing a light-emitting substance is provided between an electrode 952 and an electrode 956 over a substrate 951. An end portion of the electrode 952 is covered with an insulating layer 953. A partition layer 954 is provided over the insulating layer 953. The sidewalls of the partition layer 954 are sloping so that a distance between both sidewalls is gradually narrowed toward the surface of the substrate. That is, a cross section in the short side of the partition layer 954 is trapezoidal, and the lower side (the side in the same direction as the plane direction of the insulating layer 953, and is in contact with the insulating layer 953) is shorter than the upper side (the side in the same direction as the plane direction of the insulating layer 953, and is not in contact with the insulating layer 953). By providing the partition layer 954 in this manner, defects of the light-emitting element due to static charge and the like can be prevented. In addition, when a light-emitting element with high light emission efficiency of the present invention is included in a passive matrix light-emitting device, the light-emitting device can have high reliability and high light emission efficiency. Moreover, the high emission efficiency leads to low power consumption.

Embodiment 8

In Embodiment 8, electronic devices of the present invention which include, as parts thereof, the light-emitting device described in Embodiment 7 is described. The electronic devices of this embodiment include any of the aromatic amine compounds described in Embodiment 1, and have a display portion having high reliability. In addition, the display portion has high emission efficiency. The high emission efficiency leads to low power consumption of the electronic devices.

Examples of the electronic devices having the light-emitting element fabricated using any of the aromatic amine compounds described in Embodiment 1 include cameras such as video cameras or digital cameras, goggle type displays, navigation systems, sound reproducing devices (car audio systems, audio components, or the like), computers, game machines, mobile information terminals (mobile computers, mobile phones, mobile game machines, electronic books, or the like), image reproducing devices having a recording medium (specifically, a device which reproduces a recording medium such as a digital versatile disc (DVD) and has a display device for displaying the image), and the like. Some specific examples thereof are illustrated in FIGS. 7A to 7D.

Figure 7A:
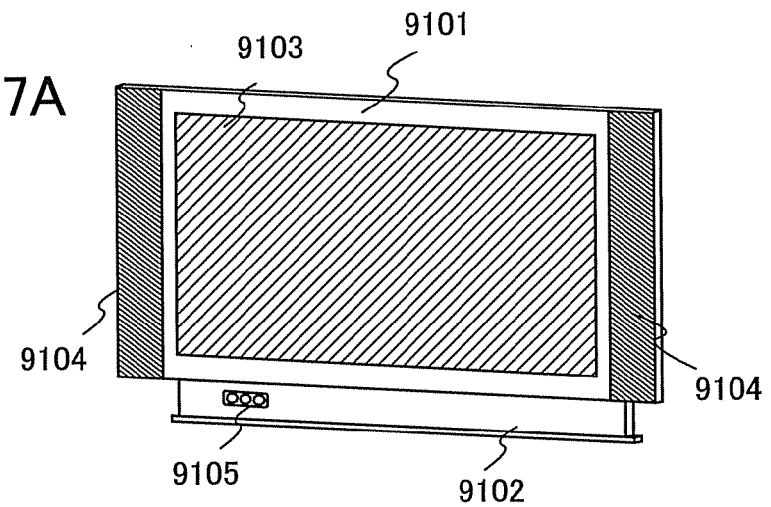
FIGS. 7A to 7D illustrate electronic devices according to embodiments of the present invention.

FIG. 7A is a television device according to this embodiment, and the television device includes a chassis 9101, a support base 9102, a display portion 9103, a speaker portion 9104, a video input terminal 9105, and the like. In the television device, the display portion 9103 has light-emitting elements, which are similar to those described in Embodiments 2 to 6, arranged in matrix. The light-emitting elements have such advantages that the emission efficiency is high and the reliability is also high. The display portion 9103 which includes the light-emitting elements has similar features; therefore, in the television device, image quality is hardly deteriorated and power consumption is reduced. With such features, a deterioration compensation functional circuit and a power supply circuit can be significantly reduced or the size thereof can be reduced in the television device; therefore, a small size and lightweight of the chassis 9101 and the support base 9102 can be realized. The television device according to this embodiment can realize low power consumption, high image quality, and a small size and lightweight.

Figure 7B:
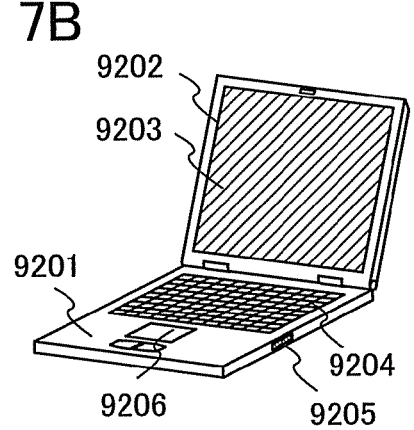

FIG. 7B is a computer according to this embodiment, and the computer includes a main body 9201, a chassis 9202, a display portion 9203, a keyboard 9204, an external connection port 9205, a pointing device 9206, and the like. In the computer, the display portion 9203 has light-emitting elements, which are similar to those described in Embodiments 2 to 6, arranged in matrix. The light-emitting elements have such advantages that the emission efficiency is high and the reliability is also high. The display portion 9203 which includes the light-emitting elements has similar features; therefore, in the computer, image quality is hardly deteriorated and power consumption is reduced. With such features, a deterioration compensation functional circuit and a power supply circuit can be significantly reduced or the size thereof can be reduced in the computer; therefore, a small size and lightweight of the main body 9201 and the chassis 9202 can be realized. The computer according to this embodiment mod can realize low power consumption, high image quality, and a small size and lightweight; therefore, a product suitable for environment can be provided.

Figure 7C:
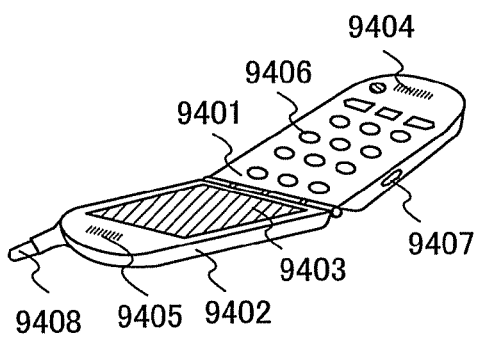

FIG. 7C is a mobile phone according to this embodiment, and the mobile phone includes a main body 9401, a chassis 9402, a display portion 9403, an audio input portion 9404, an audio output portion 9405, operation keys 9406, an external connection port 9407, an antenna 9408, and the like. In the mobile phone, a display portion 9403 has light-emitting elements, which are similar to those described in Embodiments 2 to 6, arranged in matrix. The light-emitting elements have such advantages that the emission efficiency is high and the reliability is also high. The display portion 9403 which includes the light-emitting elements has similar features; therefore, in the mobile phone, image quality is hardly deteriorated and power consumption is reduced. With such features, a deterioration compensation functional circuit and a power supply circuit can be significantly reduced or the size thereof can be reduced in the mobile phone; therefore, a small size and lightweight of the main body 9401 and the chassis 9402 can be realized. The mobile phone according to this embodiment can realize low power consumption, high image quality, and a small size and lightweight; therefore, a product suitable for carrying can be provided.

Figure 7D:
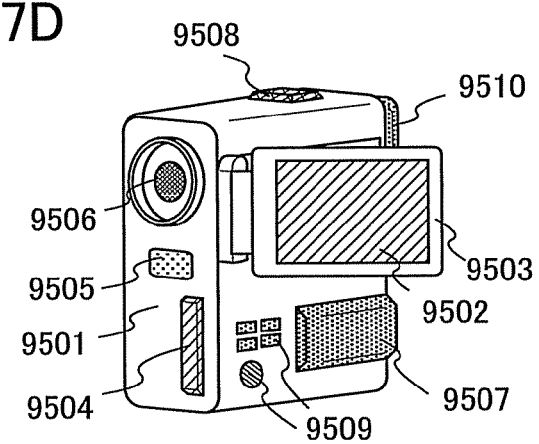

FIG. 7D is a camera according to this embodiment mode, and the camera includes a main body 9501, a display portion 9502, a chassis 9503, an external connection port 9504, a remote control receiving portion 9505, an image receiving portion 9506, a battery 9507, an audio input portion 9508, an operation key 9509, an eyepiece portion 9510, and the like. In the camera, the display portion 9502 has light-emitting elements, which are similar to those described in Embodiments 2 to 6, arranged in matrix. The light-emitting elements have such advantages that the emission efficiency is high and the reliability is also high. The display portion 9502 which includes the light-emitting elements has similar features; therefore, in the camera, image quality is hardly deteriorated and power consumption can be reduced. With such features, a deterioration compensation functional circuit and a power supply circuit can be significantly reduced or the size thereof can be reduced in the camera; therefore, a small size and lightweight of the main body 9501 can be realized. The camera according to this embodiment can realize low power consumption, high image quality, and a small size and lightweight; therefore, a product suitable for carrying can be provided.

As described above, the applicable range of the light-emitting device of an embodiment of the present invention is so wide that this light-emitting device can be applied to electronic devices of a variety of fields. By the use of any of the aromatic amine compounds described in Embodiment 1, an electronic device including a display portion with high emission efficiency and high reliability can be provided.

Further, the light-emitting device of one embodiment of the present invention can also be used for a lighting device. An embodiment using the light-emitting element described in Embodiments 2 to 6, to which the present invention is applied as a lighting device will be described with reference to FIG. 8.

Figure 8:
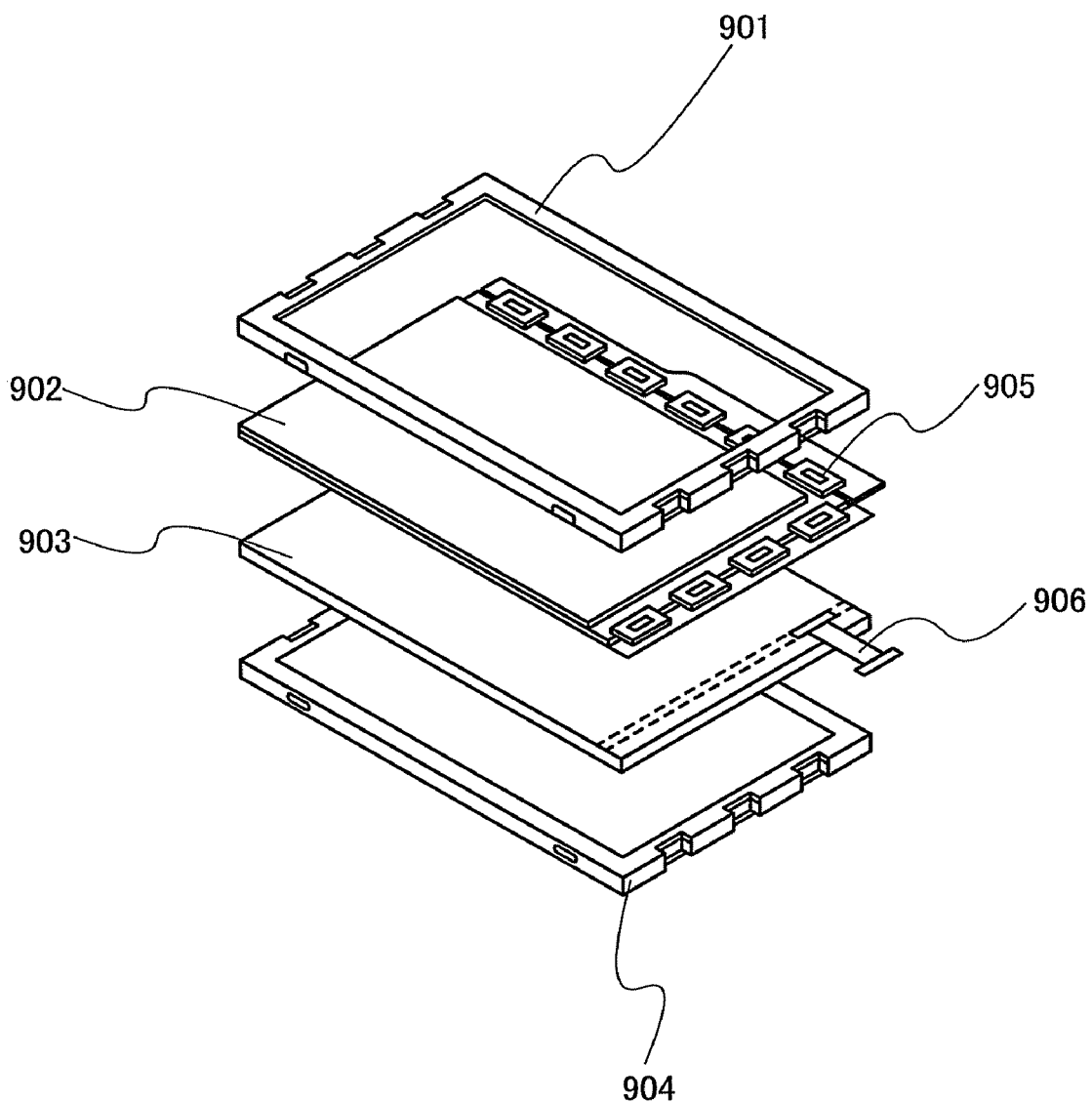
FIG. 8 illustrates an electronic device according to one embodiment of the present invention.

FIG. 8 is an example of a liquid crystal display device using the light-emitting device of one embodiment of the present invention as a backlight. The liquid crystal display device illustrated in FIG. 8 includes a chassis 901, a liquid crystal layer 902, a backlight 903, and a chassis 904, and the liquid crystal layer 902 is connected to a driver IC 905. In addition, a light-emitting device of one embodiment of the present invention is used in the backlight 903 and current is supplied thereto through a terminal 906.

By using the light-emitting device of one embodiment of the present invention for a backlight of a liquid crystal display device, a backlight with high light emission efficiency can be obtained. In addition, the light-emitting device of one embodiment of the present invention is a lighting device with planar light emission and can have a large area; therefore, the backlight can also have a large area, and a liquid crystal display device having a large area can be obtained. Furthermore, because the light-emitting device of one embodiment of the present invention is thin and consumes lower power, the thickness and power consumption of the display device can be reduced. The light-emitting device of one embodiment of the present invention has high reliability; therefore, a liquid crystal display device using the light-emitting device also has high reliability.

Figure 9:
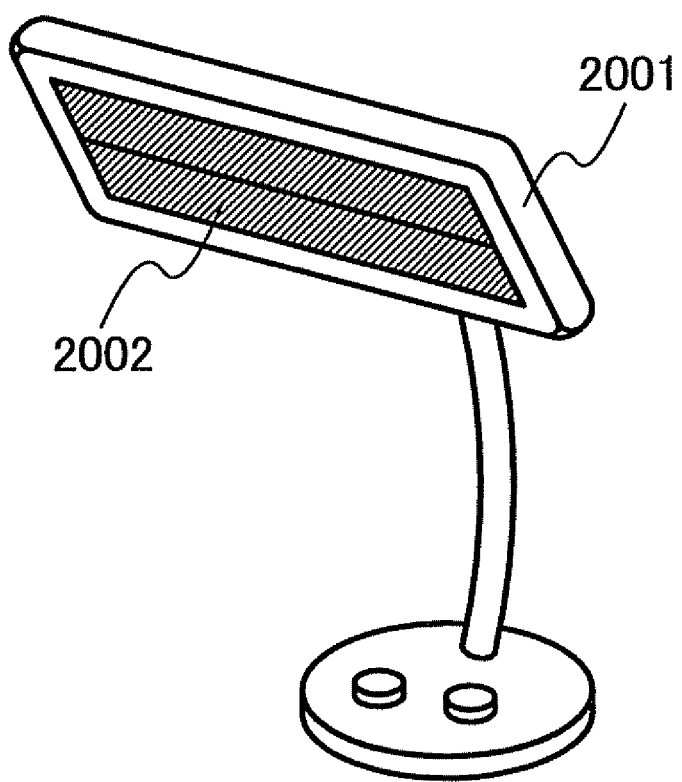
FIG. 9 illustrates a light-emitting device according to one embodiment of the present invention.

FIG. 9 is an example in which the light-emitting device of one embodiment of the present invention is used as a table lamp that is a lighting device. The table lamp of FIG. 9 has a chassis 2001 and a light source 2002, and the light-emitting device of one embodiment of the present invention is used as the light source 2002. The light-emitting device can emit light with high luminance, and thus it can illuminate an area when a man does delicate work or the like.

Figure 10:
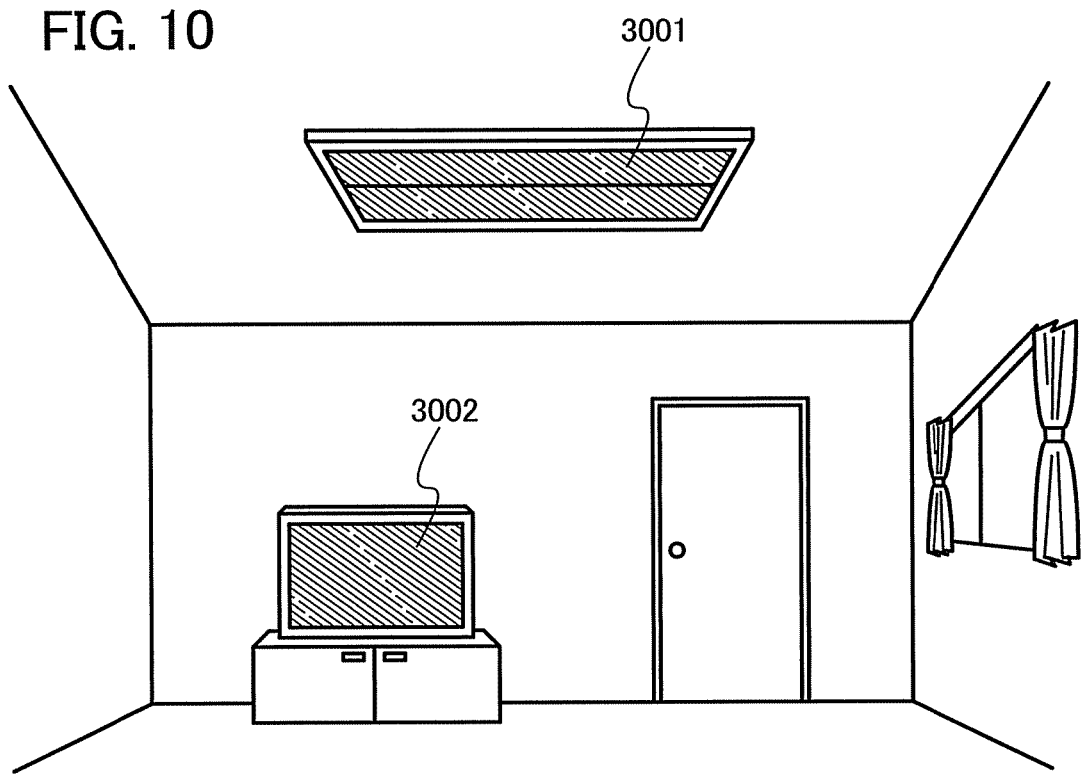
FIG. 10 illustrates a light-emitting device according to one embodiment of the present invention.

FIG. 10 is an example in which the light-emitting device according to Embodiment 7 is used as an indoor lighting device 3001. Because the light-emitting device of one embodiment of the present invention can have a large area, it can be used as a large-area lighting device. Further, because the light-emitting device of one embodiment of the present invention is thin and consumes lower power, the light-emitting device can be used as a lighting device which is thin and consumes low power. As described above, a television device 3002 as illustrated in FIG. 7A can be placed in a room where the light-emitting device of one embodiment of the present invention is used as the indoor lighting device 3001, and thus public broadcasting and movies can be watched with the television device 3002.

EXAMPLE 1

In Example 1, a synthesis method of N-(biphenyl-4-yl)-4''-(9H-carbazol-9-yl)-N-phenyl-[1,1',4',1'']terphenyl-4-amine (abbreviation: YGTA1BP) represented by the structural formula (69) which is one embodiment of the present invention is described.

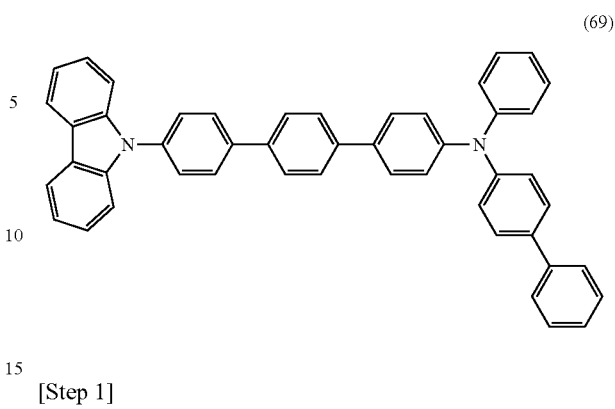

(69)

[Step 1]

Synthesis of 9-(4'-iodobiphenyl-4-yl)-9H-carbazole

A synthesis scheme (C-1) of 9-(4'-iodobiphenyl-4-yl)-9H-carbazole is shown below.

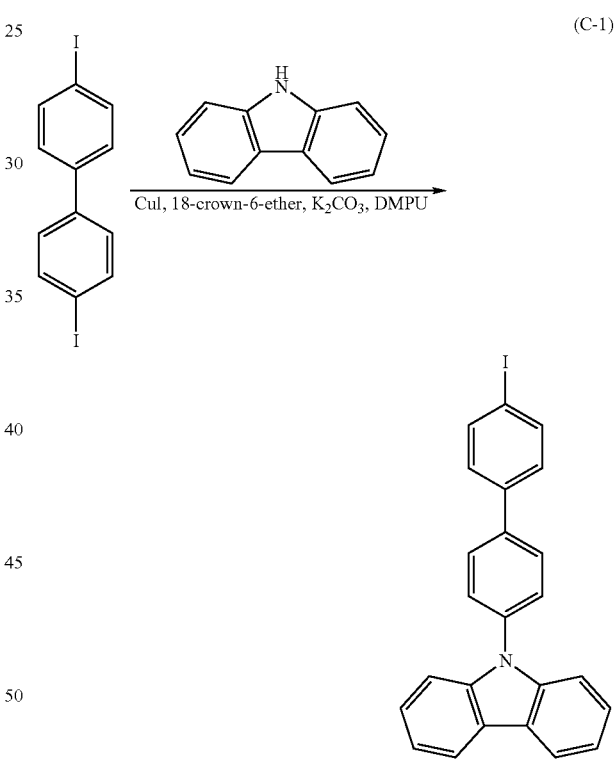

(C-1)

Initially, 49 g (120 mmol) of diiodobiphenyl, 17 g (100 mmol) of carbazole, 1.0 g (5.0 mmol) of copper(I) iodide, 1.3 g (5.0 mmol) of 18-crown-6-ether, 10 g (75 mmol) of potassium carbonate, 40 mL of 1,3-dimethyl-3,4,5,6-tetrahydro-2 (1H)-pyrimidinone (abbreviation: DMPU) were put in a 500 mL three-neck flask, and the atmosphere of the flask was substituted by nitrogen. The mixture was stirred at 170° C. for 6.5 hours. After stirring, water was added to the mixture and the mixture was filtrated to give a precipitate. The precipitate was washed with 1M hydrochloric acid, water, an aqueous solution of sodium hydrogen carbonate, and water in this order, and then was recrystallized from a mixture solution of toluene and hexane. The resulting solid was recrystallized from chloroform to give 40 g of the target substance, white powder of 9-(4'-iodobiphenyl-4-yl)-9H-carbazole in a yield of 89%.

[Step 2]

Synthesis of 4-[N-(biphenyl-4-yl)-N-phenylamino]phenylboronic acid (i) Synthesis of 4-phenyltriphenylamine A synthesis scheme (C-2) of 4-phenyltriphenylamine is shown below.

is concentrated to give a solid. The solid was recrystallized from a mixed solvent of chloroform and hexane to give 18 g of the target substance, powdery light brown solid of 4-phenyltriphenylamine in a yield of 95%.

(ii) Synthesis of 4-bromo-4'-phenyltriphenylamine

A synthesis scheme (C-3) of 4-bromo-4'-phenyltriphenylamine is shown below.

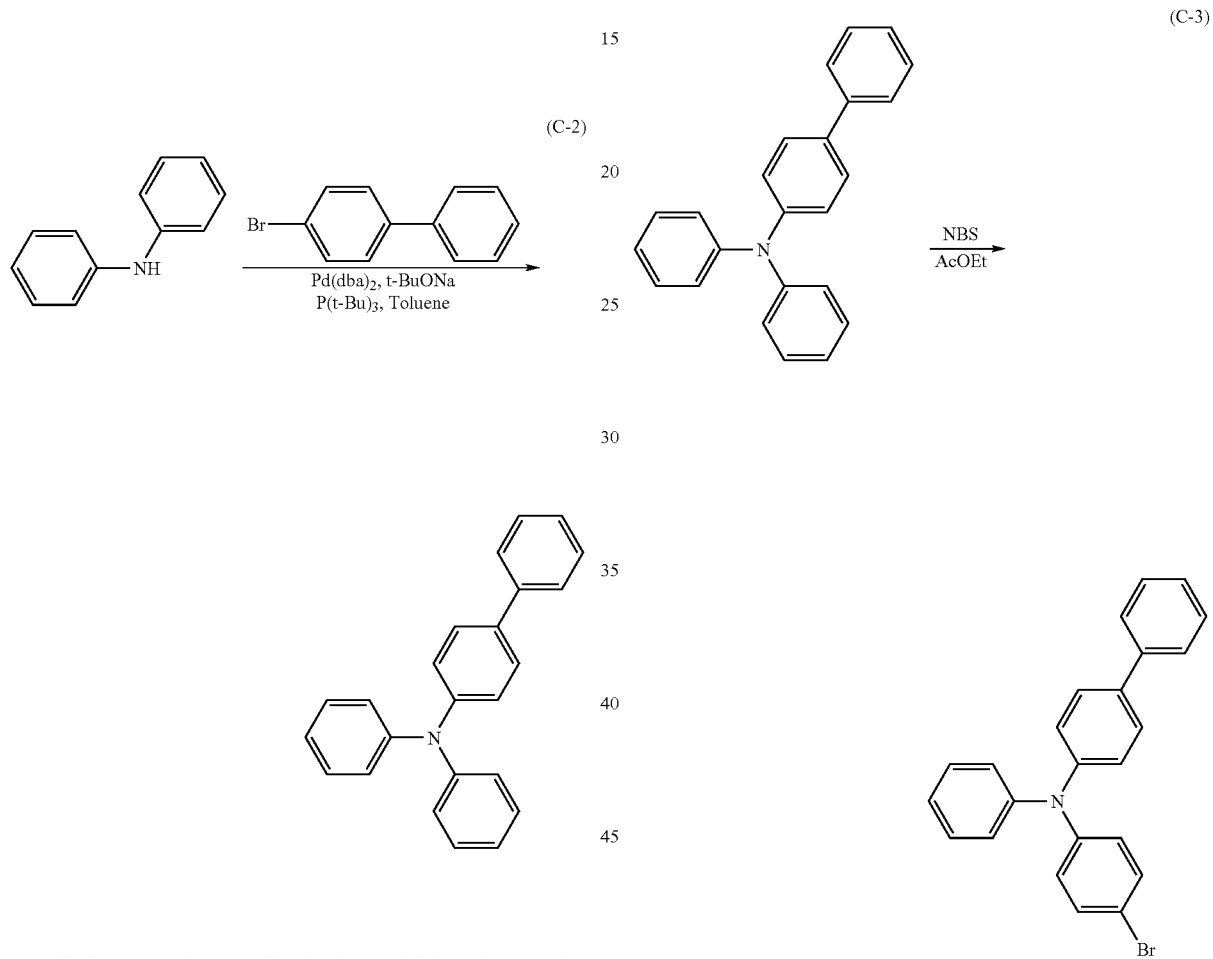

Initially, 14 g (59 mmol) of 4-bromobiphenyl, 10 g (59 mmol) of diphenylamine, 11 g (118 mmol) of sodium tert-butoxide, 0.30 g (0.52 mmol) of bis(dibenzylideneacetone) palladium(0) were put in a 100 mL three-neck flask, and the atmosphere of the flask was substituted by nitrogen. Then, 100 mL of toluene and 0.50 mL of tri(tert-butyl)phosphine (10 wt % hexane solution) were added to this mixture. This mixture was stirred under reduced pressure so as to be deaerated. After deaeration, this mixture was heated and stirred at 80° C. for 5 hours. After stirring, toluene was added to this mixture, and the suspension was washed with a saturated sodium hydrogen carbonate solution, and a saturated saline. Then, magnesium sulfate was added into the organic layer for drying. The mixture was subjected to suction filtration through Celite (produced by Wako Pure Chemical Industries, Ltd., Catalog No. 531-16855), alumina, and Florisil (produced by Wako Pure Chemical Industries, Ltd., Catalog No. 540-00135) and a filtrate was obtained. The obtained filtrate 10 g (31 mmol) of 4-phenyltriphenylamine was put in a 500 mL three-neck flask and 300 mL of ethyl acetate was added thereto. The mixture was stirred at room temperature. Then, 5.5 g (31 mmol) of N-bromo succinimide (abbreviation: NBS) was added to this solution in portions, and the mixture solution was stirred for 24 hours. After stirring, the solution was washed with a saturated sodium hydrogen carbonate solution, and a saturated saline in this order. After washing, magnesium sulfate was added to the organic layer for drying. After drying, the mixture was subjected to suction filtration to remove the magnesium sulfate, and thus a filtrate was obtained. The obtained filtrate was concentrated and dried to give 12 g of the target substance, powdery light brown solid of 4-bromo-4'-phenyltriphenylamine in a yield of 97%.

95

(iii) Synthesis of 4-[N-(biphenyl-4-yl)-N-phenylamino]phenylboronic acid

A synthesis scheme (C-4) of 4-[N-(biphenyl-4-yl)-N-phenylamino]phenylboronic acid is shown below.

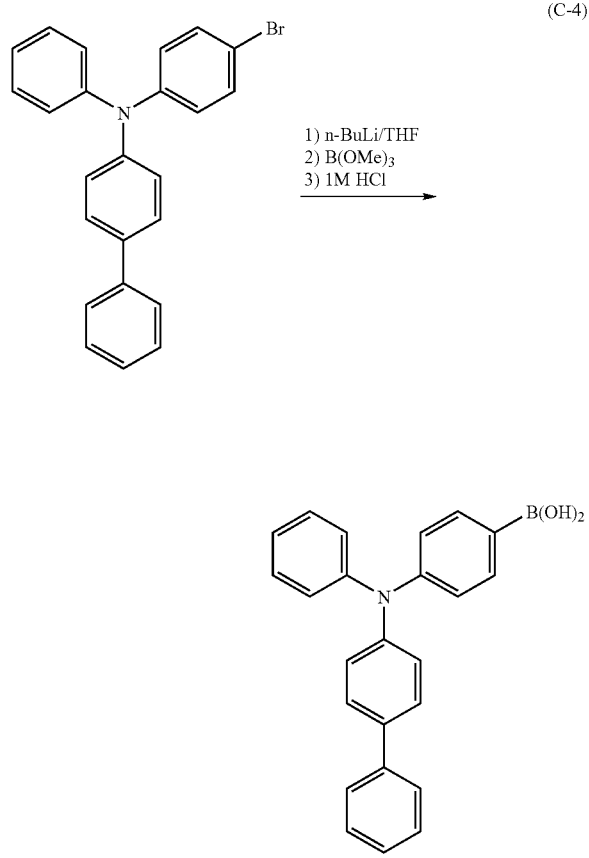

In a 300-mL three-neck flask, 7.0 g (18 mmol) of 4-bromo-4'-phenyltriphenylamine was put, and the atmosphere in the flask was substituted by nitrogen. Then, 80 mL of tetrahydrofuran (abbreviation: THF) was added thereto, and the mixture was stirred at −78° C. for 10 minutes. After that, 13 mL (21 mmol) of an n-butyllithium hexane solution (1.63 mol/L) was dropped into this solution from a syringe, and the solution was stirred at −78° C. for 1 hour. After a certain time, 3.5 mL of trimethyl borate was added to the reaction mixture and the mixture was stirred at −78° C. for 1 hour, then stirred for 24 hours while changing the temperature from −78° C. to room temperature. After stirring, 100 mL of 1M dilute hydrochloric acid was added to the solution, and the mixture was stirred at room temperature for 1 hour. After stirring, ethyl acetate was added to this solution for extraction. After extraction, the extract was washed with a saturated saline. After washing, magnesium sulfate was added to the extract for drying. After the drying, magnesium sulfate was removed by suction filtration to give a filtrate. The obtained filtrate was concentrated and recrystallized from a mixed solvent of chloroform and hexane to give 4.0 g of the target substance, 4-[N-(biphenyl-4-yl)-N-phenylamino]phenylboronic acid in a yield of 61%.

96

[Step 3] Synthesis of YGTA1BP

A synthesis scheme (C-5) of YGTA1BP is shown below.

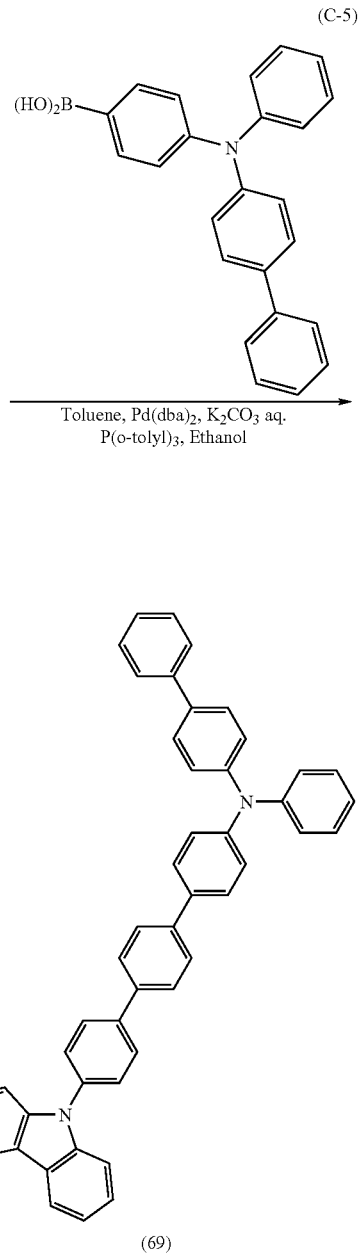

1.1 g (2.5 mmol) of 9-(4'-iodobiphenyl-4-yl)-9H-carbazole, 0.92 g (2.51 mmol) of 4-[N-(biphenyl-4-yl)-N-phenylamino]phenylboronic acid, 0.010 g (0.045 mmol) of palladium(0) acetate, and 0.10 g (0.33 mmol) of tri(o-tolyl)phosphine were put in a 100 mL three-neck flask, and 10 mL of 2.0 mol/L potassium carbonate aqueous solution, 30 mL of toluene and 5 mL of ethanol were added to the mixture. This mixture was deaerated while being stirred under reduced pressure, and the atmosphere in the flask was substituted by nitrogen. Then, it was heated and stirred at 90° C. for 5 hours. After stirring, toluene was added to the reaction mixture, and the organic layer and the aqueous layer of the suspension were separated. After separation, the organic layer was washed with a saturated sodium hydrogen carbonate solution and a saturated saline solution. Magnesium sulfate was added to the organic layer for drying. After drying, the mixture was subjected to suction filtration through Celite, alumina, and then Florisil to give a filtrate. The obtained filtrate was concentrated, and purified by silica gel column chromatography. The column chromatography was performed by, first, using a mixture solvent of toluene:hexane=1:9 as a developing solvent, and then using a mixture solvent of toluene:hexane=2:3 as another developing solvent. The resulting fraction was concentrated to give a solid, and the solid was recrystallized from a mixed solvent of chloroform and hexane, so that 0.80 g of the target substance, a powdery white solid was obtained in a yield of 50%.

0.80 g of the obtained white solid was sublimated and purified by a train sublimation method. The sublimation purification was carried out under reduced pressure of 7.0 Pa, with a flow rate of argon at 3 mL/min, at 315° C. for 15 hours. After sublimation purification, 0.62 g of the target substance was obtained in a yield of 78%.

This compound was identified as N-(biphenyl-4-yl)-4'''-(9H-carbazol-9-yl)-N-phenyl-[1,1',4',1'']terphenyl-4-amine (abbreviation: YGTA1BP) by a nuclear magnetic resonance (NMR) measurement.

The $^1$H-NMR data on this compound is shown.

$^1$H NMR (CDCl$_3$, 300 MHz): δ=7.05-7.12 (m, 1H), 7.18-7.25 (m, 6H), 7.27-7.36 (m, 5H), 7.39-7.63 (m, 12H), 7.66 (d, J=8.3 Hz, 2H), 7.70-7.80 (m, 4H), 7.87 (d, J=7.8 Hz, 2H), 8.16 (d, J=7.8 Hz, 2H).

Figure 11A:
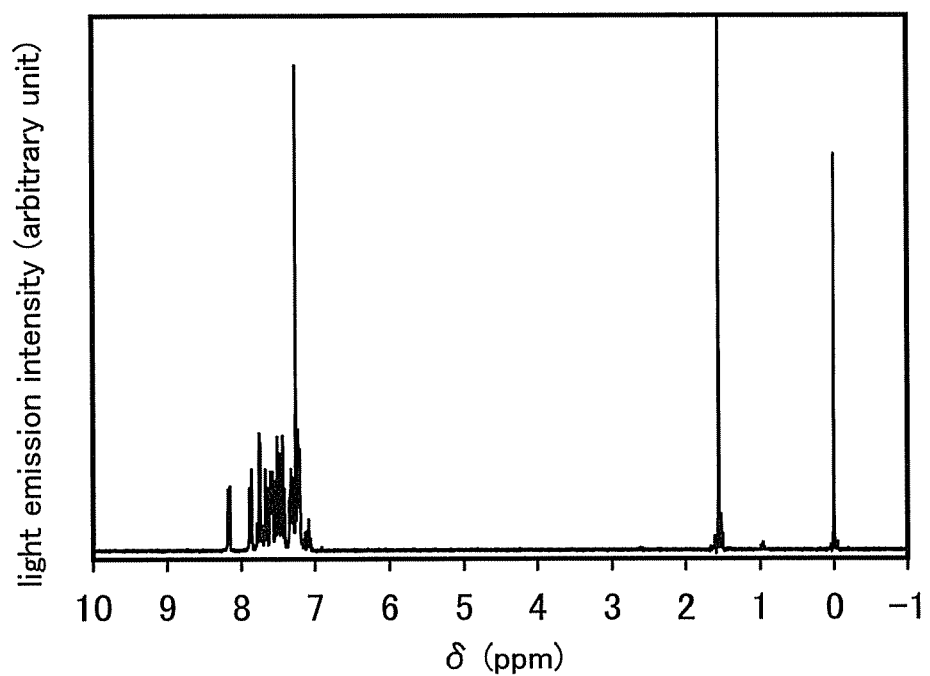
FIGS. 11A and 11B are $^1$H-NMR charts of N-(biphenyl-4-yl)-4"-(9H-carbazol-9-yl)-N-phenyl-[1,1',4',1"]terphenyl-4-amine (abbreviation: YGTA1BP)
Figure 11B:
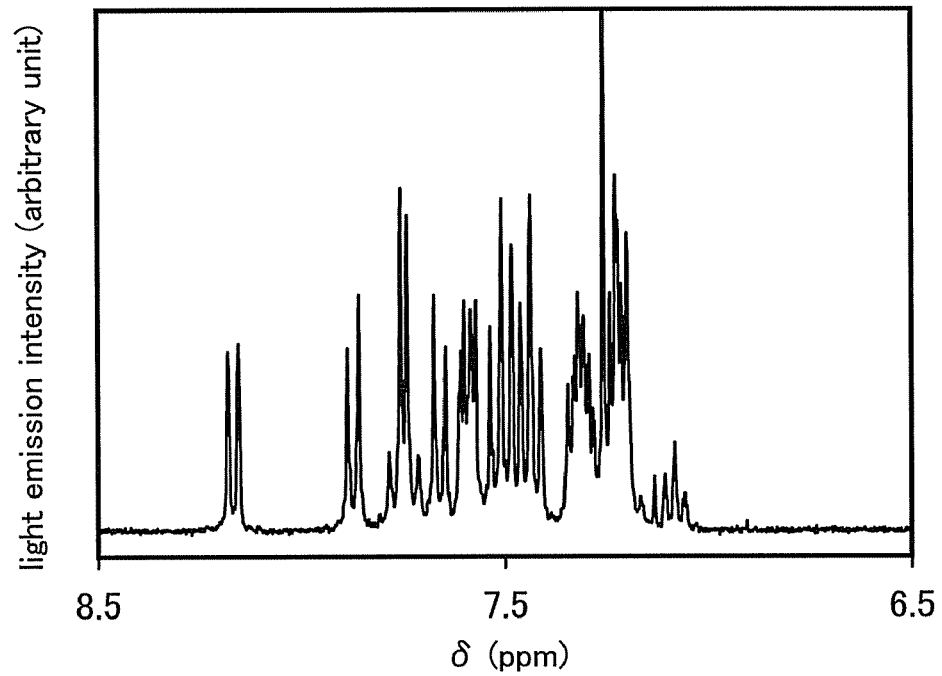

FIGS. 11A and 11B show $^1$H NMR charts. FIG. 11B is a chart showing an enlarged part of the range from 6.5 ppm to 8.5 ppm in FIG. 11A.

Figure 12A:
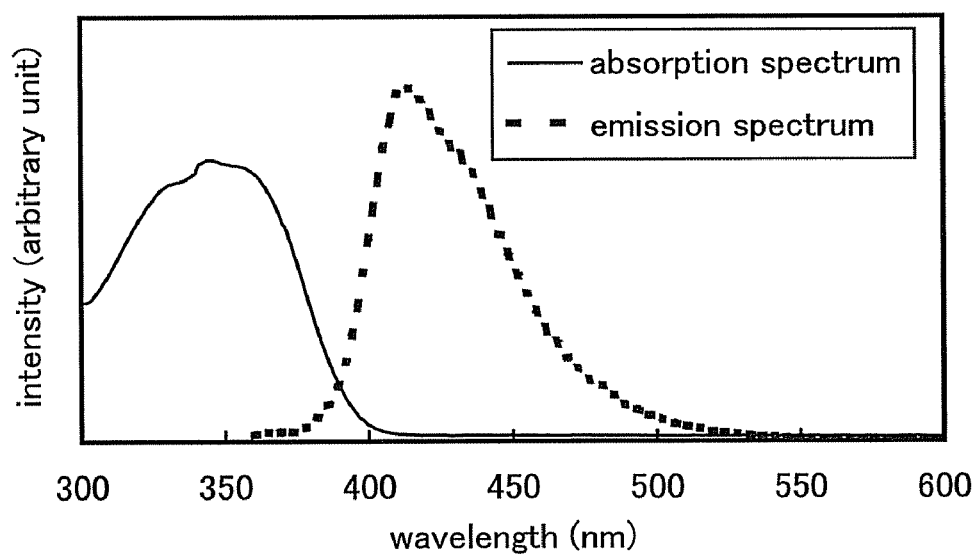
FIGS. 12A and 12B show an absorption spectrum and an emission spectrum of N-(biphenyl-4-yl)-4"-(9H-carbazol-9-yl)-N-phenyl-[1,1',4',1"]terphenyl-4-amine (abbreviation: YGTA1BP)
Figure 12B:
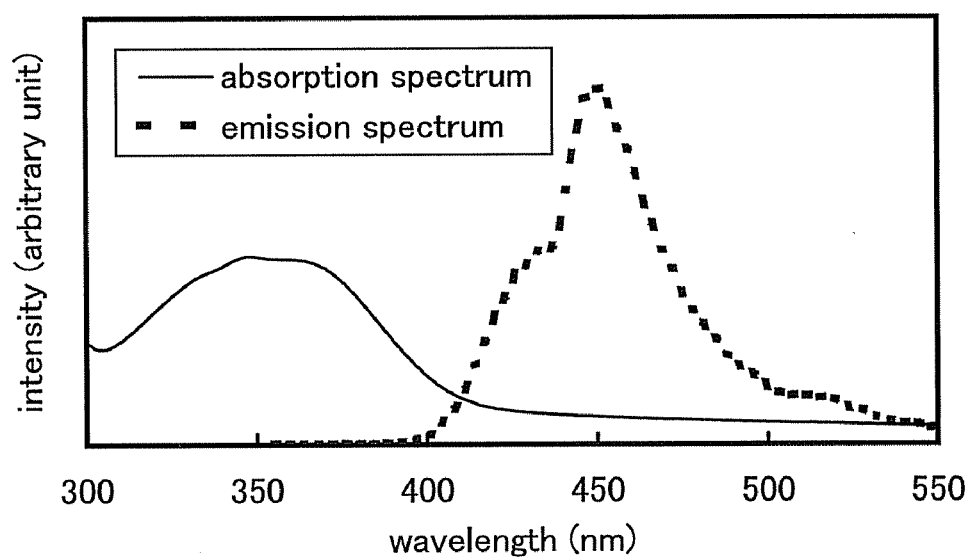

FIG. 12A shows an absorption spectrum and an emission spectrum of a toluene solution of YGTA1BP. FIG. 12B shows an absorption spectrum and an emission spectrum of the thin film of YGTA1BP. In FIGS. 12A and 12B, the horizontal axis indicates a wavelength (nm) and the vertical axis indicates light emission intensity or absorption intensity (arbitrary unit), and the absorption spectrum is shown by the solid line and the emission spectrum is shown by the broken line. The measurement of the absorption spectrum was conducted by using a UV-visible spectrophotometer (V-550, manufactured by JASCO Corporation). Samples were formed in such a way that the solution was put into a quartz cell and a thin film was deposited on a quartz substrate. Absorption spectra of the samples from which the absorption spectrum of quartz is subtracted are shown in FIGS. 12A and 12B. Absorption was observed around 355 nm in the sample in the toluene solution, and absorption was observed around 348 nm in the sample of the thin film. FIGS. 12A and 12B show that the maximum emission wavelengths of YGTA1BP in the toluene solution and of the thin film were 415 nm (excitation wavelength: 340 nm) and 449 nm (excitation wavelength: 343 nm), respectively.

The HOMO level of YGTA1BP in the thin film state which was measured by a photoelectron spectrometer (AC-2, manufactured by Riken Keiki Co., Ltd.) under air was −5.51 eV. The absorption edge was obtained from Tauc plot using data on the absorption spectrum of the thin film of YGTA1BP in FIGS. 12A and 12B. The absorption edge was regarded as an optical energy gap, and the energy gap was estimated to be 3.11 eV. Thus, a LUMO level is −2.40 eV.

EXAMPLE 2

Figure 13:
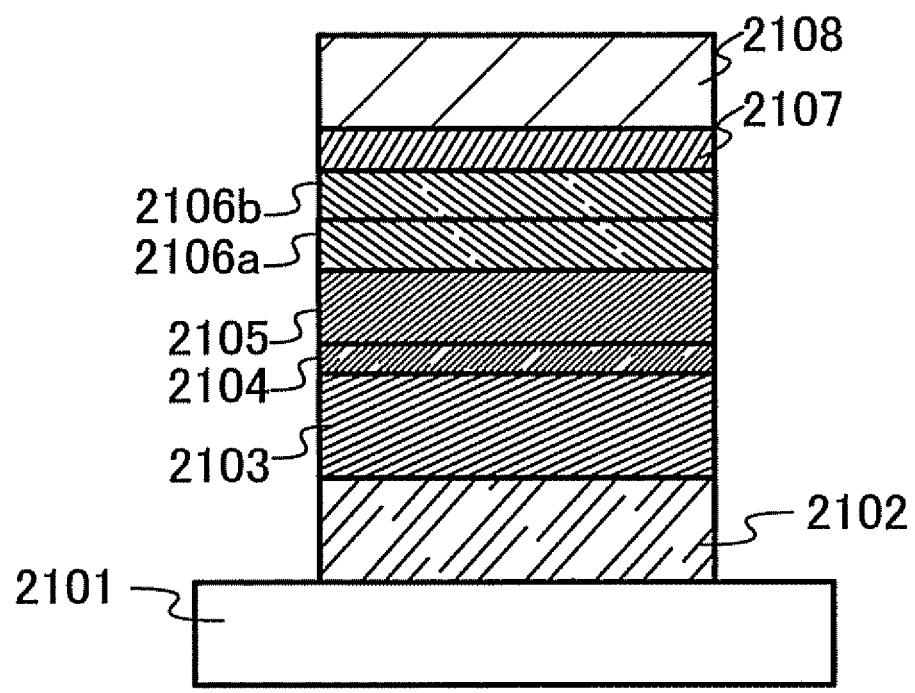
FIG. 13 illustrates a light-emitting element fabricated in Example.

In Example 2, a light-emitting element of one embodiment of the present invention is described using FIG. 13. Chemical formulae of materials used in this example are shown below.

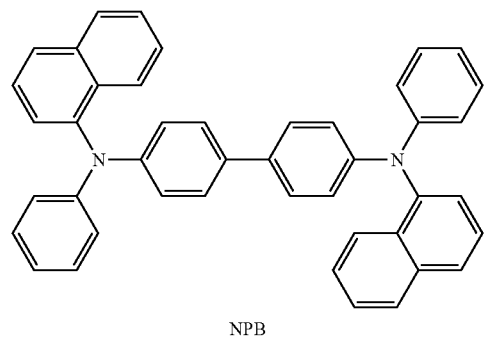

NPB

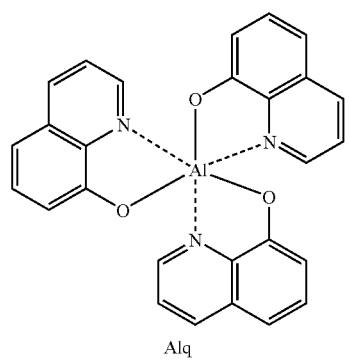

Alq

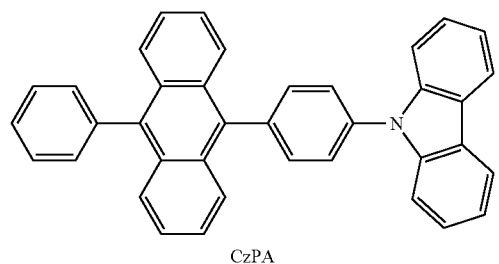

CzPA

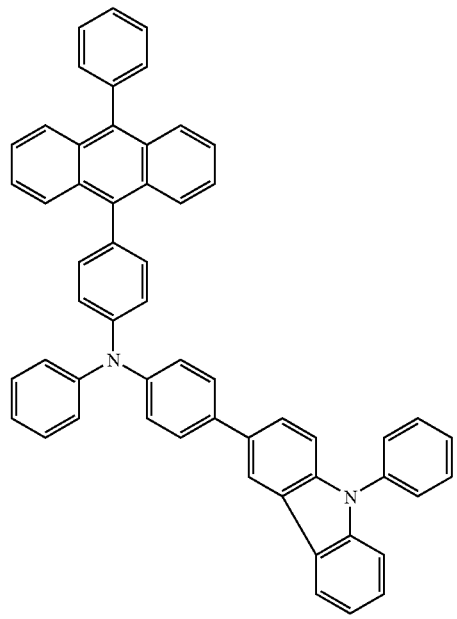

PCBAPA

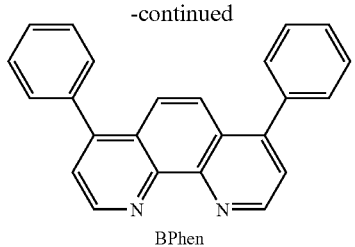
BPhen (Light-Emitting Element 1)

A first electrode 2102 was formed on a glass substrate 2101 by sputtering using indium tin oxide containing silicon oxide. The thickness of the first electrode 2102 was 110 nm. The area of the first electrode was 2 mm×2 mm.

Next, the substrate on which the first electrode 2102 was formed was fixed to a substrate holder provided in a vacuum evaporation apparatus so that a surface of the substrate on which the first electrode 2102 was formed faced down. Subsequently, after the pressure of the vacuum evaporation apparatus was reduced to approximately $10^{-4}$ Pa, a layer 2103 including a composite of an organic compound with an inorganic compound was formed on the first electrode 2102 by co-evaporation of NPB and molybdenum(VI) oxide. The film thickness was 50 nm and the weight ratio between NPB and molybdenum(VI) oxide was adjusted to be 4:1 (=NPB:molybdenum oxide). Here, the co-evaporation is an evaporation method by which evaporation of a plurality of materials is performed at the same time from a plurality of evaporation sources in one chamber.

Next, a film of N-(biphenyl-4-yl)-4"-(9H-carbazol-9-yl)-N-phenyl-[1,1',4',1"]terphenyl-4-amine (abbreviation: YGTA1BP) represented by the structural formula (69) and synthesized in Example 1 was formed to a thickness of 10 nm on the layer 2103 including a composite material by an evaporation method using resistance heating to form a hole-transporting layer 2104.

Then, a light-emitting layer 2105 was formed to a thickness of 30 nm on the hole-transporting layer 2104 by co-evaporation of 9-[4-(N-carbazolyl)]phenyl-10-phenylanthracene (abbreviation: CzPA) and 4-(10-phenyl-9-anthryl)-4'-(9-phenyl-9H-carbazol-3-yl)triphenylamine (abbreviation: PCBAPA). The weight ratio of CzPA and PCBAPA was adjusted so as to be 1:0.1 (=CzPA:PCBAPA).

After that, a first electron-transporting layer 2106a was formed on the light-emitting layer 2105 by depositing Alq to a thickness of 10 nm by an evaporation method using resistance heating.

Moreover, a 20-nm-thick film of bathophenanthroline (abbreviation: BPhen) was formed as a second electron-transporting layer 2106b on the first electron-transporting layer 2106a by an evaporation method using resistance heating.

Moreover, an electron-injecting layer 2107 was formed to a thickness of 1 nm by depositing lithium fluoride on the second electron-transporting layer 2106b by an evaporation method using resistance heating.

Lastly, a second electrode 2108 was formed with a 200-nm-thick film of aluminum on the electron-injecting layer 2107 by an evaporation method using resistance heating. In this manner, the light-emitting element 1 was fabricated.

(Comparative light-emitting element 1) A 10-nm-thick film of NPB was formed as the hole-transporting layer 2104 of the comparative light-emitting element 1. Other portions than the hole-transporting layer 2104 were formed similar to those of the light-emitting element 1.

(Comparative light-emitting element 2)

As the hole-transporting layer 2104 of the comparative light-emitting element 2, a 10-nm-thick film of 4-(carbazol-9-yl)phenyl-4'-phenyltriphenylamine (abbreviation: YGA1BP) that has a YGA skeleton and is represented by a structure formula (131) was formed. The other portions than the hole-transporting layer 2104 were formed similar to those of the light-emitting element 1.

(131)
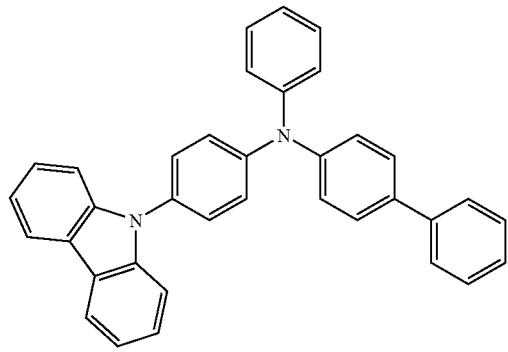

(Comparative Light-Emitting Element 3)

As the hole-transporting layer 2104 of the comparative light-emitting element 3, a 10-nm-thick film of 4-[4-(9H-carbazol-9-yl)phenyl]-4'-phenyltriphenylamine (abbreviation: YGBA1BP) that has a YGA skeleton and is represented by a structure formula (132) was formed. The other portions than the hole-transporting layer 2104 were formed similar to those of the light-emitting element 1.

(132)
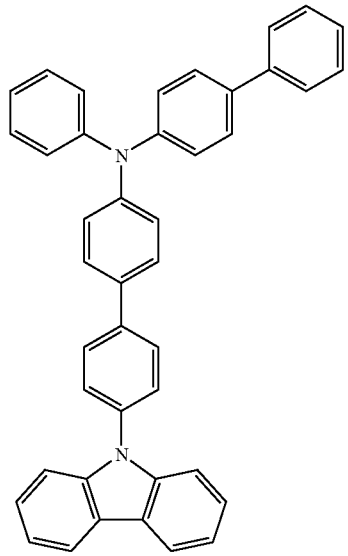

Table 1 shows element structures of the light-emitting element 1 and the comparative light-emitting elements 1 to 3 fabricated in this example. In Table 1, the mixture ratios are all represented in weight ratios.

TABLE 1

|  | First electrode 2102 | Layer including a composite material 2103 | Hole-transporting layer 2104 | Light-emitting layer 2105 | First electron-transporting layer 2106a | Second electron-transporting layer 2106b | Electron-injecting layer 2107 | Second electrode 2108 |
|---|---|---|---|---|---|---|---|---|
| Light-emitting element 1 | ITSO 110 nm | NPB:MoOx (4:1) 50 nm | YGTA1BP 10 nm | CzPA:PCBAPA (1:0.1) 30 nm | Alq 10 nm | BPhen 20 nm | LiF 1 nm | Al 200 nm |
| Comparative light-emitting element 1 | ITSO 110 nm | NPB:MoOx (4:1) 50 nm | NPB 10 nm | CzPA:PCBAPA (1:0.1) 30 nm | Alq 10 nm | BPhen 20 nm | LiF 1 nm | Al 200 nm |
| Comparative light-emitting element 2 | ITSO 110 nm | NPB:MoOx (4:1) 50 nm | YGA1BP 10 nm | CzPA:PCBAPA (1:0.1) 30 nm | Alq 10 nm | BPhen 20 nm | LiF 1 nm | Al 200 nm |
| Comparative light-emitting element 3 | ITSO 110 nm | NPB:MoOx (4:1) 50 nm | YGBA1BP 10 nm | CzPA:PCBAPA (1:0.1) 30 nm | Alq 10 nm | BPhen 20 nm | LiF 1 nm | Al 200 nm |

*The mixture ratios are all represented in weight ratios

It is observed that the fabricated light-emitting element 1 and comparative light-emitting elements 1 to 3 all exhibited an emission wavelength derived from PCBAPA of a blue light-emitting material. The CIE chromaticity coordinates of all the light-emitting elements were (x, y)=(0.15, 0.22) approximately.

Figure 14:
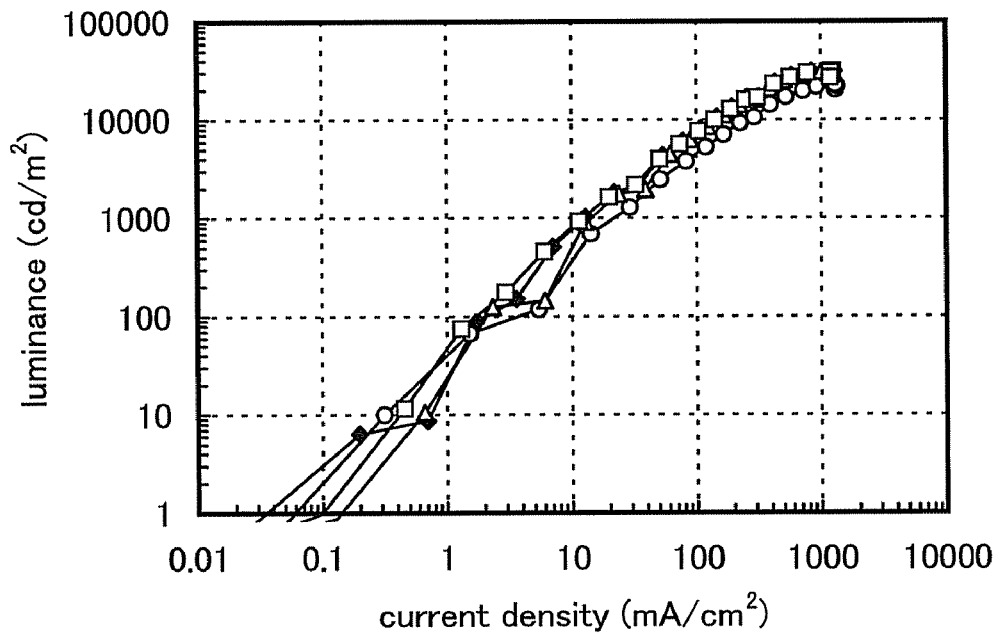
FIG. 14 shows current density vs. luminance characteristics of light-emitting elements fabricated in Example.
Figure 15:
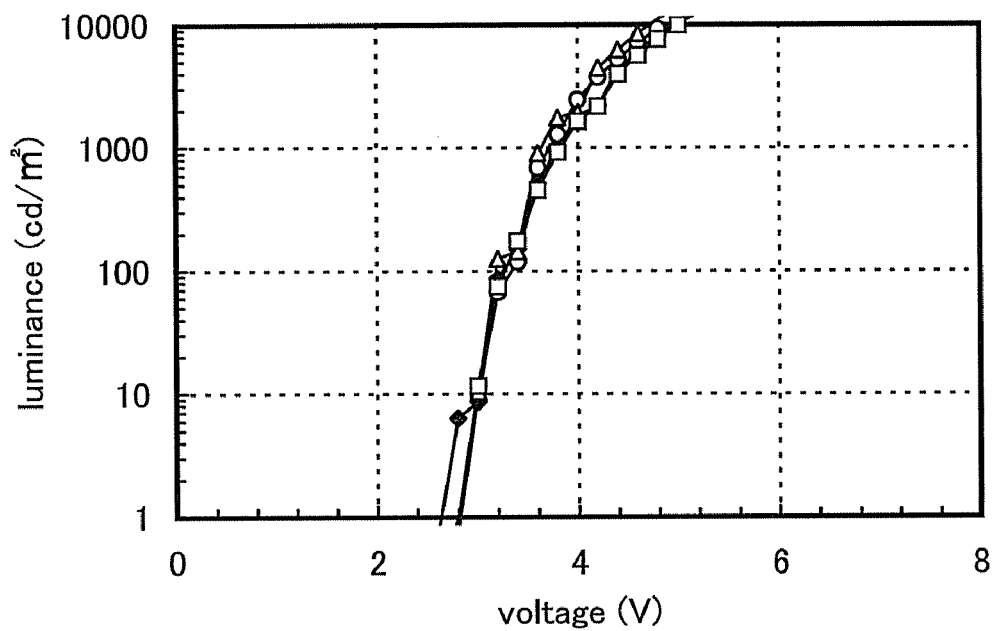
FIG. 15 shows voltage vs. luminance characteristics of the light-emitting elements fabricated in Example.
Figure 16:
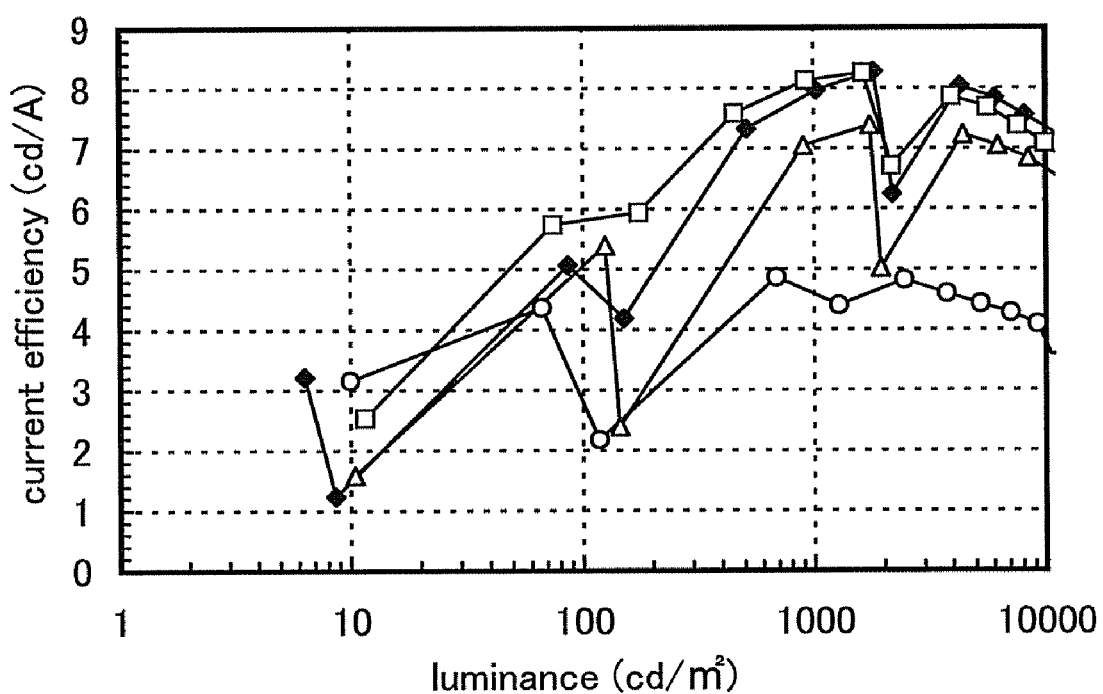
FIG. 16 shows luminance vs. current efficiency characteristics of the light-emitting elements fabricated in Example.

FIG. 14 shows current density vs. luminance characteristics of the light-emitting element 1 and the comparative light-emitting elements 1 to 3. In FIG. 14, the horizontal axis represents current density (mA/cm$^2$) and the vertical axis represents luminance (cd/m$^2$). FIG. 15 shows voltage vs. luminance characteristics thereof. In FIG. 15, the horizontal axis represents applied voltage (V) and the vertical axis represents emission luminance (cd/m$^2$). FIG. 16 shows luminance vs. current efficiency characteristics thereof. In FIG. 16, the horizontal axis represents emission luminance (cd/m$^2$) and the vertical axis represents current efficiency (cd/A). In FIG. 14 to FIG. 16, the bold lozenge (♦), the open circle (○), the open triangle (Δ), and the open square (□) correspond to the light-emitting element 1, the comparative light-emitting element 1, the comparative light-emitting element 2, and the comparative light-emitting element 3, respectively.

In the light-emitting element 1, a voltage necessary for a luminance of 1026 cd/m$^2$ was 3.8 V, and a current flowing at that time was 0.52 mA (current density was 12.9 mA/cm$^2$). The current efficiency at that time was 8.0 cd/A.

In the comparative light-emitting element 1, a voltage necessary for a luminance of 690 cd/m$^2$ was 3.6 V, and a current flowing at that time was 0.57 mA (current density was 14.2 mA/cm$^2$). The current efficiency at that time was 4.9 cd/A.

In the comparative light-emitting element 2, a voltage necessary for a luminance of 910 cd/m$^2$ was 3.6 V, and a current flowing at that time was 0.51 mA (current density was 12.8 mA/cm$^2$). The current efficiency at that time was 7.0 cd/A.

In the comparative light-emitting element 3, a voltage necessary for a luminance of 920 cd/m$^2$ was 3.8 V, and a current flowing at that time was 0.46 mA (current density was 11.4 mA/cm$^2$). The current efficiency at that time was 8.1 cd/A.

From the above, it is found that the light-emitting element using an aromatic amine compound of one embodiment of the present invention exhibited high current efficiency, similar to the comparative light-emitting element 2 using a compound YGA1BP having a YGA skeleton or the comparative light-emitting element 3 using a compound YGBA1BP having a YGA skeleton.

Figure 17:
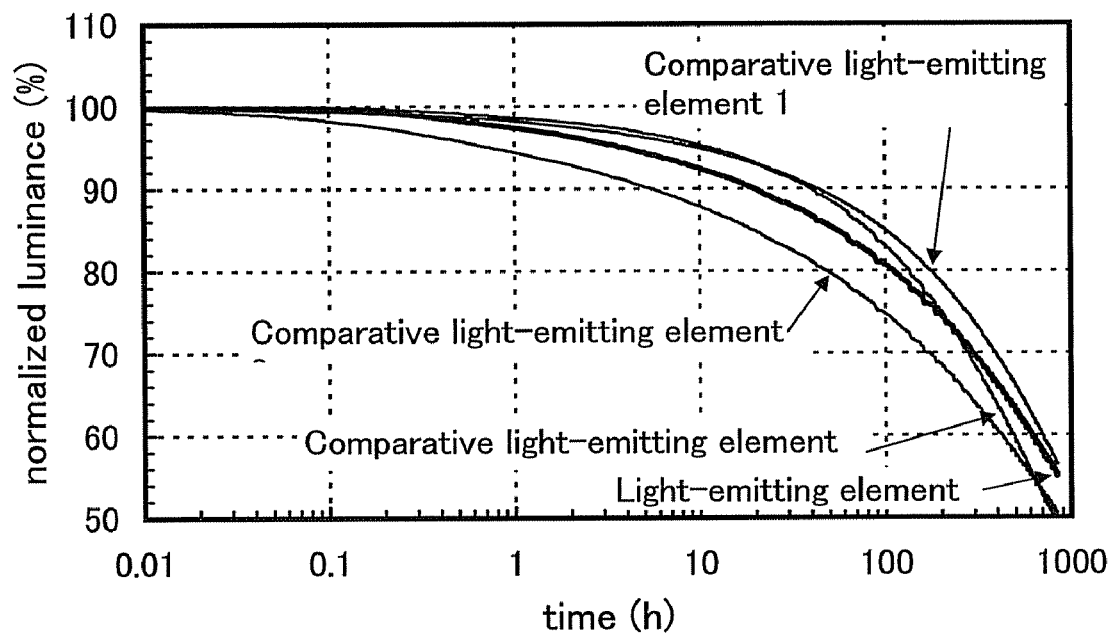
FIG. 17 shows time dependence of normalized luminance of the light-emitting elements fabricated in Example.

FIG. 17 is a graph showing time dependence of normalized luminance of light-emitting element 1 and the comparative light-emitting elements 1 to 3. The time dependence of normalized luminance is a measurement result of luminance dependent on time obtained under the conditions that the light-emitting element 1 was driven under a constant current density at an initial luminance of approximately 1000 cd/m$^2$ and the change in luminance was normalized.

As shown in FIG. 17, the luminance of the light-emitting element 1 hardly deteriorates with time as compared with the comparative light-emitting element 2 and the comparative light-emitting element 3, and has a long life time similar to the comparative light-emitting element 1.

The above description reveals that by forming a hole-transporting layer using an aromatic amine compound of one embodiment of the present invention, a light-emitting element having excellent element characteristics and long lifetime can be formed.

EXAMPLE 3

Figure 18:
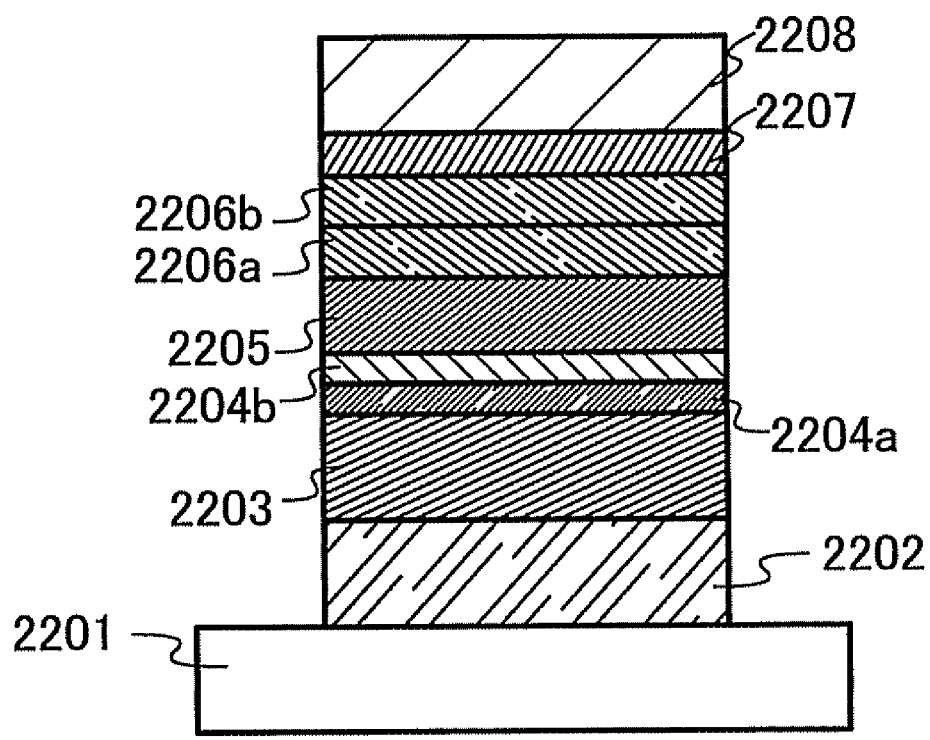
FIG. 18 illustrates a light-emitting element fabricated in Example.

In Example 3, another element structure of a light-emitting element which is different from that of Example 2 is described with reference to FIG. 18.

(Light-Emitting Element 2)

A first electrode 2202 was formed on a glass substrate 2201 by sputtering using indium tin oxide containing silicon oxide. The thickness of the first electrode 2202 was 110 nm. The area of the first electrode was 2 mm×2 mm.

Next, the substrate on which the first electrode 2202 was formed was fixed to a substrate holder provided in a vacuum evaporation apparatus so that a surface of the substrate on which the first electrode 2202 was formed faced down. Then, after reducing the pressure of the vacuum evaporation apparatus to about 10$^{-4}$ Pa, a layer 2203 including a composite material of an organic compound and an inorganic compound was formed on the first electrode 2202 by co-depositing NPB and molybdenum(VI) oxide. The film thickness is 50 nm and the weight ratio between NPB and molybdenum(VI) oxide is adjusted to be 4:1 (=NPB:molybdenum oxide). Further, the co-evaporation is an evaporation method by which evaporation of a plurality of materials is performed at the same time from a plurality of evaporation sources in one chamber.

Next, a film of N-(biphenyl-4-yl)-4"-(9H-carbazol-9-yl)-N-phenyl-[1,1',4',1"]terphenyl-4-amine (abbreviation: YGTA1BP) represented by the structural formula (69) was formed to a thickness of 10 nm on the layer 2203 including a composite material by an evaporation method using resistance heating to form a first hole-transporting layer 2204a.

Then, a 10-nm-thick film of NPB was formed on the first hole-transporting layer 2204a to form a second hole-transporting layer 2204b by an evaporation method using resistance heating.

Then, a light-emitting layer 2205 was formed to a thickness of 30 nm on the second hole-transporting layer 2204b by co-evaporation of 9-[4-(N-carbazolyl)]phenyl-10-phenylanthracene (abbreviation: CzPA) and 4-(10-phenyl-9-anthryl)-4'-(9-phenyl-9H-carbazol-3-yl)triphenylamine (abbreviation PCBAPA). The weight ratio of CzPA and PCBAPA was adjusted so as to be 1:0.1 (=CzPA:PCBAPA).

After that, a first electron transporting layer 2206a was formed on the light-emitting layer 2205 by depositing Alq to a thickness of 10 nm by an evaporation method using resistance heating.

Moreover, a 20-nm-thick film of bathophenanthroline (abbreviation: BPhen) was formed as a second electron-transporting layer 2206b on the first electron-transporting layer 2206a by an evaporation method using resistance heating. Moreover, an electron-injecting layer 2207 was formed to a thickness of 1 nm by depositing lithium fluoride on the second electron-transporting layer 2206b by an evaporation method using resistance heating.

Lastly, a 200-nm-thick film of aluminum was deposited on the electron-injecting layer 2207 by evaporation using resistance heating to form a second electrode 2208. In this manner, the light-emitting element 2 was fabricated. Table 2 shows the element structure of the light-emitting element 2 fabricated in this example. In Table 2, the mixture ratios are all represented in weight ratios.

It is observed that the fabricated light-emitting element 2 exhibited an emission wavelength derived from PCBAPA which is a blue light-emitting material. The CIE chromaticity coordinates of the light-emitting element was (x, y)=(0.15, 0.22).

Figure 19:
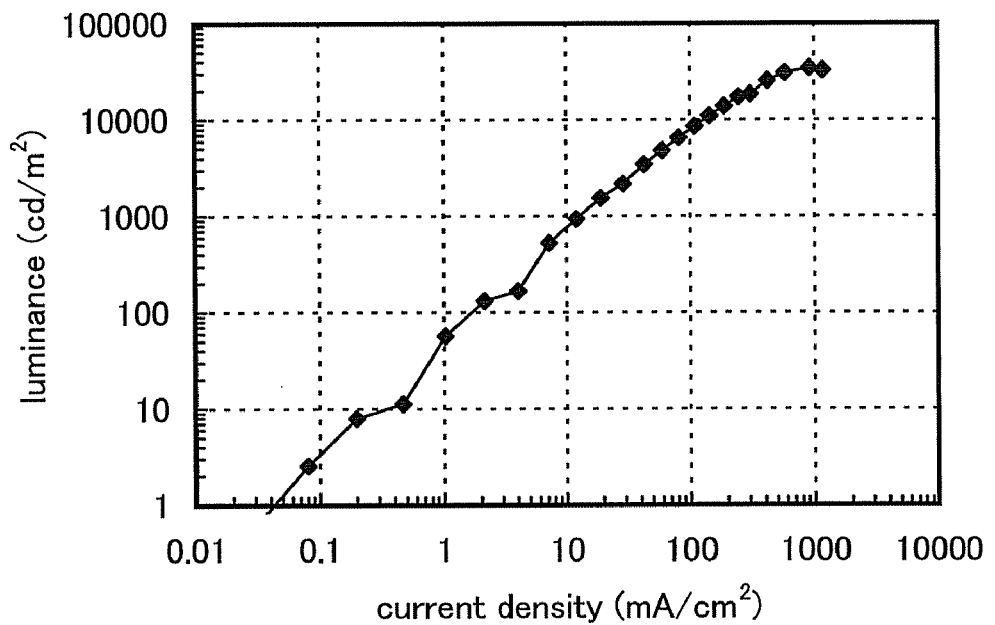
FIG. 19 shows current density vs. luminance characteristics of the light-emitting element fabricated in Example.
Figure 20:
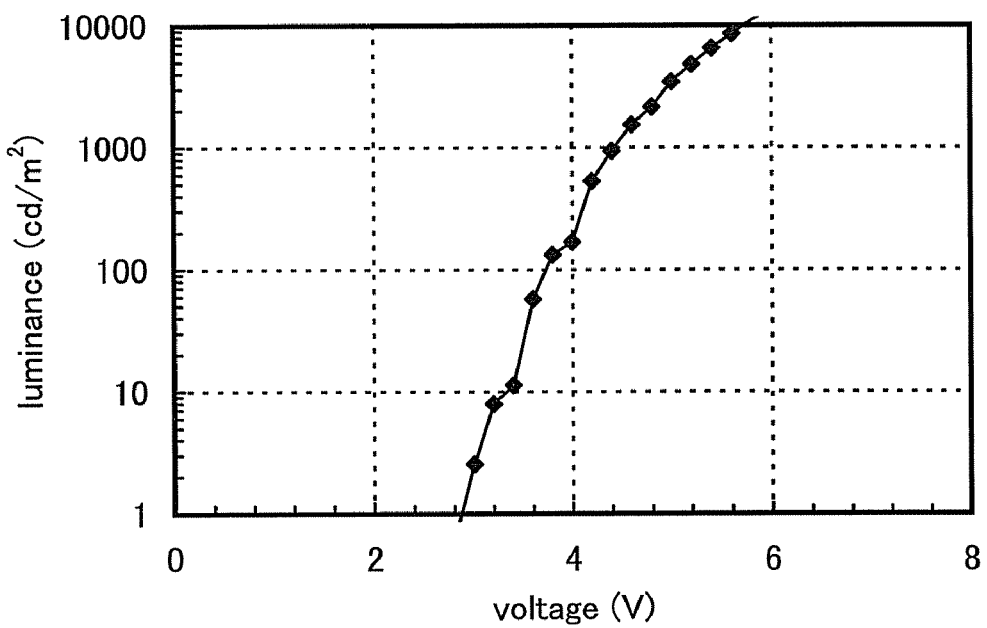
FIG. 20 shows the voltage vs. luminance characteristics of the light-emitting element fabricated in Example.
Figure 21:
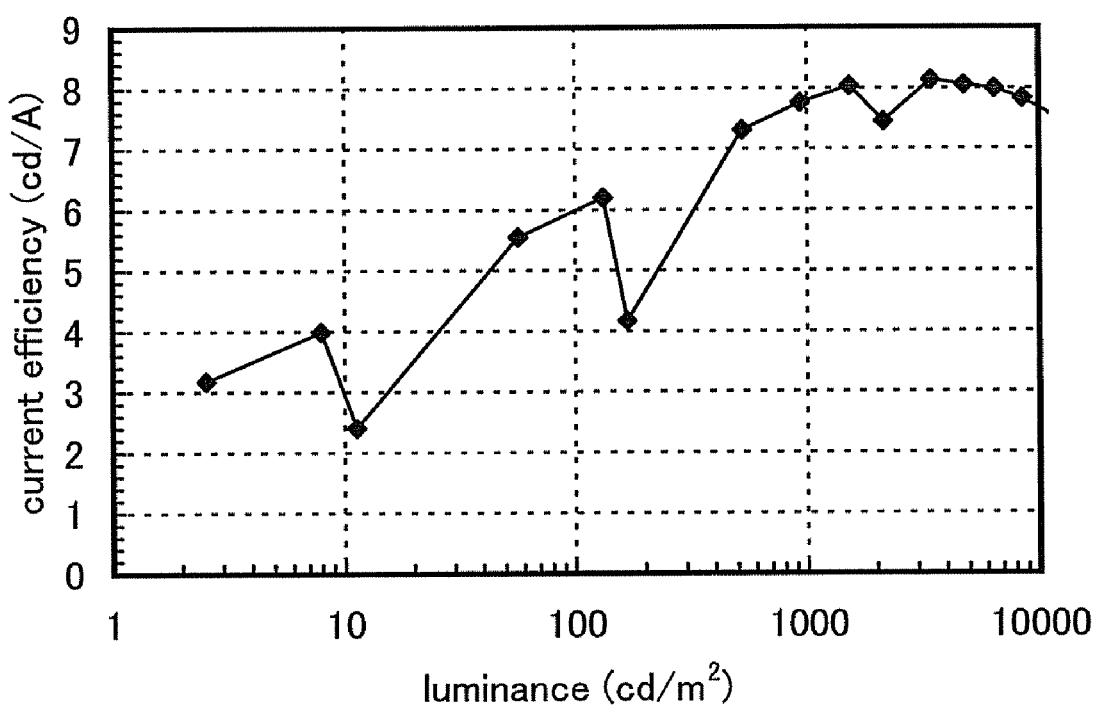
FIG. 21 shows luminance vs. current efficiency characteristics of the light-emitting element fabricated in Example.

FIG. 19 shows current density vs. luminance characteristics of the light-emitting element 2. In FIG. 19, the horizontal axis represents current density (mA/cm$^2$) and the vertical axis represents luminance (cd/m$^2$). FIG. 20 shows voltage vs. luminance characteristics thereof. In FIG. 20, the horizontal axis represents applied voltage (V) and the vertical axis represents emission luminance (cd/m$^2$). FIG. 21 shows luminance vs. current efficiency characteristics thereof. In FIG. 21, the horizontal axis represents emission luminance (cd/m$^2$) and the vertical axis represents current efficiency (cd/A).

In the light-emitting element 2, a voltage necessary for a luminance of 940 cd/m$^2$ was 4.4 V, and a current flowing at that time was 0.48 mA (current density was 12.1 mA/cm$^2$). The current efficiency at that time was 7.8 cd/A.

Figure 22:
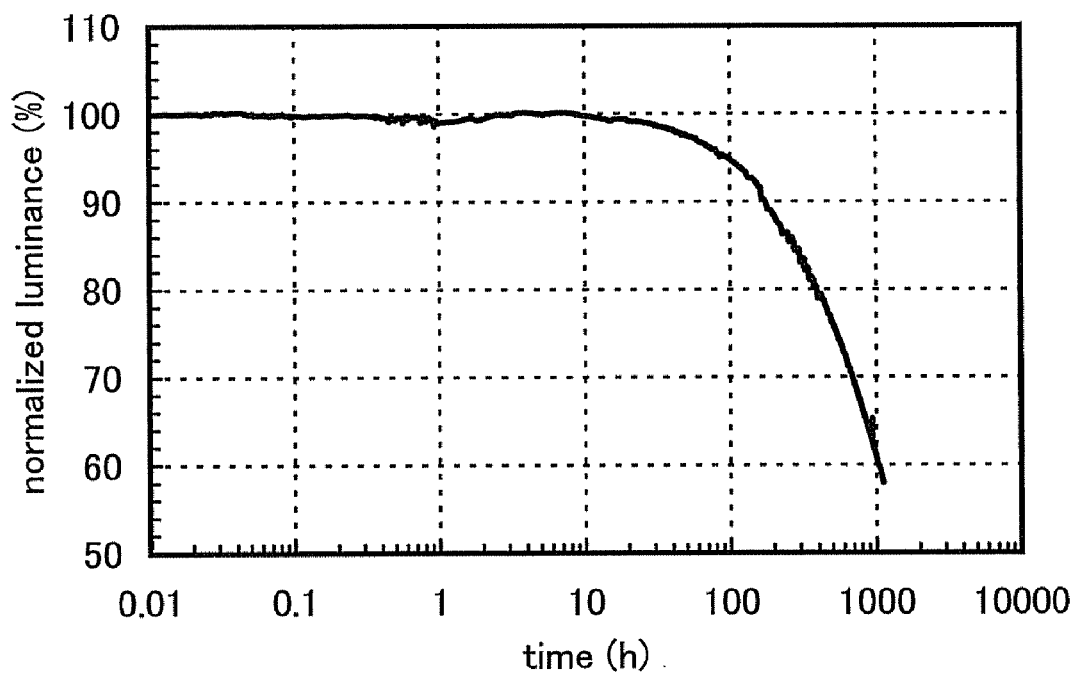
FIG. 22 shows time dependence of normalized luminance of the light-emitting element fabricated in Example.

FIG. 22 is a graph showing time dependence of normalized luminance of light-emitting element 2. As shown in FIG. 22, the luminance of the light-emitting element 2 was 58% even after driving at an initial luminance of 1000 cd/m$^2$ for 1100 hours and thus it is found that the light-emitting element 2 has a long lifetime.

The above description reveals that by forming a hole-transporting layer of a light-emitting element, using an aromatic amine compound of one embodiment of the present invention, the light-emitting element can have excellent element characteristics and long lifetime.

EXAMPLE 4

In Example 4, synthesis examples of materials used in other examples are described.

<<Synthesis example of YGBA1BP>>

A synthesis method of 4-[4-(9H-carbazol-9-yl)phenyl]4'-phenyltriphenylamine (abbreviation: YGBA1BP) represented by the structural formula (132) is described below.

TABLE 2

|  | First electrode 2202 | Layer including a composite material 2203 | First hole-transporting layer 2204a | Second hole-transporting layer 2204b | Light-emitting layer 2205 | First electron-transporting layer 2206a | Second electron-transporting layer 2206b | Electron-injecting layer 2207 | Second electrode 2208 |
| --- | --- | --- | --- | --- | --- | --- | --- | --- | --- |
| Light-emitting element 2 | ITSO 110 nm | NPB:MoOx (4:1) 30 nm | YGTA1BP 10 nm | NPB 20 nm | CzPA:PCBAPA (1:0.1) 30 nm | Alq 10 nm | BPhen 20 nm | LiF 1 nm | Al 200 nm |

*The mixture ratios are all represented in weight ratios

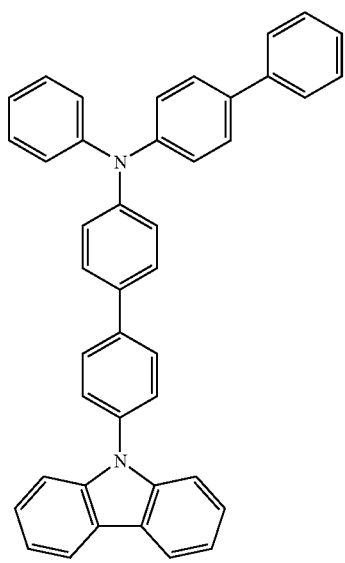

(132)

[Step 1] Synthesis of 4-phenyl-diphenylamine

A synthesis scheme (D-1) of 4-phenyldiphenylamine is shown below.

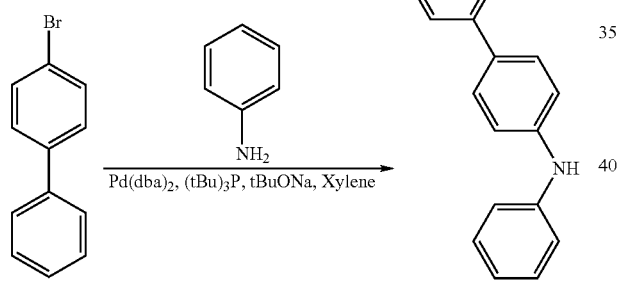

(D-1)

In a 1000-mL flask, 51 g (220 mmol) of 4-bromo-1,1'-biphenyl, 23 g (250 mmol) of aniline, 50 g (500 mmol) of sodium tert-butoxide, and 250 mg (0.4 mmol) of bis(dibenzylideneacetone)palladium(0) were put, and the atmosphere in the flask was substituted by nitrogen. 500 mL of dehydrated toluene was added to the mixture. The mixture was deaerated while being stirred under reduced pressure, and after deaeration, 3.0 mL (1.5 mmol) of tri(tert-butyl)phosphine (10 wt % hexane solution) was added thereto. This mixture was heated and stirred under a nitrogen atmosphere at 90° C. for 4.5 hours.

After the reaction, 600 mL of toluene was added to this reaction mixture, and this suspension was filtrated through Florisil and Celite. The obtained filtrate was washed with water and magnesium sulfate was added to remove water. This suspension was filtrated through Florisil and Celite to give a filtrate. The obtained filtrate was concentrated, and hexane was added thereto. The mixture was irradiated with ultrasonic waves and then allowed to precipitate 40 g of the target substance, white powder of 4-phenyl-diphenylamine in a yield of 73%.

[Step 2] Synthesis of YGBA1BP

A synthesis scheme (D-2) of YGBA1BP is shown below.

(D-2)

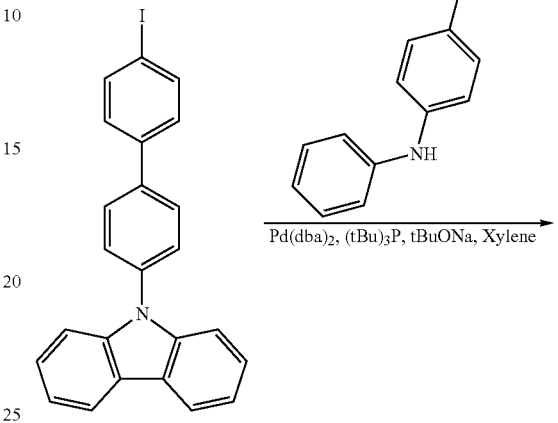

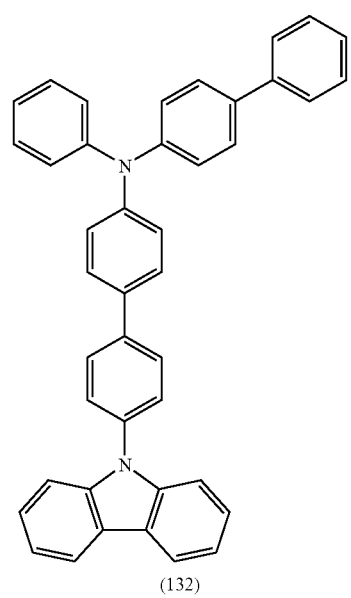

(132)

In a 100-mL three-neck flask, 1.8 g (4.0 mmol) of 9-(4'-iodobiphenyl-4-yl)-9H-carbazole obtained in Step 1 of Example 1, 1.0 g (4.0 mmol) of 4-phenyl-diphenylamine, 0.8 g (8.0 mmol) of sodium tert-butoxide, and 5.0 mg (0.01 mmol) of bis(dibenzylideneacetone)palladium(0) were put, and the atmosphere in the flask was substituted by nitrogen. Then, 40 mL of dehydrated xylene was added to this mixture. The mixture was deaerated while being stirred under reduced pressure, and after deaeration, 0.06 mL (0.03 mmol) of tri(tert-butyl)phosphine (10 wt % hexane solution) was added thereto. This mixture was stirred under a nitrogen atmosphere at 120° C. for 5 hours to be reacted.

After the reaction, 200 mL of toluene was added to this reaction mixture, and this suspension was filtrated through Florisil, alumina and Celite. Then, the obtained filtrated was washed with water, and magnesium sulfate was added to remove water. This suspension was filtrated through Florisil, alumina, and Celite to give a filtrate. The obtained filtrate was concentrated and purified by silica gel column chromatography (developing solvent:toluene:hexane=1:1). The obtained fraction was concentrated and acetone and methanol were added thereto, and the mixture was subjected to ultrasonic waves and allowed to precipitate 1.6 g of the target substance, white powder of 4-[4-(9H-carbazol-9-yl)phenyl]-4'-phenyltriphenylamine (abbreviation: YGBA1BP) in a yield of 95%.

The Rf value of the target substance by a silica gel thin layer chromatography (TLC) (developing solvent:ethyl acetate:hexane=1:10) was 0.39, that of 9-(4'-iodobiphenyl-4-yl)-9H-carbazole was 0.64, and that of 4-phenyl-diphenylamine was 0.25.

A compound that was obtained through the above Step 2 was subjected to a nuclear magnetic resonance (NMR) measurement. The $^1$H NMR data are shown below.

$^1$H NMR (CDCl$_3$, 300 MHz): δ(ppm)=7.08 (t, J=7.2 Hz, 1H), 7.20-7.62 (m, 25H), 7.78 (d, J=8.1 Hz, 2H), 8.15 (d, J=7.8 Hz, 2H).

Figure 23A:
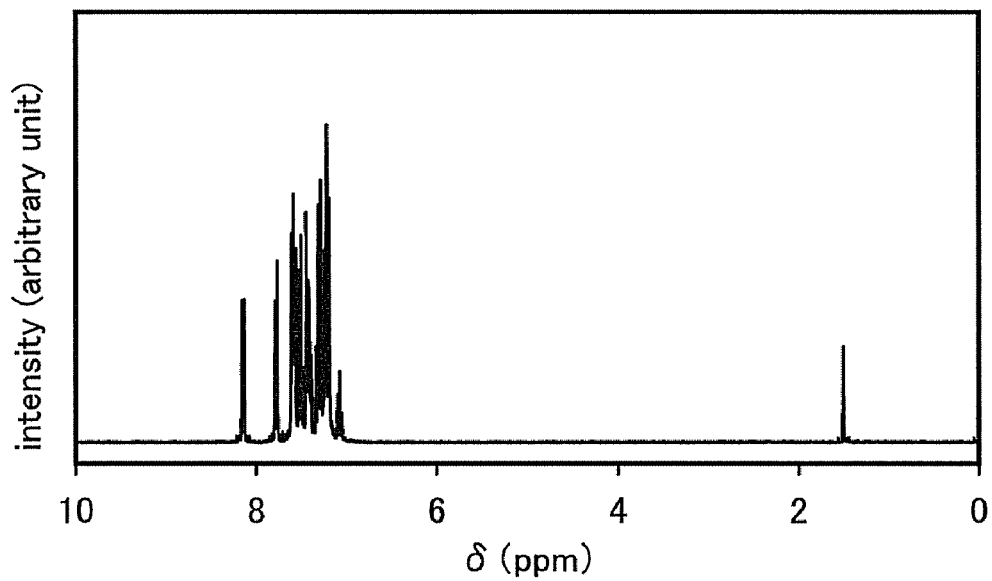
FIGS. 23A and 23B show $^1$H-NMR charts of 4-[4-(9H-carbazol-9-yl)phenyl)4'-phenyltriphenylamine (abbreviation: YGBA1BP).
Figure 23B:
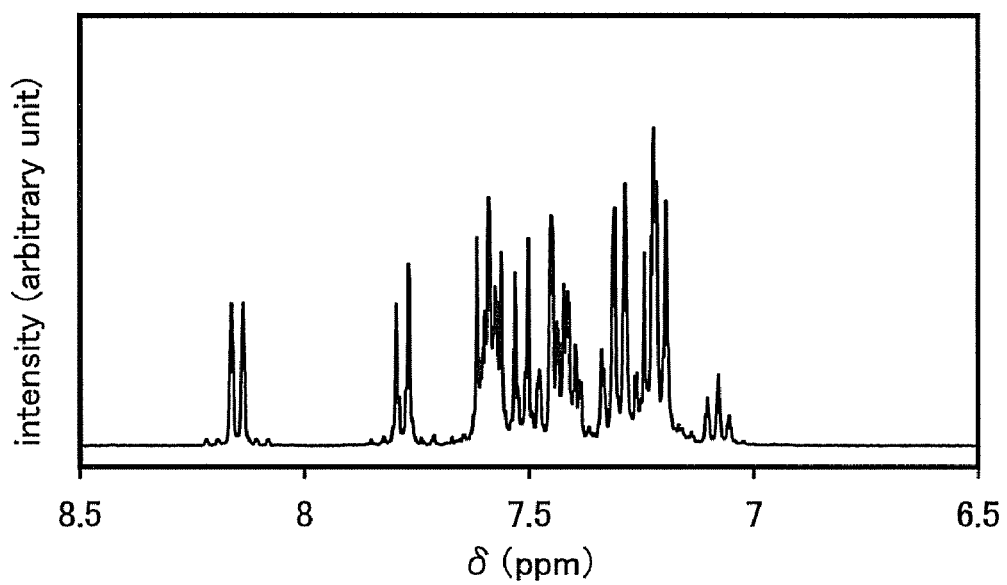

$^1$H-NMR charts are shown in FIGS. 23A and 23B. The measurement results showed that 4-[4-(9H-carbazol-9-yl) phenyl]4'-phenyltriphenylamine (abbreviation: YGBA1BP) represented by the above structural formula (132) was obtained. FIG. 23B is a chart showing an enlarged part of the range from 6.5 ppm to 8.5 ppm in FIG. 23A.

EXAMPLE 5

In Example 5, a light-emitting element that has a structure different from the structures described in Example 2 and Example 3 is described with reference to FIG. 13. As for the light-emitting element of this example, the same or similar parts as/to or parts having the same or similar functions as/to those described in Example 1 are denoted by the same reference numerals as those of Example 1, and the description of them will not be repeated. The element structure adopted in Example 5 is the same as that in Example 1 (refer to FIG. 13).

(Light-Emitting Element 3)

A light-emitting element 3 of Example 5 was formed in a similar manner to the light-emitting element 1 of Example 1, except for the layer 2103 including a composite material. The light-emitting element 3 was formed as follows. The substrate on which the first electrode 2102 was formed was fixed to a substrate holder provided in a vacuum evaporation apparatus so that a surface of the substrate on which the first electrode 2102 was formed faced down. Then, after reducing the pressure of the vacuum evaporation apparatus to about 10$^{-4}$ Pa, the layer 2103 including a composite material of an organic compound and an inorganic compound was formed on the first electrode 2102 by co-evaporating YGTA1BP and molybdenum(VI) oxide. The film thickness was 50 nm and the weight ratio between YGTA1BP and molybdenum(VI) oxide was adjusted to be 4:1 (=YGTA1BP: molybdenum oxide).

The element structure of the light-emitting element 3 fabricated in this example is shown in Table 3. In Table 3, the mixture ratios are all represented in weight ratios.

It is observed that the fabricated light-emitting element 3 exhibited an emission wavelength derived from PCBAPA which is a blue light-emitting material. The CIE chromaticity coordinates of the light-emitting element was (x, y)=(0.16, 0.18).

Figure 24:
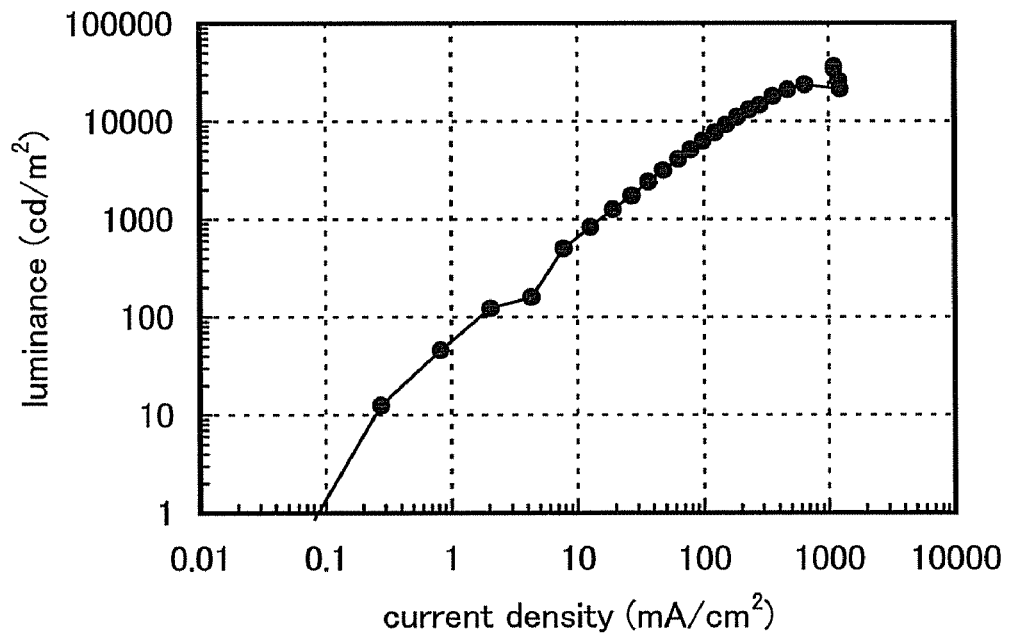
FIG. 24 shows current density vs. luminance characteristics of a light-emitting element fabricated in Example.
Figure 25:
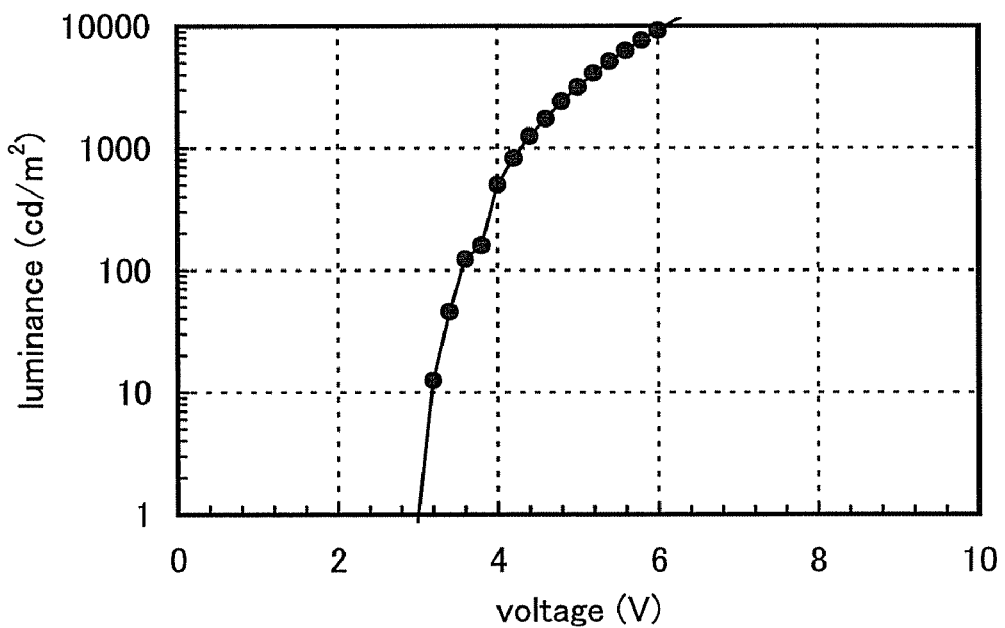
FIG. 25 shows voltage vs. luminance characteristics of the light-emitting element fabricated in Example.
Figure 26:
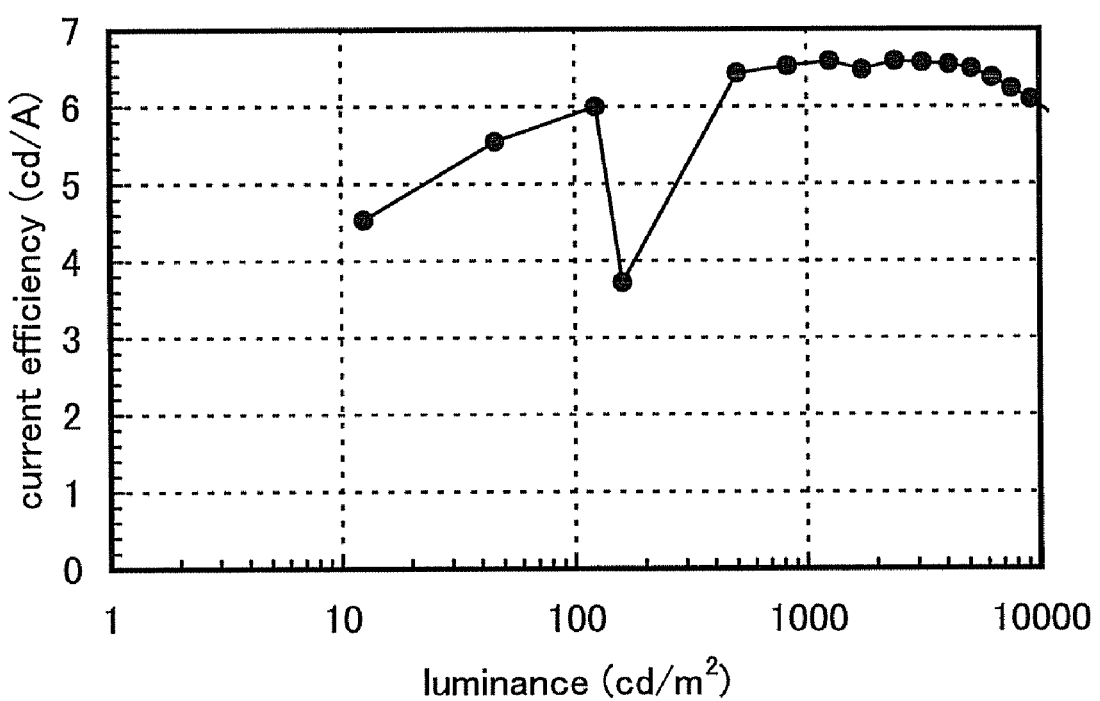
FIG. 26 shows luminance vs. current efficiency characteristics of the light-emitting element fabricated in Example.

FIG. 24 shows current density vs. luminance characteristics of the light-emitting element 3. In FIG. 24, the horizontal axis represents current density (mA/cm$^2$) and the vertical axis represents luminance (cd/m$^2$). FIG. 25 shows voltage vs. luminance characteristics thereof. In FIG. 25, the horizontal axis represents applied voltage (V) and the vertical axis represents emission luminance (cd/m$^2$). FIG. 26 shows luminance vs. current efficiency characteristics thereof. In FIG. 26, the horizontal axis represents emission luminance (cd/m$^2$) and the vertical axis represents current efficiency (cd/A).

In the light-emitting element 3, a voltage necessary for a luminance of 830 cd/m$^2$ was 4.2 V, and a current flowing at that time was 0.51 mA (current density was 12.7 mA/cm$^2$). The current efficiency at that time was 6.5 cd/A.

The above description reveals that by forming a hole-transporting layer and the layer including a composite material of a light-emitting element, using an aromatic amine compound of one embodiment of the present invention, the light-emitting element can have excellent element characteristics and long lifetime.

The present application is based on Japanese Patent Application serial No. 2008-130154 filed with Japan Patent Office on May 16, 2008, the entire contents of which are hereby incorporated by reference.

What is claimed is:

1. An aromatic amine compound represented by a general formula (1)

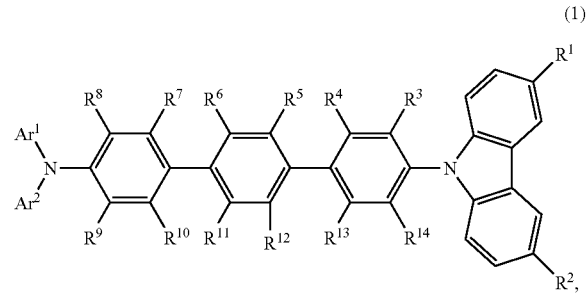

wherein:
R$^1$ and R$^2$ are independently a hydrogen atom, an alkyl group having 1 to 4 carbon atoms, or an aryl group having 6 to 13 carbon atoms;
R$^3$ to R$^{14}$ are independently a hydrogen atom or an alkyl group having 1 to 4 carbon atoms;

TABLE 3

|  | First electrode 2102 | Layer including a composite material 2103 | Hole-transporting layer 2104 | Light-emitting layer 2105 | First electron-transporting layer 2106a | Second electron-transporting layer 2106b | Electron-injecting layer 2107 | Second electrode 2108 |
|---|---|---|---|---|---|---|---|---|
| Light-emitting element 3 | ITSO 110 nm | YGTA1BP:MoOx (4:1) 50 nm | YGTA1BP 10 nm | CzPA:PCBAPA (1:0.1) 30 nm | Alq 10 nm | BPhen 20 nm | LiF 1 nm | Al 200 nm |

*The mixture ratios are all represented in weight ratios $Ar^1$ and $Ar^2$ are independently an aryl group having 6 to 13 carbon atoms; and $Ar^1$ and $Ar^2$ independently has a substituent, wherein the substituent contains an aryl group having 6 to 13 carbon atoms, and wherein the substituent of $Ar^1$ and the substituent of $Ar^2$ are bound to each other to form a ring.

2. The aromatic amine compound according to claim 1, wherein each of $R^3$ to $R^{14}$ is a hydrogen atom.

3. The aromatic amine compound according to claim 1, wherein each of $R^1$ and $R^2$ is a hydrogen atom.

4. A light-emitting element comprising, between a pair of electrodes, an aromatic amine compound represented by a general formula (1)

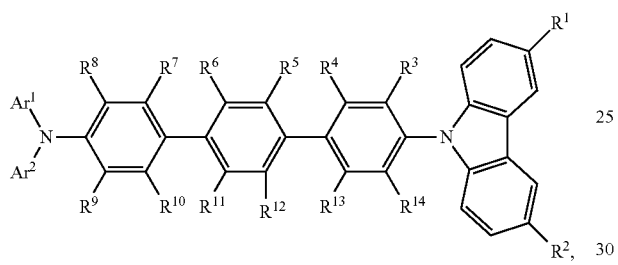

(1)

wherein:

$R^1$ and $R^2$ are independently a hydrogen atom, an alkyl group having 1 to 4 carbon atoms, or an aryl group having 6 to 13 carbon atoms;

$R^3$ to $R^{14}$ are independently a hydrogen atom or an alkyl group having 1 to 4 carbon atoms;

$Ar^1$ and $Ar^2$ are independently an aryl group having 6 to 13 carbon atoms; and $Ar^1$ and $Ar^2$ independently has a substituent, wherein the substituent is an aryl group having 6 to 13 carbon atoms, and wherein the substituent of $Ar^1$ and the substituent of $Ar^2$ are bound to each other to form a ring.

5. The light-emitting element according to claim 4, wherein each of $R^3$ to $R^{14}$ is a hydrogen atom.

6. The light-emitting element according to claim 4, wherein each of $R^1$ and $R^2$ is a hydrogen atom.

7. The light-emitting element according to claim 4, wherein the light-emitting element comprises a light-emitting layer between the pair of electrodes, and wherein the aromatic amine compound is included in the light-emitting layer.

8. The light-emitting element according to claim 4, wherein the light-emitting element comprises, between the pair of electrodes, a light-emitting layer and a layer which is in contact with the light-emitting layer, and wherein the aromatic amine compound is included in the layer.

9. The light-emitting element according to claim 4, wherein the light-emitting element comprises a light-emitting layer between the pair of electrodes, and wherein the light-emitting layer includes a phosphorescent material that emits phosphorescence.

10. An electronic device including an light-emitting element which comprises, between a pair of electrodes, an aromatic amine compound represented by a general formula (1)

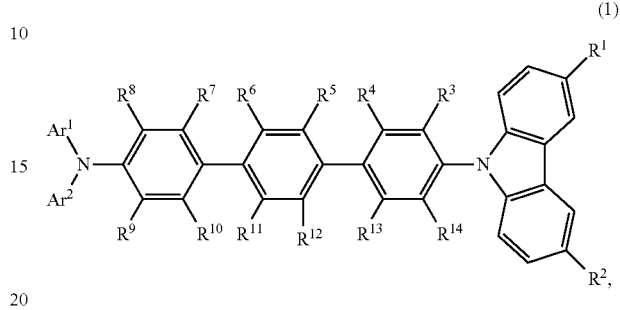

(1)

wherein:

$R^1$ and $R^2$ are independently a hydrogen atom, an alkyl group having 1 to 4 carbon atoms, or an aryl group having 6 to 13 carbon atoms;

$R^3$ to $R^{14}$ are independently a hydrogen atom or an alkyl group having 1 to 4 carbon atoms;

$Ar^1$ and $Ar^2$ are independently an aryl group having 6 to 13 carbon atoms; and $Ar^1$ and $Ar^2$ independently has a substituent, wherein the substituent contains an aryl group having 6 to 13 carbon atoms, and wherein the substituent of $Ar^1$ and the substituent of $Ar^2$ are bound to each other to form a ring.

11. The electronic device according to claim 10, wherein each of $R^3$ to $R^{14}$ is a hydrogen atom.

12. The electronic device according to claim 10, wherein each of $R^1$ and $R^2$ is a hydrogen atom.

13. The electronic device according to claim 10, wherein the light-emitting element comprises a light-emitting layer between the pair of electrodes, and wherein the aromatic amine compound is included in the light-emitting layer.

14. The electronic device according to claim 10, wherein the light-emitting element comprises, between the pair of electrodes, a light-emitting layer and a layer which is in contact with the light-emitting layer, and wherein the aromatic amine compound is included in the layer.

15. The electronic device according to claim 10, wherein the light-emitting element comprises a light-emitting layer between the pair of electrodes, and wherein the light-emitting layer includes a phosphorescent material that emits phosphorescence.

16. The electronic device according to claim 10, wherein the electronic device is a lighting device.

17. An aromatic amine compound represented by a general formula (1)

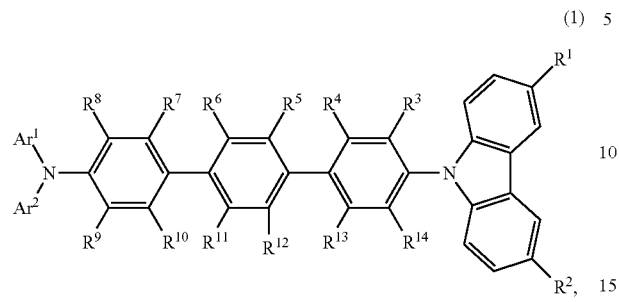

wherein:
$R^1$ and $R^2$ are independently an alkyl group having 1 to 4 carbon atoms, or an aryl group having 6 to 13 carbon atoms;
$R^3$ to $R^{14}$ are independently a hydrogen atom or an alkyl group having 1 to 4 carbon atoms;
$Ar^1$ and $Ar^2$ are independently an aryl group having 6 to 13 carbon atoms; and
$R^1$ and $R^2$ independently has a substituent,
wherein the substituent contains an aryl group having 6 to 13 carbon atoms, and
wherein the substituent of $R^1$ and the substituent $R^2$ are bound to each other to form a ring.

18. A lighting device including an light-emitting element which comprises, between a pair of electrodes, an aromatic amine compound represented by a general formula (1)

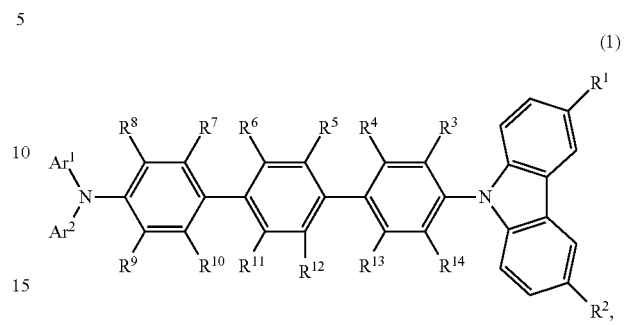

wherein:
$R^1$ and $R^2$ are independently an alkyl group having 1 to 4 carbon atoms, or an aryl group having 6 to 13 carbon atoms;
$R^3$ to $R^{14}$ are independently a hydrogen atom or an alkyl group having 1 to 4 carbon atoms;
$Ar^1$ and $Ar^2$ are independently an aryl group having 6 to 13 carbon atoms; and
$R^1$ and $R^2$ independently has a substituent,
wherein the substituent contains an aryl group having 6 to 13 carbon atoms, and
wherein the substituent of $R^1$ and the substituent $R^2$ are bound to each other to form a ring.

* * * * *